(12) United States Patent
Piwinski et al.

(10) Patent No.: US 11,168,075 B2
(45) Date of Patent: *Nov. 9, 2021

(54) COMPOUNDS AND THEIR USE FOR REDUCING URIC ACID LEVELS

(71) Applicant: Acquist LLC, Chatham, NJ (US)

(72) Inventors: John J. Piwinski, Lebanon, NJ (US); Ronald N. Buckle, Rensselaer, NY (US); Alexandre Larivée, Montréal (CA); Arshad Siddiqui, Newton, MA (US); Raymond P. Warrell, Jr., Chatham, NJ (US)

(73) Assignee: Acquist LLC, Chatham, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/928,623

(22) Filed: Jul. 14, 2020

(65) Prior Publication Data

US 2020/0347034 A1    Nov. 5, 2020

Related U.S. Application Data

(63) Continuation of application No. 16/310,921, filed as application No. PCT/US2017/038522 on Jun. 21, 2017, now Pat. No. 10,759,784.

(60) Provisional application No. 62/358,669, filed on Jul. 6, 2016, provisional application No. 62/356,685, filed on Jun. 30, 2016.

(51) Int. Cl.
| | |
|---|---|
| *C07D 403/12* | (2006.01) |
| *A61P 19/06* | (2006.01) |
| *A61K 9/00* | (2006.01) |
| *C07D 401/14* | (2006.01) |
| *C07D 413/12* | (2006.01) |
| *C07D 417/12* | (2006.01) |
| *C07D 487/04* | (2006.01) |
| *C07D 498/04* | (2006.01) |
| *A61K 31/506* | (2006.01) |

(52) U.S. Cl.
CPC .......... *C07D 403/12* (2013.01); *A61K 9/0019* (2013.01); *A61K 31/506* (2013.01); *A61P 19/06* (2018.01); *C07D 401/14* (2013.01); *C07D 413/12* (2013.01); *C07D 417/12* (2013.01); *C07D 487/04* (2013.01); *C07D 498/04* (2013.01)

(58) Field of Classification Search
CPC .................................... C07D 403/12
USPC ........................................ 544/300
See application file for complete search history.

(56) References Cited

U.S. PATENT DOCUMENTS

| | | |
|---|---|---|
| 4,034,093 A | 7/1977 | Klemm et al. |
| 4,239,762 A | 12/1980 | Kramer et al. |
| 4,602,912 A | 7/1986 | De Sousa et al. |
| 4,634,707 A | 1/1987 | Brewer et al. |
| 4,636,508 A | 1/1987 | Brewer et al. |
| 4,762,830 A | 8/1988 | Sturm et al. |
| 4,879,276 A | 11/1989 | Brewer |
| 4,880,811 A | 11/1989 | Warrell, Jr. |
| 6,335,332 B1 | 1/2002 | Ambrogio et al. |
| 7,119,201 B2 | 10/2006 | Reiter et al. |
| 9,428,466 B2 | 8/2016 | Warrell |
| 10,093,658 B2 * | 10/2018 | Warrell, Jr. ............... A61P 3/00 |
| 10,688,095 B2 * | 6/2020 | Warrell, Jr. ............. A61P 19/06 |
| 10,752,613 B2 | 8/2020 | Piwinski et al. |
| 10,759,784 B2 * | 9/2020 | Piwinski .............. C07D 487/04 |
| 2009/0264401 A1 | 10/2009 | Gill et al. |

FOREIGN PATENT DOCUMENTS

| | | |
|---|---|---|
| JP | S60166669 A | 8/1985 |
| WO | 88/10114 A1 | 12/1988 |
| WO | 91/13623 A1 | 9/1991 |
| WO | 2015/073317 A1 | 5/2015 |
| WO | 2015/123003 A1 | 8/2015 |
| WO | 2016/118611 A1 | 7/2016 |

OTHER PUBLICATIONS

Walter Wilson Journal of the Chemical Society (1948) 1157-61.*
Elzein et al. Journal of Medicinal Chemistry (2008), 51(7), 2267-2278.*
Non-Final Office Action in U.S. Appl. No. 16/872,629, dated Nov. 19, 2020, 12 pages.
CAS Abstract US4634707 (1987), 2 pages.
CAS Registry No. 1349276-03-4 (2011), 1 page.
International Preliminary Report on Patentability in PCT/US2016/014107, dated Aug. 3, 2017, 7 pages.
International Search Report and Written Opinion in Intl. Appl. No. PCT/US2017/038525, dated Aug. 22, 2017, 16 pgs.
International Search Report and Written Opinion in PCT/US15/12370, dated Apr. 17, 2015, 10 pages.
International Search Report and Written Opinion in PCT/US2016/014107, dated May 17, 2016, 11 pages.
International Search Report and Written Opinion in PCT/US2017/038522, dated Oct. 3, 2017, 20 pages.
International Search Report and Written Opinion in PCT/US2017/040836, dated Sep. 12, 2017, 15 pages.
Non-Final Office Action dated Oct. 5, 2017, in U.S. Appl. No. 15/118,243, 21 pages.
Partial Search Report in PCT Application No. PCT/US2017/038522, dated Aug. 15, 2017, 2 pgs.

(Continued)

*Primary Examiner* — Kahsay Habte
(74) *Attorney, Agent, or Firm* — Servilla Whitney LLC

(57) ABSTRACT

Bifunctional compounds that increase uric acid excretion and reduce uric acid production, and monofunctional compounds that either increase uric acid excretion or reduce uric acid production. Methods of using these compounds for reducing uric acid levels in blood or serum, for treating disorders of uric acid metabolism, and for maintaining normal uric acid levels in blood or serum are also provided. Pharmaceutical compositions comprising the bifunctional and monofunctional compounds are also provided.

17 Claims, 44 Drawing Sheets

(56) References Cited

OTHER PUBLICATIONS

Provisional Opinion Accompanying the Partial Search Result in EP 15 748 739.8, dated May 22, 2017, 5 pages.
Search Opinion in EP Application No. 15 748 739.8, dated Sep. 1, 2017, 5 pgs.
Supplementary Partial European Search Report in EP 15 74 8739, dated May 22, 2017, 4 pages.
Non-Final Office Action in U.S. Appl. No. 16/310,921 dated Mar. 6, 2020, 9 pages .
Non-Final Office Action in U.S. Appl. No. 16/310,950 dated Jan. 15, 2020, 12 pages .
PCT International Preliminary Report on Patentability in PCT/US2017/038522 dated Jan. 10, 2019, 9 pages.
PCT International Preliminary Report on Patentability in PCT/US2017/038525 dated Jan. 10, 2019, 7 pages.
PCT Preliminary Report on Patentability in PCT/US2015/012370 dated Aug. 25, 2016, 7 pages.
Lebedyeva, Iryna O., et al., "Reaction of barbituric acid with organic azides and phosphonium ylides", Central European Journal of Chemistry, vol. 11, No. 6, 2013, pp. 1019-1022.
Wilson, Walter , "Journal of the Chemical Society (1948) pp. 1157-1161".
Non-Final Office Action in U.S. Appl. No. 16/928,629, dated Mar. 12, 2021, 8 pages.

* cited by examiner

COMPOUNDS AND THEIR USE FOR REDUCING URIC ACID LEVELS

CROSS REFERENCE TO RELATED APPLICATIONS

This is a continuation of U.S. application Ser. No. 16/310,921, filed on Dec. 18, 2018, which is the National Phase entry of International Application No. PCT/US2017/038522, filed on Jun. 21, 2017, which claims priority to U.S. Provisional Appln. Ser. No. 62/356,685, filed on Jun. 30, 2016, and to U.S. Provisional Appln. Ser. No. 62/358,669, filed on Jul. 6, 2016, the disclosures of which are incorporated herein by reference in their entireties.

TECHNICAL FIELD

This invention relates to pharmaceutical compositions and methods for reducing uric acid in blood or serum of a subject employing bifunctional and monofunctional compounds as active agents.

BACKGROUND

Gout afflicts more than 8 million U.S. subjects, and is associated with chronic elevation of uric acid (UA) in blood. The incidence of this condition has doubled in the past ten years. When UA exceeds solubility limits, it forms crystals that settle into joints and kidney, causing severe pain, destructive arthritis, and kidney failure. Treatment for chronic gout entails extended—if not lifelong—therapy focused on reducing UA production or increasing its excretion. The standard-of-care for initial therapy of gout is allopurinol, a drug that inhibits xanthine oxidase (XO), a key production enzyme. Launched in 2009, Uloric® (febuxostat; Takeda), has similar activity as an XO inhibitor with somewhat higher efficacy and improved safety. Xanthine oxidase inhibitors are used as initial therapy in more than 90% of gout patients; nonetheless, the therapeutic target is achieved in less than one-third of patients, the drugs have multiple side effects, and hypersensitivity (especially to allopurinol) is common. Given that most patients do not actually respond, the continued use of ineffective treatment administered over many months in order to determine the low percentage of patients who might respond represents an important burden to patients as well as substantial costs to global healthcare systems, Moreover, the high proportion of failures causes many patients to become non-compliant with therapy and thus at increased risk for development of chronic complications of gout, especially destructive arthritis and renal insufficiency.

Since 2000, rapid advances in the biology of proteins known as transporters have presented an array of new drug targets. The enzyme URAT1 is a high capacity renal transporter that reabsorbs most of the UA that is initially filtered into the urine from the blood by the kidney. Inhibitors of certain urate transporters may prevent such reabsorption and thereby increase UA excretion. Several drugs are now known to inhibit URAT1, including benzbromarone (approved but withdrawn in the US by Sanofi in 2003), and lesinurad (Zurampic®, AstraZeneca), which was approved in the U.S. and EU in 2016.

These drugs are all mono-functional. That is, they inhibit only one of the two equilibrium paths that reduce the levels of UA in blood (i.e., decreased production or increased excretion). Allopurinol is an example of a drug that decreases UA production by inhibiting xanthine oxidase, but it has no effect on renal excretion. As expected, allopurinol does not affect the activity of URAT1 or other renal urate transporters. Benzbromarone and lesinurad increase UA excretion (i.e., they promote uricosuria) primarily via inhibition of URAT1, but these agents have no effect on UA production, since they have no substantial effect on xanthine oxidase. Since xanthine oxidase inhibition is the principal, preferred, and primary 1l-line form of treatment for hyperuricemia, agents that promote uricosuria are used second-line and are commonly employed only in combination with xanthine oxidase inhibitors rather than as single-agents.

Non-sedating 5-carboxanilide derivatives of barbiturates, including merbarone (5-(N-phenylcarboxamido)-2-thio-barbituric acid), have been evaluated as potential cytotoxic anticancer drugs. Subsequently, it was discovered that clinical treatment with merbarone was associated with a marked reduction of UA levels in blood. Despite these discoveries, the cytotoxic activity of merbarone completely precluded its use as a treatment for a chronic lifelong disorder of UA metabolism, since the safety of such use (primarily its genotoxicity) posed a serious risk to other aspects of human health. Such clinical utility would only be possible if the genotoxic activity could be chemically dissociated and eliminated from the hypouricemic activity. The inventors have since described a number of non-genotoxic hypouricemic derivatives of merbarone.

There exists a compelling need for new drugs than can reduce UA levels in blood and provide better treatment for patients afflicted by gout. Reduction in UA is universally acknowledged as beneficial for patients with gout and other hyperuricemic disorders, and such reduction is directly linked to patient benefit. Reduced serum UA is accepted by international drug regulatory agencies (e.g., the U.S. Food and Drug Administration [FDA], the European Medicines Agency [EMA], etc.) as an endpoint for commercial drug approval in these diseases. As previously noted, drugs that can overcome the limited clinical activity of xanthine oxidase inhibitors are available or are currently being investigated, but only as "add-ons" for combination use. The approval of lesinurad [Zurampic] is the most recent example. The present invention relates to new compounds that can provide alternatives to current therapy for elevated UA levels and treatment of disorders of UA metabolism such as gout. Certain of these compounds have the particular advantage of bifunctional activity (i.e., decreasing UA production by inhibiting xanthine oxidase and increasing UA excretion by inhibiting a renal urate transporter), making them suitable for use as initial therapy and as single agents rather than "add-on" therapies. In addition, certain of the compounds have reduced toxicity compared to prior art drugs such as merbarone.

SUMMARY

In a first aspect, compounds having a structure represented by Formula (I) are provided:

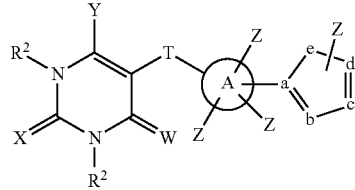

Formula (I)

wherein

W, X, and Y are each independently O, S, $NR^2$ or $N(R^2)_2$;

T is —$CONR^2$—, —$C(NR^2)NH$—, —$C(NOR^2)NH$—, —$C(N$—$NR^2)NH$—, —$C(SR^2)N$—, or —NHC(O)—;

A is phenyl, heteroaryl, C5-C10 branched or unbranched cycloalkyl, C6-C10 bicycloalkyl or C5-C10 spirocycloalkyl;

each Z is independently present or absent and, if present, is independently selected from one or more halogen atoms, —CN, —$CF_3$, —$OR^2$, —$C(O)R^2$, $SR^2$, —$S(O)_gR^3$ where g is 1 or 2, —$N(R^2)_2$, —$NO_2$, —$CO_2R^2$, —$CO_2R^3$, $OC(O)R^2$, —$CON(R^2)_2$, —$NR^2C(O)R^2$, —$SO_2N(R^2)_2$, —$NR^2SO_2R^3$, —$NR^2SO_2N(R^2)_2$ or —$NR^2C(O)N(R^2)_2$, —$C(O)NHOR^2$, alkyl, aryl, alkenyl and alkynyl;

wherein each $R^2$ is independently H, alkyl or aryl;

wherein each $R^3$ is independently alkyl or aryl, optionally substituted with one or more halogen atoms or $OR^2$; and wherein a, b, c, d, and e are each independently carbon or nitrogen, or four of a, b, c, d, and e are each independently carbon or nitrogen and one of a, b, c, d, and e is O, with the proviso that at least one of a, b, c, d and e is nitrogen, and Z is not connected directly to nitrogen or oxygen.

In a second aspect, compounds having a structure represented by Formula (II) are provided:

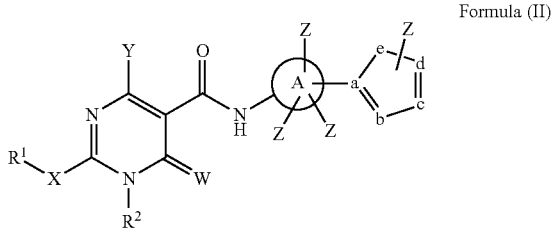

Formula (II)

wherein

W, X, and Y are each independently O, S, $NR^2$ or $N(R^2)_2$;

A is phenyl, heteroaryl, C5-C10 branched or unbranched cycloalkyl, C6-C10 bicycloalkyl or C5-C10 spirocycloalkyl;

each Z is independently present or absent and, if present, is independently selected from one or more halogen atoms, —CN, —$CF_3$, —$OR^2$, —$C(O)R^2$, $SR^2$, —$S(O)_gR^3$ where g is 1 or 2, —$N(R^2)_2$, —$NO_2$, —$CO_2R^2$, —$OCO_2R^3$, $OC(O)R^2$, —$CON(R^2)_2$, —$NR^2C(O)R^2$, —$SO_2N(R^2)_2$, —$NR^2SO_2R^3$, —$NR^2SO_2N(R^2)_2$ or —$NR^2C(O)N(R^2)_2$, —$C(O)NHOR^2$, alkyl, aryl, alkenyl and alkynyl;

wherein each $R^1$ is C1-C8 branched or unbranched alkyl, optionally substituted with Z; wherein each $R^2$ is independently H, alkyl or aryl;

wherein each $R^3$ is independently alkyl or aryl, optionally substituted with one or more halogen atoms or $OR^2$; and wherein a, b, c, d, and e are each independently carbon or nitrogen, or four of a, b, c, d, and e are each independently carbon or nitrogen and one of a, b, c, d, and e is O, with the proviso that at least one of a, b, c, d and e is nitrogen, and Z is not connected directly to nitrogen or oxygen.

In a third aspect, compounds having a structure represented by Formula (III) are provided:

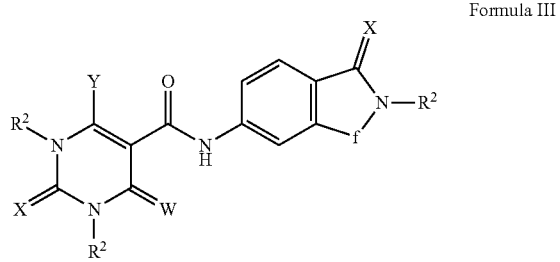

Formula III wherein

W, X, and Y are each independently O, S, $NR^2$ or $N(R^2)_2$;

each $R^2$ is independently H, alkyl or aryl; and f is divalent —$CR^2$—, —C(O)—, —$SR^2$, —$S(O)_g$— where g is 1 or 2, —$N(R')_2$—; or —$C(-O(CR^2)_nO-)$— where n=2-3.

In a fourth aspect, compounds having a structure represented by Formula (IV) are provided:

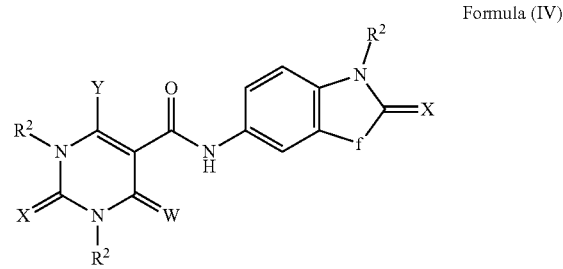

Formula (IV)

wherein

W, X, and Y are each independently O, S, $NR^2$ or $N(R^2)_2$;

each $R^2$ is independently H, alkyl or aryl; and f is divalent —$CR^2$—, —C(O)—, —$S(O)_g$— where g is 1 or 2, —$NR^2$—; or —$C(-O(CR^2)_nO-)$— where n is 2-3.

In a fifth aspect, compounds having a structure represented by Formula (V) are provided:

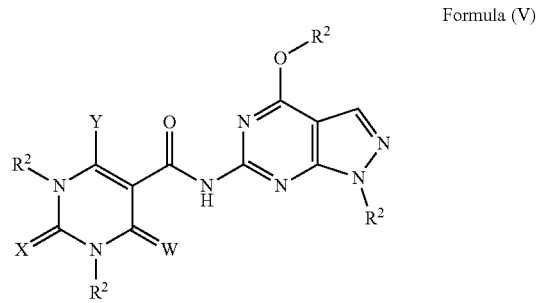

Formula (V)

wherein

W, X, and Y are each independently O, S, $NR^2$ or $N(R^2)_2$; and each $R^2$ is independently H, alkyl or aryl.

In a sixth aspect, compounds having a structure represented by Formula (VI) are provided:

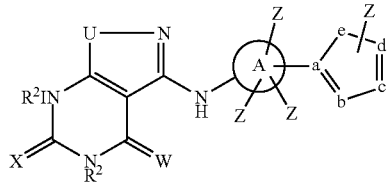

Formula (VI)

wherein
W and X are each independently O, S, NR² or N(R²)₂;
A is phenyl, heteroaryl, C5-C10 branched or unbranched cycloalkyl, C6-C10 bicycloalkyl or C5-C10 spirocycloalkyl;
each Z is independently present or absent and, if present, is independently selected from one or more halogen atoms, —CN, —CF₃, —OR², —C(O)R², SR², —S(O)$_g$R³ where g is 1 or 2, —N(R²)₂, —NO₂, —CO₂R², —OCO₂R³, OC(O)R², —CON(R²)₂, —NR²C(O)R², —SO₂N(R²)₂, —NR²SO₂R³, —NR²SO₂N(R²)₂ or —NR²C(O)N(R²)₂, —C(O)NHOR², alkyl, aryl, alkenyl and alkynyl; U is —O—, —S—, —NR²— or —S(O)$_g$— where g is 1 or 2;
wherein each R² is independently H, alkyl or aryl;
wherein each R³ is independently alkyl or aryl, optionally substituted with one or more halogen atoms or OR²; and
wherein a, b, c, d, and e are each independently carbon or nitrogen, or four of a, b, c, d, and e are each independently carbon or nitrogen and one of a, b, c, d, and e is O, with the proviso that at least one of a, b, c, d and e is nitrogen, and Z is not connected directly to nitrogen or oxygen.

In a seventh aspect, compounds having a structure represented by Formula (VII) are provided:

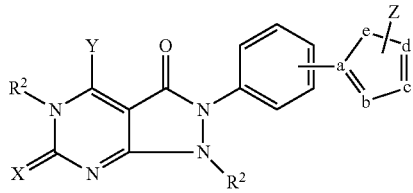

Formula (VII)

wherein
X and Y are each independently O, S, NR² or N(R²)₂;
Z is present or absent and, if present, is selected from one or more halogen atoms, —CN, —CF₃, —OR², —C(O)R², SR², —S(O)$_g$R³ where g is 1 or 2, —N(R²)₂, —NO₂, —CO₂R², —OCO₂R³, OC(O)R², —CON(R²)₂, —NR²C(O)R², —SO₂N(R²)₂, —NR²SO₂R³, —NR²SO₂N(R²)₂ or —NR²C(O)N(R²)₂, —C(O)NHOR², alkyl, aryl, alkenyl and alkynyl,
wherein each R² is independently H, alkyl or aryl;
wherein each R³ is independently alkyl or aryl, optionally substituted with one or more halogen atoms or OR²; and
wherein a, b, c, d, and e are each independently carbon or nitrogen, or four of a, b, c, d, and e are each independently carbon or nitrogen and one of a, b, c, d, and e is O, with the proviso that at least one of a, b, c, d and e is nitrogen, and Z is not connected directly to nitrogen or oxygen.

In an eighth aspect, compounds having a structure represented by Formula (VIII) are provided:

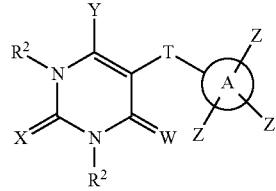

Formula (VIII)

wherein
W, X, and Y are each independently O, S, NR² or N(R²)₂;
T is —CONR²—, —C(NR²)NH—, —C(NOR²)NH—, —C(N—NR²)NH—, —C(SR²)N—, or —NHC(O)—;
A is phenyl, heteroaryl, C5-C10 branched or unbranched cycloalkyl, C6-C10 bicycloalkyl or C5-C10 spirocycloalkyl;
each Z is independently present or absent and, if present, is independently selected from one or more halogen atoms, —CN, —CF₃, —OR², —C(O)R², SR², —S(O)$_g$R³ where g is 1 or 2, —N(R²)₂, —NO₂, —CO₂R², —CO₂R³, OC(O)R², —CON(R²)₂, —NR²C(O)R², —SO₂N(R²)₂, —NR²SO₂R³, —NR²SO₂N(R²)₂ or —NR²C(O)N(R²)₂, —C(O)NHOR², alkyl, aryl, alkenyl and alkynyl;
wherein each R² is independently H, alkyl or aryl;
wherein each R³ is independently alkyl or aryl, optionally substituted with one or more halogen atoms or OR²

A further aspect relates to methods for reducing uric acid levels in blood or serum of a subject, or preventing elevation of uric acid levels in blood or serum of a subject, comprising administering a compound having a structure represented by Formula (I), Formula (II), Formula (III), Formula (IV), Formula (V), Formula (VI), Formula (VII), Formula (VIII), or a combination thereof, to a subject in need thereof in an amount effective to reduce blood or serum uric acid levels or prevent elevation of blood or serum uric acid levels. In a modification of this embodiment, the methods comprise administering a compound according to a specific embodiment of the compounds of Formula (I), Formula (II), Formula (III), Formula (IV), Formula (V), Formula (VI), Formula (VII), Formula (VIII,) or a combination thereof, as described above, to a subject in need thereof in an amount effective to reduce blood or serum uric acid levels or prevent elevation of blood or serum uric acid levels.

In certain embodiments of these methods, a compound having a structure represented by Formula (I), Formula (II), Formula (III), Formula (IV), Formula (V), Formula (VI), Formula (VII), Formula (VIII), or a combination thereof, is administered to a subject with gout, hyperuricemia, kidney disease, arthritis, kidney stones, kidney failure, urolithiasis, plumbism, hyperparathyroidism, psoriasis, inborn genetic errors of metabolism (including but not limited to Lesch-Nyhan syndrome), sarcoidosis, cardiovascular disease (including but not limited to atherosclerosis), or who is undergoing transplantation of blood, bone marrow or solid organs to reduce uric acid levels.

A further aspect relates to methods for treating a disorder of uric acid metabolism associated with or caused by elevated uric acid in blood or serum comprising administering to a subject in need thereof a compound having a structure represented by Formula (I), Formula (II), Formula (III), Formula (IV), Formula (V), Formula (VI), Formula (VII), Formula (VIII), or a combination thereof, in an amount effective to reduce blood or serum uric acid levels or prevent elevation of blood or serum uric acid levels, thereby treating the disorder of uric acid metabolism. One such embodiment relates to methods for treating a disorder of uric acid metabolism associated with or caused by elevated uric acid in blood or serum comprising administering to the subject a compound according to a specific embodiment of the compounds of Formula (I), Formula (II), Formula (III), Formula (IV), Formula (V), Formula (VI), Formula (VII), Formula (VIII), or a combination, as described above.

A further aspect of the invention provides pharmaceutical compositions comprising a compound having a structure represented by Formula (I), Formula (II), Formula (III), Formula (IV), Formula (V), Formula (VI), Formula (VII), Formula (VIII), or a combination thereof, and a pharmaceutically acceptable carrier. In a specific embodiment, the pharmaceutical composition comprises a compound according to a specific embodiment of the compounds of Formula (I), Formula (II), Formula (III), Formula (IV), Formula (V), Formula (VI), Formula (VII), Formula (VIII), or a combination thereof, as described above.

A further aspect provides methods for synthesizing the compounds discussed above, as discussed in more detail below.

DETAILED DESCRIPTION

Figure 1:
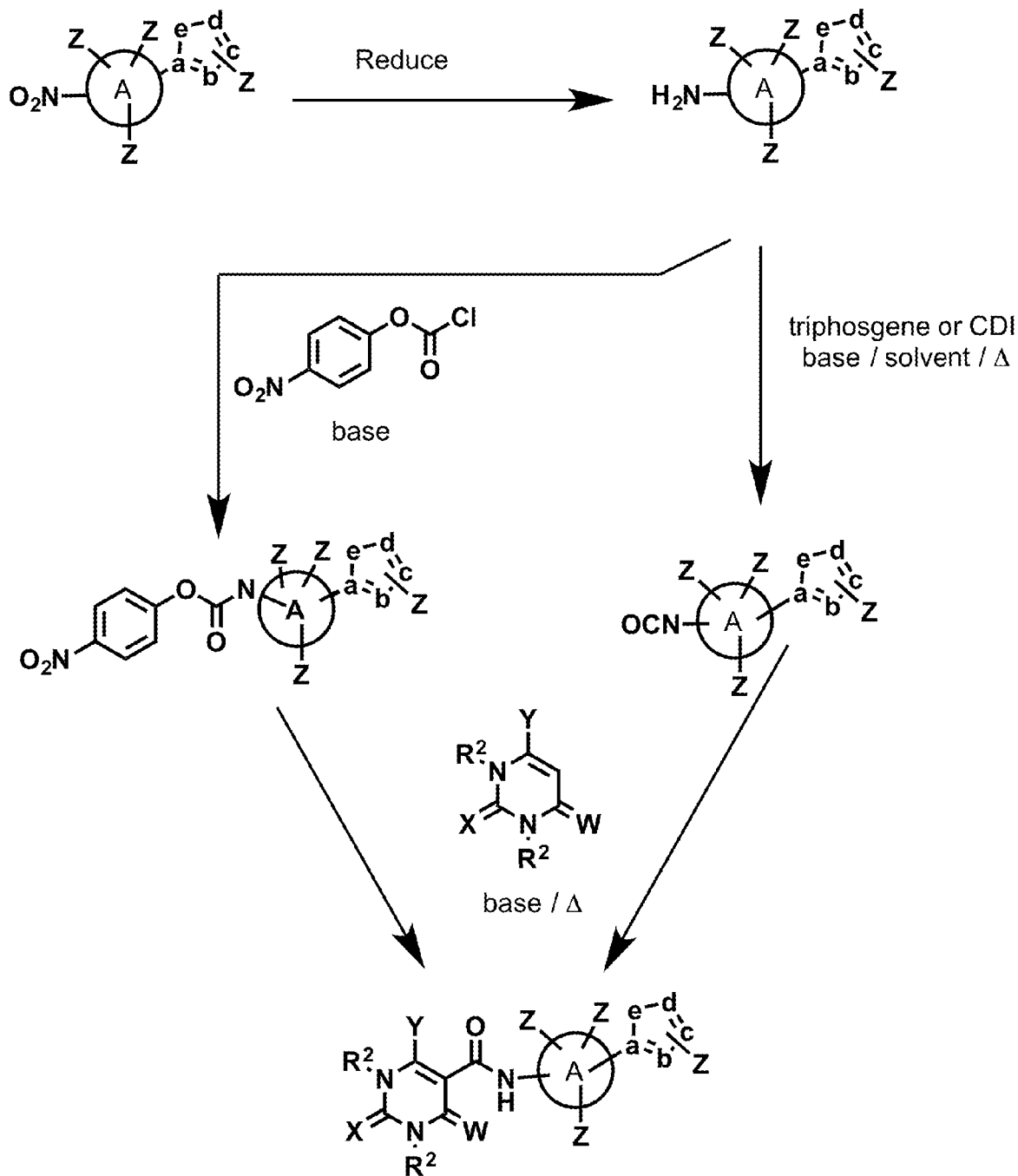
FIG. 1 illustrates a general scheme for synthesis of compounds described herein.

Before describing several exemplary embodiments provided herein, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

As used herein, the term "bifunctional" with respect to disclosed compounds means that the compound inhibits both a renal transporter, including but not limited to URAT1, and xanthine oxidase. The potency of inhibition of either target may vary, but in general an IC50 of less than about 100 μM for both xanthine oxidase and a renal transporter such as URAT1 is considered bifunctional. An IC50 of less than about 50 μM for both xanthine oxidase and URAT1 is considered a particularly active bifunctional compound, and an IC50 of less than 10 μM is considered a highly potent bifunctional compound.

As used herein, the term "monofunctional" with respect to disclosed compounds means that the compound inhibits an enzyme in the uric acid metabolic pathway involved in uric acid excretion that is either a renal transporter, including but not limited to URAT1, or an enzyme involved in uric acid production, including but not limited to xanthine oxidase, but not both. The potency of inhibition of single target may vary, but in general an IC50 of greater than about 100 μM for one of xanthine oxidase or URAT1, and an IC50 of less than about 100 NM for the other of xanthine oxidase or URAT1, is considered monofunctional. An IC50 of less than about 50 μM for one of xanthine oxidase or URAT1, and an IC50 of greater than about 100 μM for the other of xanthine oxidase or URAT1, is considered a particularly active monofunctional compound. An IC50 of less than about 10 μM for one of xanthine oxidase or URAT1, and an IC50 of greater than about 100 μM for the other of xanthine oxidase or URAT1, is considered a highly potent monofunctional compound.

As used herein, the term "treatment" refers to reducing elevated uric acid levels in blood or serum, preferably by reducing levels to the normal, low-normal or sub-normal range, with an overall goal of relieving symptoms and/or preventing recurrences of active disease. For example, a typical "therapeutic target" for treatment of elevated serum uric acid is a level ≤6.0 mg/dL. "Elevated" uric acid levels generally refer above-normal uric acid levels, as long-term elevated levels can result in conditions that require additional treatment.

As used herein, the term "preventing" elevation of uric acid levels in blood or serum refers to maintaining normal or therapeutically acceptable uric acid levels in blood or serum in a subject who would otherwise experience an increase in uric acid levels, with an overall goal of preventing development or recurrence of symptoms and/or preventing recurrences of active disease. It will be appreciated that prevention of elevation of uric acid levels is a goal of the long-term maintenance therapy discussed below, as well as certain short-term conditions.

The numbering of the positions on the barbiturate ring used herein follows the convention of Warrell (U.S. Pat. No. 4,880,811). It is also to be understood that although the compounds disclosed herein are generally illustrated by specific chemical structures, the disclosure of the compounds is intended to include their tautomers. Representative examples of tautomers in the barbiturate ring include the structures depicted below, as well as any additional tautomers on the substituents of Formula (I), Formula (II), Formula (III), Formula (IV), Formula (V), Formula (VI), Formula (VII), or Formula (VIII):

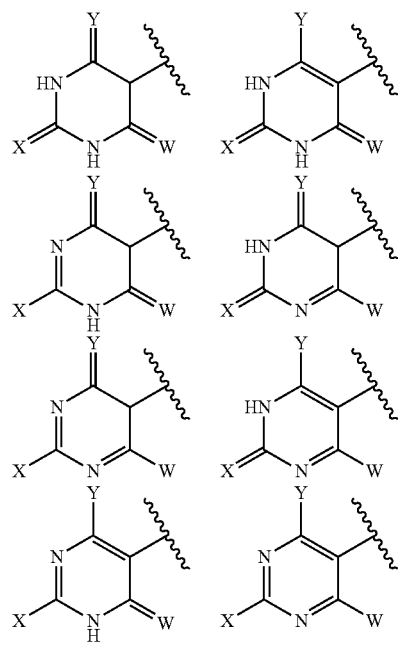

The compounds described herein meet certain needs in the therapeutic field of reduction of uric acid levels in blood and treatment of disorders of uric acid metabolism that are associated with, or caused by, elevated uric acid levels in blood or serum. Certain of the compounds are potent monofunctional inhibitors of URAT1 or xanthine oxidase. Certain of the compounds are bifunctional inhibitors of both URAT1 and xanthine oxidase.

The improved biological activity profile of the compounds of the invention and their potency make these compounds useful new drugs for reducing uric acid levels in blood, and for treating disorders of uric acid metabolism that are associated with, or caused by, elevated uric acid levels in blood or serum, including gout. Of particular significance is the advantage that the bifunctional compounds can be used effectively as monotherapy for reducing uric acid levels in blood, for treating or preventing disorders of uric acid metabolism, and specifically for treating gout.

In a first aspect, compounds having a structure represented by Formula (I) are provided:

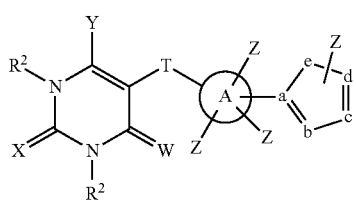

Formula (I)

wherein

W, X, and Y are each independently O, S, $NR^2$ or $N(R^2)_2$;

T is —$CONR^2$—, —$C(NR^2)NH$—, —$C(NOR^2)NH$—, —$C(N-NR^2)NH$—, —$C(SR^2)N$—, or —NHC(O)—;

A is phenyl, heteroaryl, C5-C10 branched or unbranched cycloalkyl, C6-C10 bicycloalkyl or C5-C10 spirocycloalkyl;

each Z is independently present or absent and, if present, is independently selected from one or more halogen atoms, —CN, —$CF_3$, —$OR^2$, —$C(O)R^2$, $SR^2$, —$S(O)_gR^3$ where g is 1 or 2, —$N(R^2)_2$, —$NO_2$, —$CO_2R^2$, —$OCO_2R^3$, $OC(O)R^2$, —$CON(R^2)_2$, —$NR^2C(O)R^2$, —$SO_2N(R^2)_2$, —$NR^2SO_2R^3$, —$NR^2SO_2N(R^2)_2$ or —$NR^2C(O)N(R^2)_2$, —C(O)$NHOR^2$, alkyl, aryl, alkenyl and alkynyl;

wherein each $R^2$ is independently H, alkyl or aryl;

wherein each $R^3$ is independently alkyl or aryl, optionally substituted with one or more halogen atoms or $OR^2$; and wherein a, b, c, d, and e are each independently carbon or nitrogen, or four of a, b, c, d, and e are each independently carbon or nitrogen and one of a, b, c, d, and e is O with the proviso that at least one of a, b, c, d and e is nitrogen, and Z is not connected directly to nitrogen or oxygen.

In one or more embodiments, the compound having a structure represented by Formula (I) is a compound wherein T is —$CONR^2$—.

In one or more embodiments, the compound having a structure represented by Formula (I) is a compound wherein the 5-member heterocyclic ring is a substituted or unsubstituted triazole, or a substituted or unsubstituted oxadiazole.

Specific examples of compounds having a structure represented by Formula (I) include the following:

1. A compound wherein the 5-member heterocyclic ring is unsubstituted triazole. Representative examples of such compounds include:

The compound wherein A is phenyl, T is —C(N=NH)NH—; a is C; b is CH; c and d are N; e is NH, and tautomers thereof, such as a structure represented by Formula ($I_a$):

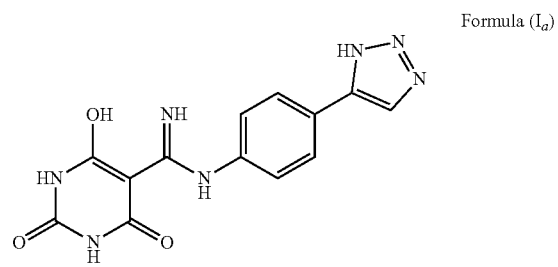 [SMILES: N=C(Nc1ccc(-c2cnn[nH]2)cc1)c1c(O)[nH]c(=O)[nH]c1=O]

Formula ($I_a$)

The compound wherein A is phenyl, T is —C($SCH_3$)=N—; a is C; b is CH; c and d are N; e is NH, and tautomers thereof, such as a structure represented by Formula ($I_b$):

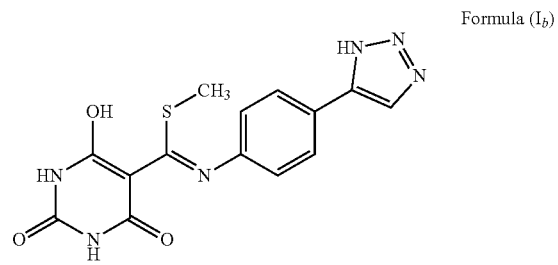 [SMILES: CS/C(=N\c1ccc(-c2cnn[nH]2)cc1)c1c(O)[nH]c(=O)[nH]c1=O]

Formula ($I_b$)

The compound wherein A is phenyl, T is —C(NOH)NH—; a is C; b is CH; c and d are N; e is NH, and tautomers thereof, such as a structure represented by Formula ($I_c$):

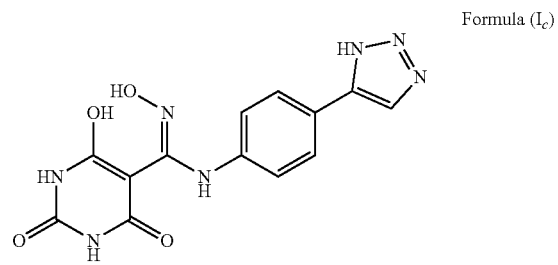 [SMILES: O=c1[nH]c(O)c(/C(=N\O)Nc2ccc(-c3cnn[nH]3)cc2)c(=O)[nH]1]

Formula ($I_c$)

The compound wherein A is phenyl, T is —C(NNH₂)NH—; is C; b is CH; c and d are N; e is NH, and tautomers thereof, such as a structure represented by Formula (I_d):

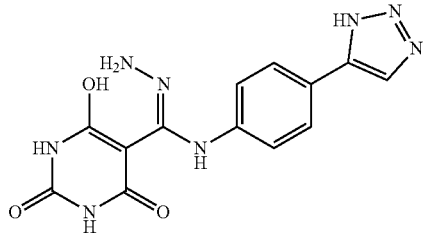

Formula (I_d)

The compound wherein A is phenyl, T is —C(O)NH—; both R² are methyl (CH₃); a is C; b is CH; C; c and d are N; e is NH, and tautomers thereof, such as a structure represented by Formula (I_e):

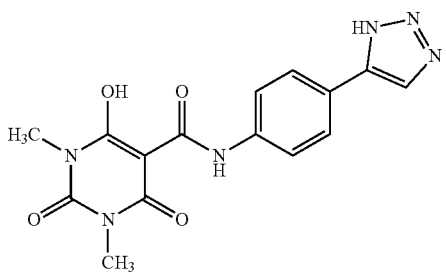

Formula (I_e)

The compound wherein A is phenyl, T is —C(NH)NH—; both R² are methyl (CH₃); a is C; b is CH; c and d are N; e is NH, and tautomers thereof, such as a structure represented by Formula (I_f):

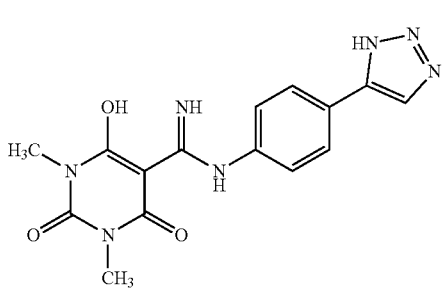

Formula (I_f)

The compound wherein A is phenyl, T is —C(O)NH—; R² on the 3-position nitrogen is methyl (CH₃); R² on the 1-position nitrogen is H; a is C; b is CH; c and d are N; e is NH, and tautomers thereof, such as a structure represented by Formula (I_g):

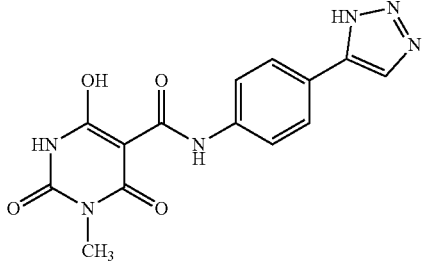

Formula (I_g)

The compound wherein A is phenyl, T is —C(NH)NH—; R² on the 3-position nitrogen is methyl (CH₃); R² on the 1-position nitrogen is H; a is C; b is CH; c and d are N; e is NH, and tautomers thereof, such as a structure represented by Formula (I_h):

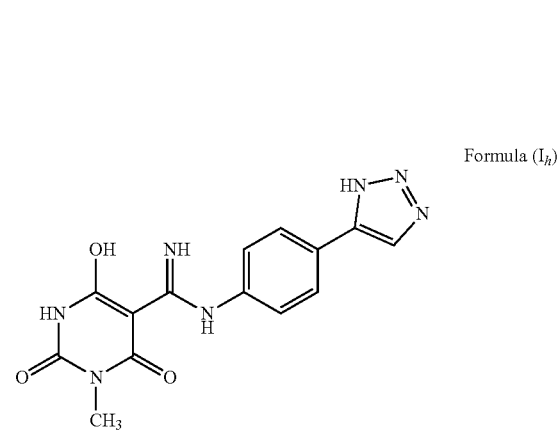 [SMILES: Cn1c(=O)[nH]c(O)c(C(=O)Nc2ccc(-c3cnn[nH]3)cc2)c1=O]

Formula (I_h)

The compound wherein A is unbranched cycloalkyl; T is —C(O)NH—; a is C; b is CH; c is NH; d and e are N, and tautomers thereof, such as a structure represented by Formula (I_i):

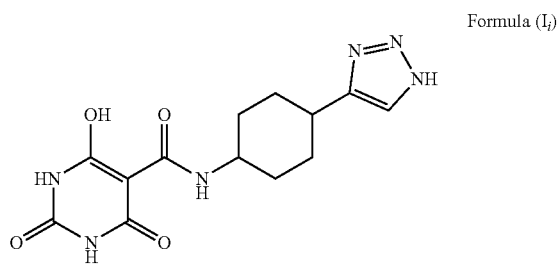 [SMILES: O=C(NC1CCC(c2c[nH]nn2)CC1)c1c(O)[nH]c(=O)[nH]c1=O]

Formula (I_i)

The compound wherein A is branched cycloalkyl; T is —C(O)NH—; a is C; b is CH; c is NH; d and e are N, Z on the cyclohexyl ring is OH, and tautomers thereof, such as a structure represented by Formula (I):

Formula (I$_j$)

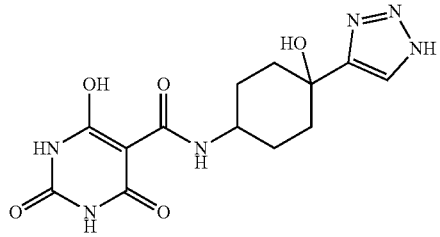

The compound wherein A is phenyl, T is —C(O)NH—; Y is NH$_2$; a is C; b is CH; c is NH; d and e are N, and tautomers thereof, such as a structure represented by Formula (I$_k$):

Formula (I$_k$)

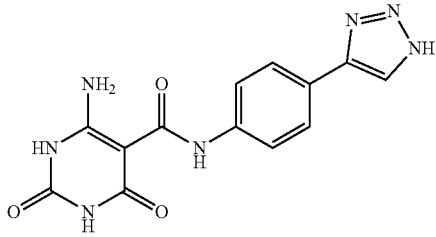

and

The compound wherein A is phenyl, T is —NHC(O)—; a is C; b is CH; c and d are N; e is NH, and tautomers thereof, such as a structure represented by Formula (I$_l$):

Formula (I$_l$)

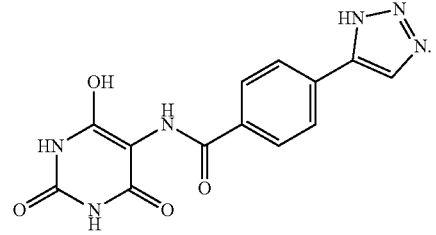

2. A compound wherein the 5-member heterocyclic ring is substituted triazole. Representative examples of such compounds include:

The compound wherein A is phenyl, T is —C(O)NH—; X is S; W is O; a is C; b is CH; c and d are N; e is NH; Z is phenyl on the triazole ring, and tautomers thereof, such as a structure represented by Formula (I$_m$):

Formula (I$_m$)

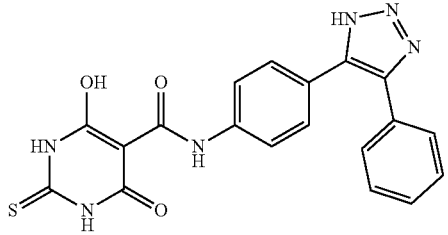

3. A compound wherein the 5-member heterocyclic ring is substituted oxadiazole. Representative examples of such compounds include:

The compound wherein A is phenyl, T is —C(O)NH—; a and c are C; b and e are N; d is O; Z on the 5-member heterocyclic ring is CF$_3$, and tautomers thereof, such as a structure represented by Formula (I):

Formula (I$_n$)

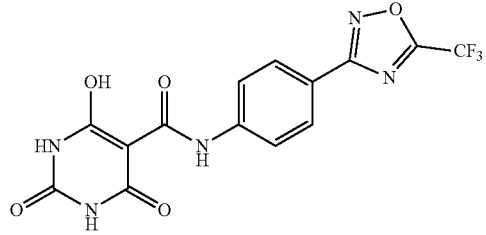

In a second aspect, compounds having a structure represented by Formula (II) are provided:

Formula (II)

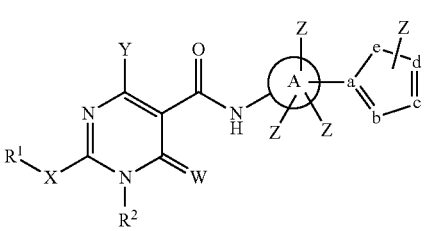

wherein
W, X, and Y are each independently O, S, NR$^2$ or N(R$^2$)$_2$;
A is phenyl, heteroaryl, C5-C10 branched or unbranched cycloalkyl, C6-C10 bicycloalkyl or C5-C10 spirocycloalkyl;
each Z is independently present or absent and, if present, is independently selected from one or more halogen atoms, —CN, —CF$_3$, —OR$^2$, —C(O)R$^2$, SR$^2$, —S(O)$_g$R$^3$ where g is 1 or 2, —N(R$^2$)$_2$, —NO$_2$, —CO$_2$R$^2$, —CO$_2$R$^3$, OC(O)R$^2$, —CON(R$^2$)$_2$, —NR$^2$C(O)R$^2$, —SO$_2$N(R$^2$)$_2$, —NR$^2$SO$_2$R$^3$, —NR$^2$SO$_2$N(R$^2$)$_2$ or —NR$^2$C(O)N(R$^2$)$_2$, —C(O)NHOR$^2$, alkyl, aryl, alkenyl and alkynyl;
wherein each R$^1$ is C1-C8 branched or unbranched alkyl, optionally substituted with Z;
wherein each R$^2$ is independently H, alkyl or aryl;
wherein each R$^3$ is independently alkyl or aryl, optionally substituted with one or more halogen atoms or OR$^2$; and wherein a, b, c, d, and e are each independently carbon or nitrogen, or four of a, b, c, d, and e are each independently carbon or nitrogen and one of a, b, c, d, and e is O, with the proviso that at least one of a, b, c, d and e is nitrogen, and Z is not connected directly to nitrogen or oxygen.

In one or more embodiments, the 5-member heterocyclic ring of the compound having a structure represented by Formula (II) is a substituted or unsubstituted triazole.

In one or more embodiments, the compound having a structure represented by Formula (II) is a compound wherein $R^1$ is —CH$_3$.

In one or more embodiments, the compound having a structure represented by Formula (II) is a compound wherein —XR$^1$ is —SCH$_3$ or —OCH$_3$.

Specific examples of compounds having a structure represented by Formula (II) include the following:

1. A compound wherein the 5-member heterocyclic ring is an unsubstituted triazole. Representative examples of such compounds include:

The compound wherein A is phenyl; X is S; R$^1$ and R$^2$ are methyl (CH$_3$); a is C; b is CH; c and d are N; e is NH, and tautomers thereof, such as a structure represented by Formula (II$_a$):

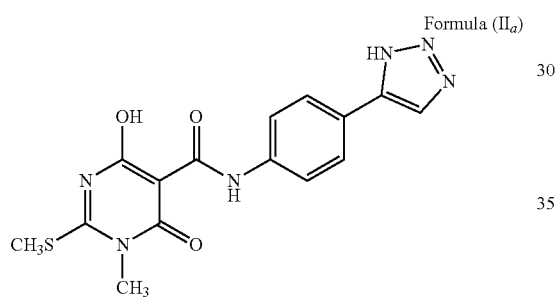

Formula (II$_a$)

The compound wherein A is phenyl; X is O; R$^1$ is methyl (CH$_3$); R$^2$ is H; a is C; b is CH; c and d are N; e is NH, and tautomers thereof, such as a structure represented by Formula (II$_b$):

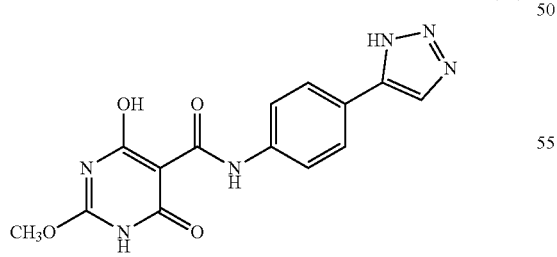

Formula (II$_b$)

The compound wherein A is phenyl; X is S; R$^1$ is methyl (CH$_3$); R$^2$ is H; a is C; b is CH; d and e are N; c is NH, and tautomers thereof, such as a structure represented by Formula (II):

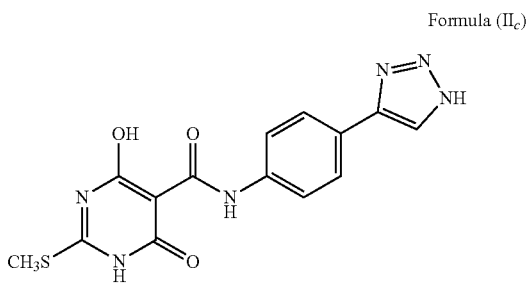

Formula (II$_c$)

The compound wherein A is phenyl; X is S; R$^1$ is —C(CH$_3$)$_2$; R$^2$ is H; a is C; b is CH; d and e are N; c is NH, and tautomers thereof, such as a structure represented by

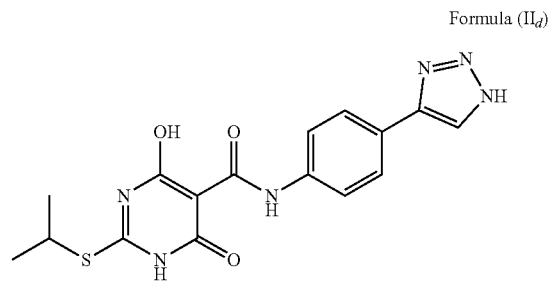 [SMILES: CC(C)Sc1nc(O)c(C(=O)Nc2ccc(-c3c[nH]nn3)cc2)c(=O)[nH]1]

Formula (II$_d$)

The compound wherein A is heteroaryl; X is S; R$^1$ is -methyl (CH$_3$); R$^2$ is H; a is C; b is CH; d and e are N; c is NH, and tautomers thereof, such as a structure represented by Formula (II$_e$):

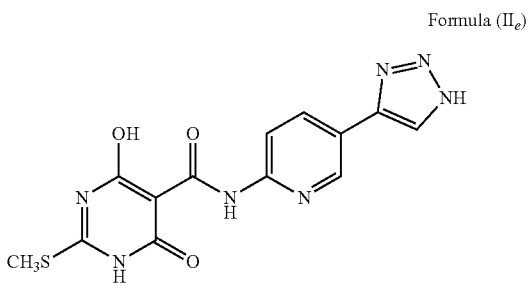

Formula (II$_e$)

and

The compound wherein A is cycloalkyl; X is S; R$^1$ is -methyl (CH$_3$); R$^2$ is H; a is C; b is CH; d and e are N; c is NH, and tautomers thereof, such as a structure represented by Formula (II$_f$):

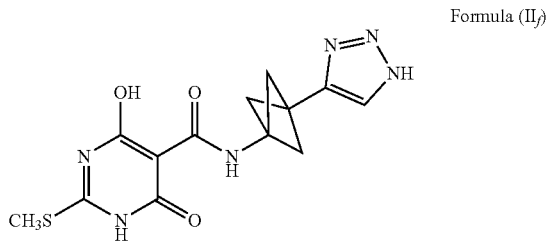

Formula (II$_f$)

2. A compound wherein the 5-member heterocyclic ring is a substituted triazole. Representative examples of such compounds include:

The compound wherein A is phenyl; X is S; $R^1$ is methyl ($CH_3$); $R^2$ is H; a is C; b is C(CH3); d and e are N; c is NH, and tautomers thereof, such as a structure represented by Formula ($II_g$):

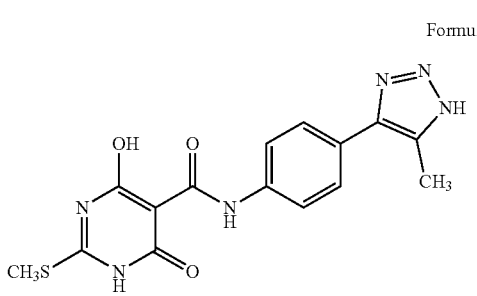

Formula ($II_g$)

and

The compound wherein A is phenyl; X is O; $R^1$ is methyl ($CH_3$); $R^2$ is H; a is C; b is C(CH3); d and e are N; c is NH, and tautomers thereof, such as a structure represented by Formula ($II_h$):

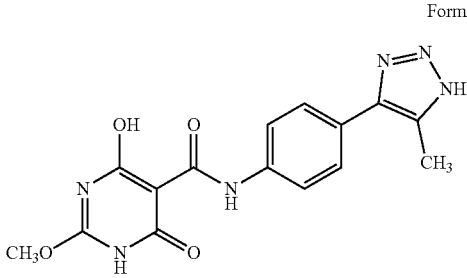

Formula ($II_h$)

In a third aspect, compounds having a structure represented by Formula (III) are provided:

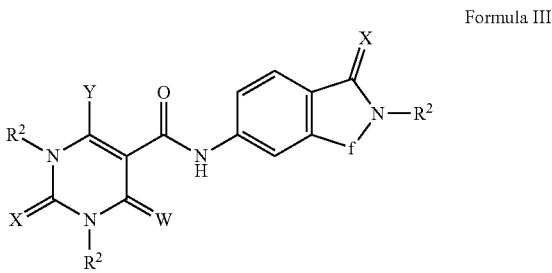

Formula III wherein

W, X, and Y are each independently O, S, $NR^2$ or $N(R^2)_2$;

each $R^2$ is independently H, alkyl or aryl; and f is divalent —$CR^2$—, —C(O)—, —$SR^2$, —$S(O)_g$— where g is 1 or 2, —$NR_2$—, or —$O(CR^2)_nO$— where n=2-3.

In one or more embodiments, the compound having a structure represented by Formula (III) is a compound wherein f is —$S(O)_g$—.

Specific examples of compounds having a structure represented by Formula (III) include the following:

1. A compound wherein X is O, $R^2$ is H, and f is —$S(O)_2$—, such as the compound having a structure represented by Formula ($III_a$) and tautomers thereof:

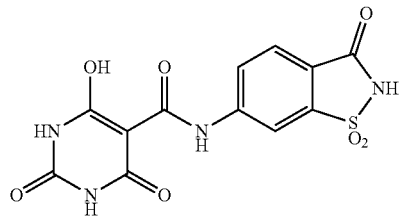

Formula ($III_a$)

In a fourth aspect, compounds having a structure represented by Formula (IV) are provided:

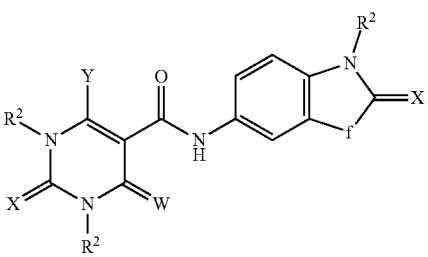

Formula (IV)

wherein

W, X, and Y are each independently O, S, $NR^2$ or $N(R^2)_2$; each $R^2$ is independently H, alkyl or aryl; and f is divalent —$CR^2$—, —C(O)—, —$S(O)_g$— where g is 1 or 2, —NR—; or —C(—$O(CR^2)_nO$—)— where n=2-3.

In one or more embodiments, the compound having a structure represented by Formula (IV) is a compound wherein f is —NH—, —C(—$O(CR^2)_nO$—)— where n=2-3, or —C(O)—.

In one or more embodiments, the compound having a structure represented by Formula (IV) is a compound wherein f is —NH—, —C(—$O(CR^2)_nO$—)— or —C(O)—, and X on the fused ring structure is O.

Specific examples of compounds having a structure represented by Formula (IV) include the following:

1. A compound wherein f is —NH (i.e., the fused ring structure is benzodiazole). Representative examples of such compounds include:

The compound wherein X on the fused ring structure is O, such as a structure represented by Formula having a structure represented by Formula ($IV_a$), and tautomers thereof:

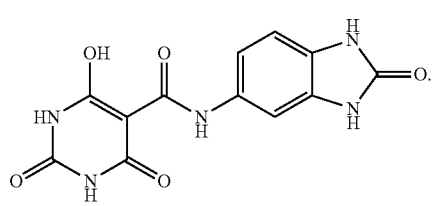

Formula ($IV_a$)

2. A compound wherein f is —CO— or —C(—(CR²)ₙO—)— (i.e., the fused ring structure is benzopyrrolidine). Representative examples of such compounds include:

The compound wherein f is —C(O)— and X on the fused ring structure is O, such as the compound having a structure represented by Formula (IV$_b$), and tautomers thereof:

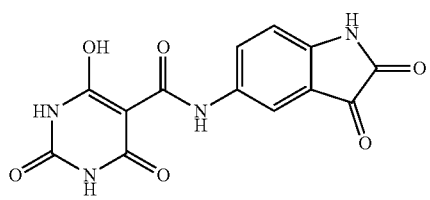

Formula (IV$_b$)

and

The compound wherein f is —C(—O(CR²)ₙO—)— and X on the fused ring structure is O, such as the compound having a structure represented by Formula (IV$_c$), and tautomers thereof:

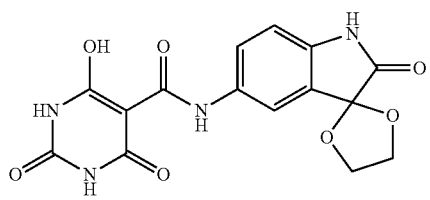

Formula (IV$_c$)

In a fifth aspect, compounds having a structure represented by Formula (V) are provided:

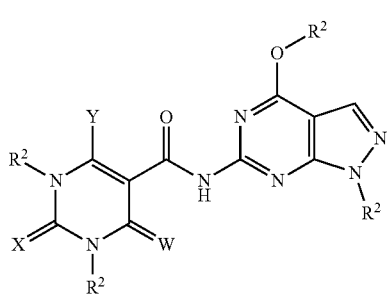

Formula (V)

wherein

W, X, and Y are each independently O, S, NR² or N(R²)₂; and each R² is independently H, alkyl or aryl.

In one or more embodiments, the compound having a structure represented by Formula (V) is a compound wherein each R² is H.

Specific examples of compounds having a structure represented by Formula (V) include the following:

1. A compound wherein each R² is H, X is O and W is O, such as the compound having a structure represented by Formula (V$_a$), and tautomers thereof:

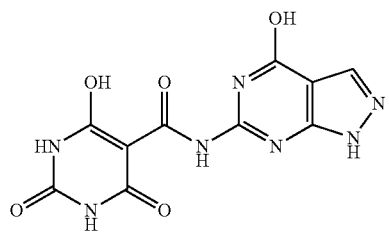

Formula (V$_a$)

In a sixth aspect, compounds having a structure represented by Formula (VI) are provided:

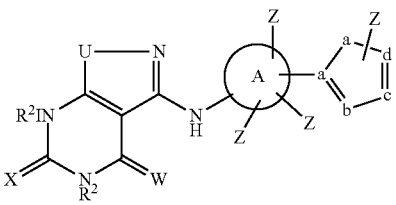

Formula (VI)

wherein

W and X are each independently O, S, NR² or N(R²)₂;

A is phenyl, heteroaryl, C5-C10 branched or unbranched cycloalkyl, C7-C10 bicycloalkyl or C5-C10 spirocycloalkyl;

each Z is independently present or absent and, if present, is independently selected from one or more halogen atoms, —CN, —CF₃, —OR², —C(O)R², SR², —S(O)$_g$R³ where g is 1 or 2, —N(R²)₂, —NO₂, —CO₂R², —CO₂R³, OC(O)R², —CON(R²)₂, —NR²C(O)R², —SO₂N(R²)₂, —NR²SO₂R³, —NR²SO₂N(R²)₂ or —NR²C(O)N(R²)₂, —C(O)NHOR², alkyl, aryl, alkenyl and alkynyl;

U is —O—, —S— —NR²— or —S(O)$_g$— where g is 1 or 2;

wherein each R² is independently H, alkyl or aryl;

wherein each R³ is independently alkyl or aryl, optionally substituted with one or more halogen atoms or OR²; and wherein a, b, c, d, and e are each independently carbon or nitrogen, or four of a, b, c, d, and e are each independently carbon or nitrogen and one of a, b, c, d, and e is O, with the proviso that at least one of a, b, c, d and e is nitrogen, and Z is not connected directly to nitrogen or oxygen.

In one or more embodiments, the compound having a structure represented by Formula (VI) is a compound wherein U is —O— or —NH—.

In one or more embodiments, the compound having a structure represented by Formula (VI) is a compound wherein the 5-member heterocyclic ring is triazole.

Specific examples of compounds having a structure represented by Formula (VI) include the following:

1. A compound wherein the 5-member heterocyclic ring is triazole and U is O. Representative examples of such compounds include:

The compound wherein X and W are O, such as the compound having a structure represented by Formula (VI$_a$), and tautomers thereof.

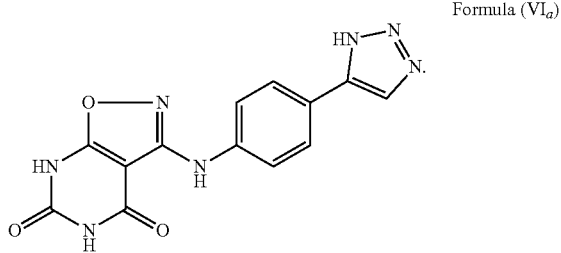 [SMILES: O=c1[nH]c(=O)c2c(Nc3ccc(-c4cnn[nH]4)cc3)noc2[nH]1]

Formula (VI$_a$)

2. A compound wherein the 5-member heterocyclic ring is triazole and U is —NH—. Representative examples of such compounds include:

The compound wherein wherein R$^2$ on both nitrogens of the barbiturate ring is —H, such as a structure represented by Formula (VI$_b$), and tautomers thereof:

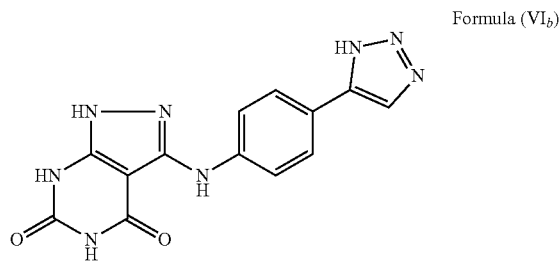 [SMILES: O=c1[nH]c(=O)c2c(Nc3ccc(-c4cnn[nH]4)cc3)n[nH]c2[nH]1]

Formula (VI$_b$)

and

The compound wherein R$^2$ on both nitrogens of the barbiturate ring is —CH$_3$, such as a structure represented by Formula (VI$_c$), and tautomers thereof:

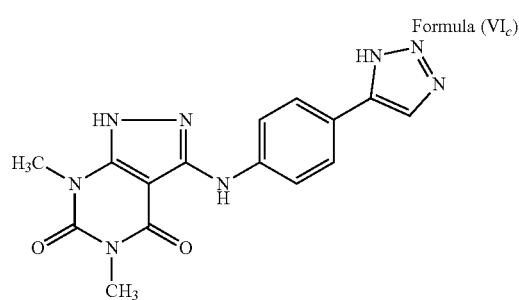 [SMILES: Cn1c(=O)c2c(Nc3ccc(-c4cnn[nH]4)cc3)n[nH]c2n(C)c1=O]

Formula (VI$_c$)

In a seventh aspect, compounds having a structure represented by Formula (VII) are provided:

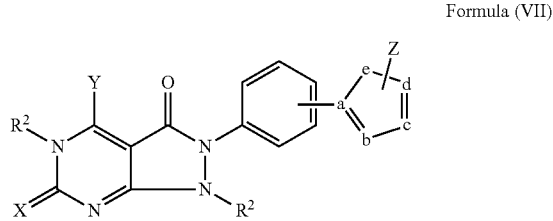

Formula (VII)

wherein
X and Y are each independently O, S, NR$^2$ or N(R$^2$)$_2$;
Z is present or absent and, if present, is selected from one or more halogen atoms, —CN, —CF$_3$, —OR$^2$, —C(O)R$^2$, SR$^2$, —S(O)$_g$R$^3$ where g is 1 or 2, —N(R$^2$)$_2$, —NO$_2$, —CO$_2$R$^2$, —OCO$_2$R$^3$, OC(O)R$^2$, —CON(R$^2$)$_2$, —NR$^2$C(O)R$^2$, —SO$_2$N(R$^2$)$_2$, —NR$^2$SO$_2$R$^3$, —NR$^2$SO$_2$N(R$^2$)$_2$ or —NR$^2$C(O)N(R$^2$)$_2$, —C(O)NHOR$^2$, alkyl, aryl, alkenyl and alkynyl,
wherein each R$^2$ is independently H, alkyl or aryl; and
wherein a, b, c, d, and e are each independently carbon or nitrogen, or four of a, b, c, d, and e are each independently carbon or nitrogen and one of a, b, c, d, and e is O, with the proviso that at least one of a, b, c, d and e is nitrogen, and Z is not connected directly to nitrogen or oxygen.

In one or more specific embodiments, the compound having a structure represented by Formula (VII) is a compound wherein the unfused 5-member heterocyclic ring is triazole.

Specific examples of compounds having a structure represented by Formula (VII) include the following:

1. A compound wherein the unfused 5-member heterocyclic ring is triazole and each R$^2$ is H. Representative examples of such compounds include:

The compound wherein a is C; b is CH; c and d are N and e is NH, such as the compound having a structure represented by Formula (VII$_a$), and tautomers thereof:

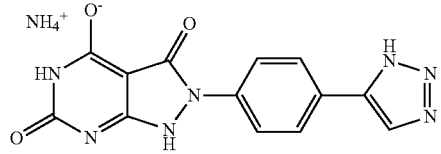

Formula (VII$_a$)

In an eighth aspect, compounds having a structure represented by Formula (VIII) are provided:

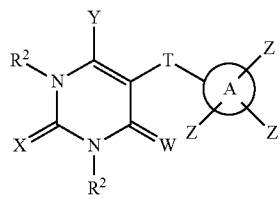

Formula (VIII)

wherein
W, X, and Y are each independently O, S, NR$^2$ or N(R$^2$)$_2$;
T is —CONR$^2$—, —C(NR$^2$)NH—, —C(NOR$^2$)NH—, —C(N—NR$^2$)NH—, —C(SR$^2$)N—, or —NHC(O)—;
A is phenyl, heteroaryl, C5-C10 branched or unbranched cycloalkyl, C6-C10 bicycloalkyl or C5-C10 spirocycloalkyl;
each Z is independently present or absent and, if present, is independently selected from one or more halogen atoms, —CN, —CF$_3$, —OR$^2$, —C(O)R$^2$, SR$^2$, —S(O)$_f$R$^3$ where f is 1 or 2, —N(R$^2$)$_2$, —NO$_2$, —CO$_2$R$^2$, —CO$_2$R$^3$, OC(O)R$^2$, —CON(R$^2$)$_2$, —NR$^2$C(O)R$^2$, —SO$_2$N(R$^2$)$_2$, —NR$^2$SO$_2$R$^3$, —NR$^2$SO$_2$N(R$^2$)$_2$ or —NR$^2$C(O)N(R$^2$)$_2$, —C(O)NHOR$^2$, alkyl, aryl, alkenyl and alkynyl;
wherein each R$^2$ is independently H, alkyl or aryl;
wherein each R$^3$ is independently alkyl or aryl, optionally substituted with one or more halogen atoms or OR$^2$.

In one or more specific embodiments, the compound having a structure represented by Formula (VIII) is a compound wherein Z is —C(O)NHOR$^2$ Specific examples of compounds having a structure represented by Formula (VIII) include the following:

1. A compound wherein Z is —C(O)NHOR$^2$. Representative examples of such compounds include:

The compound wherein A is phenyl, such as the compound having a structure represented by Formula (VIII$_a$), and tautomers thereof:

Formula (VIII$_a$)

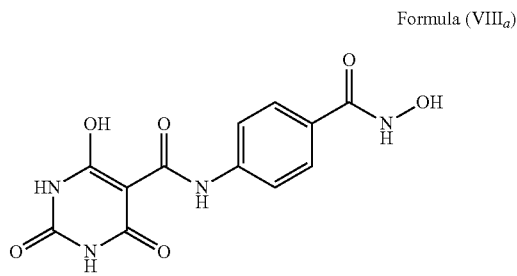 [SMILES: O=C(NO)c1ccc(NC(=O)c2c(O)[nH]c(=O)[nH]c2=O)cc1]

and

The compound wherein A is heteroaryl (for example pyridine), such as the compound having a structure represented by Formula (VIII$_b$), and tautomers thereof:

Formula (VIII$_b$)

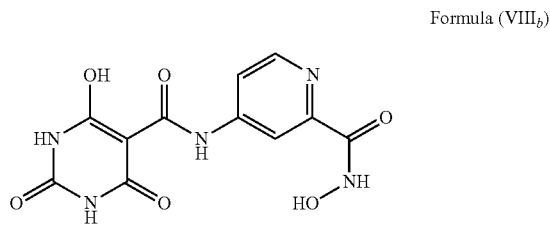 [SMILES: O=C(NO)c1cc(NC(=O)c2c(O)[nH]c(=O)[nH]c2=O)ccn1]

As disclosed herein, reference to compounds having a structure represented by any of Formulae (I)—(VIII), or a combination thereof, is intended to include all compounds falling within the generic structure, as well as the specific embodiments described and their tautomers.

Figure 2:
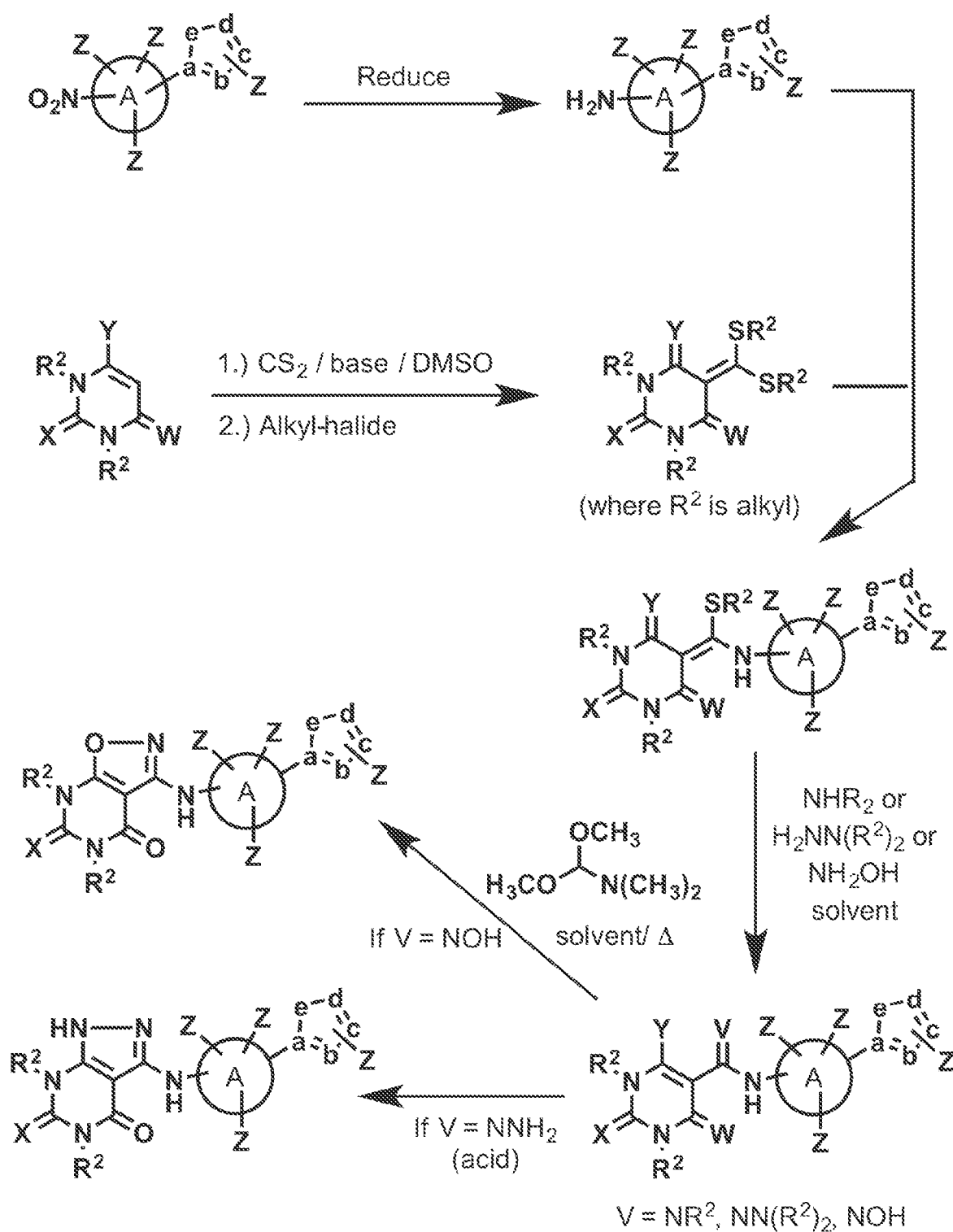
FIG. 2 illustrates a general scheme for synthesis of bridged compounds.
Figure 3:
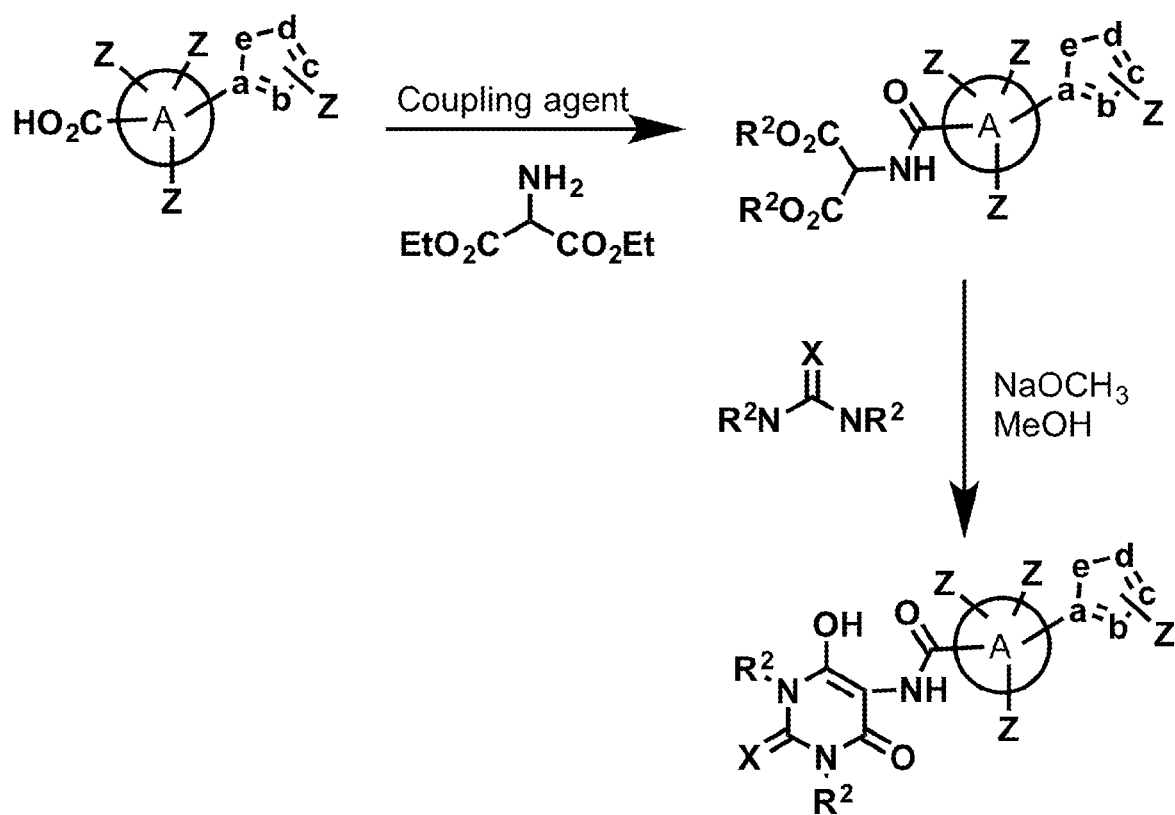
FIG. 3 illustrates an alternative general scheme for synthesis of compounds.
Figure 4:
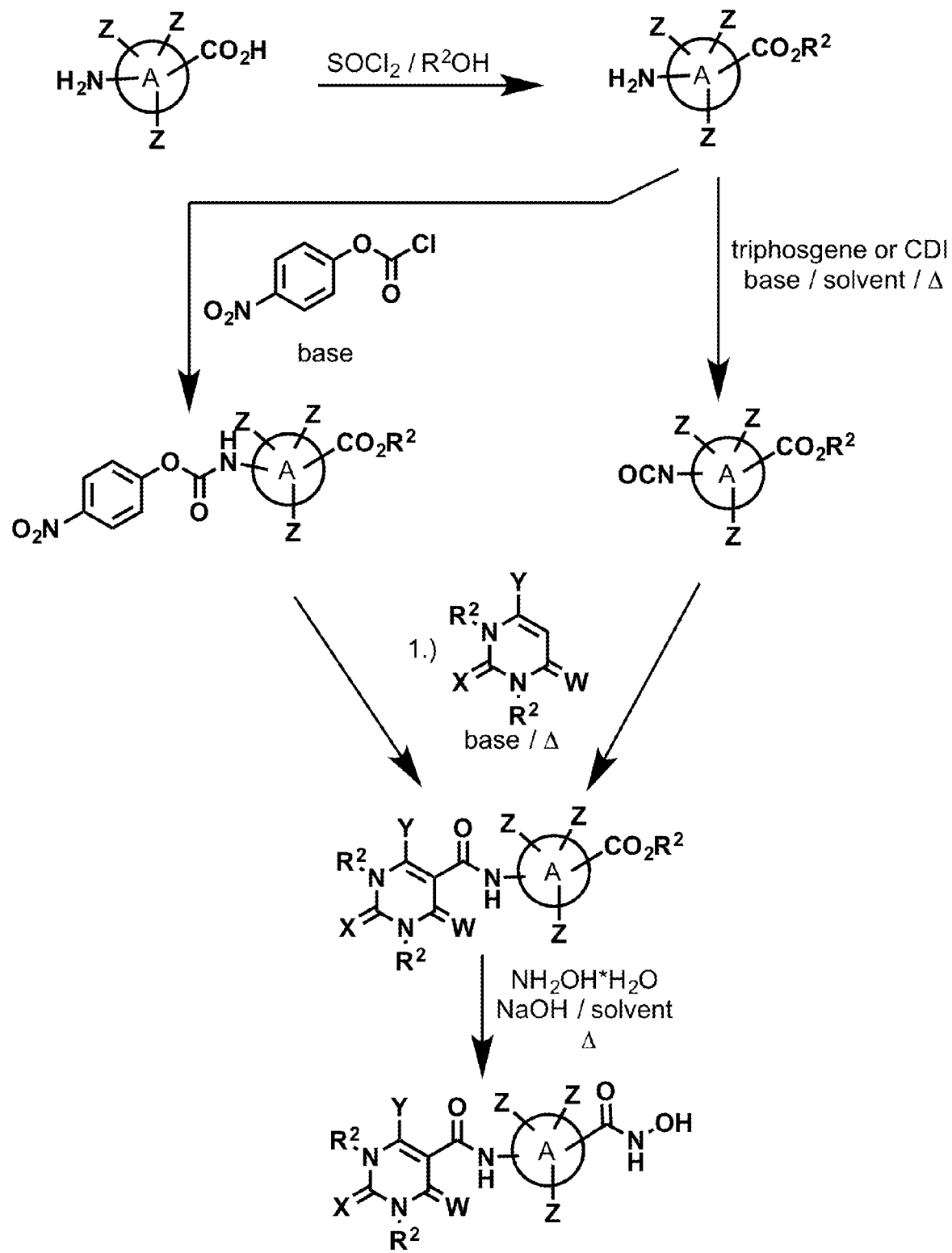
FIG. 4 illustrates a general scheme for synthesis of compounds containing a hydroxamic acid in place of the heterocyclic ring.
Figure 5:
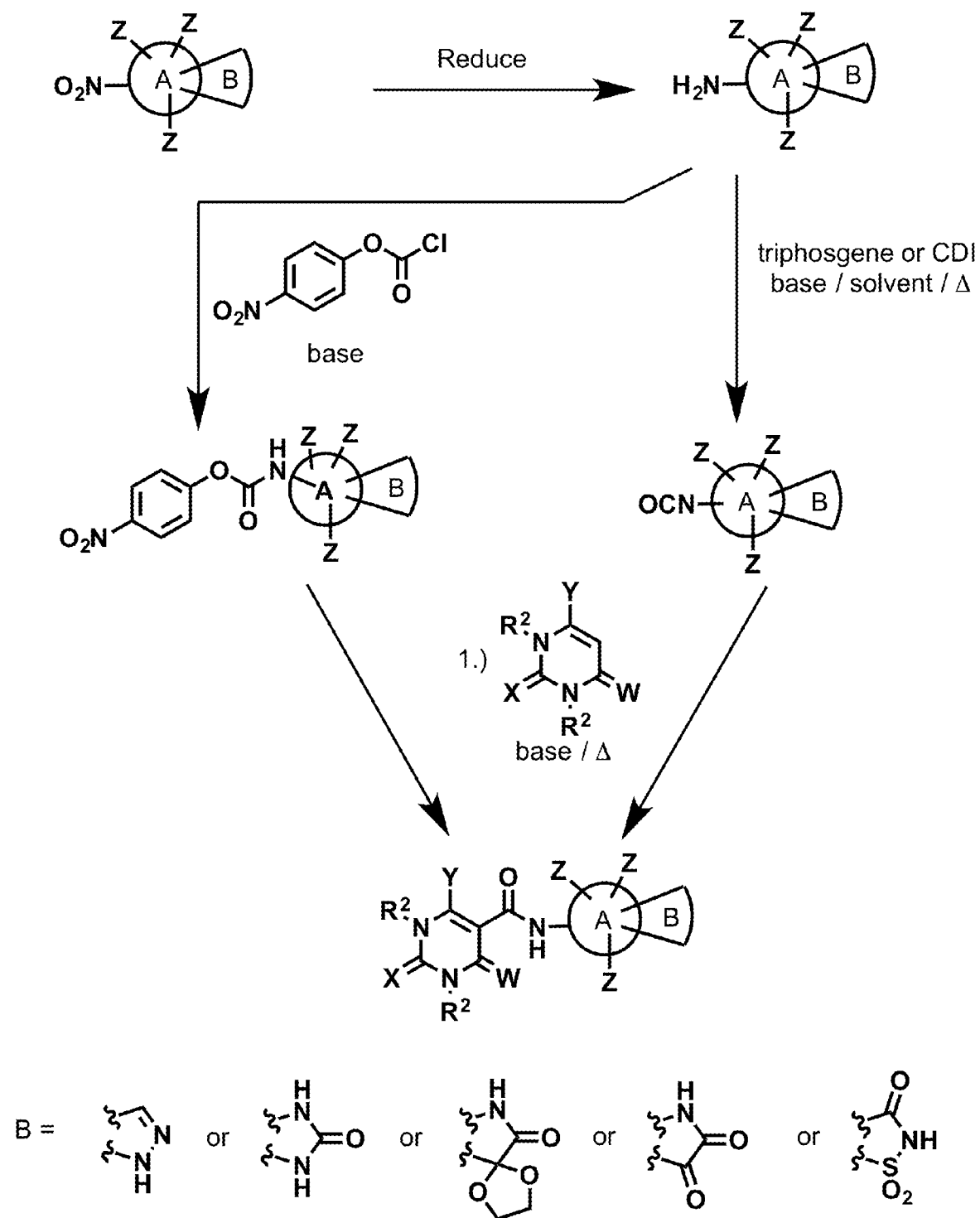
FIG. 5 illustrates a general scheme for synthesis of compounds containing a heterocycle fused onto the A ring.
Figure 6:
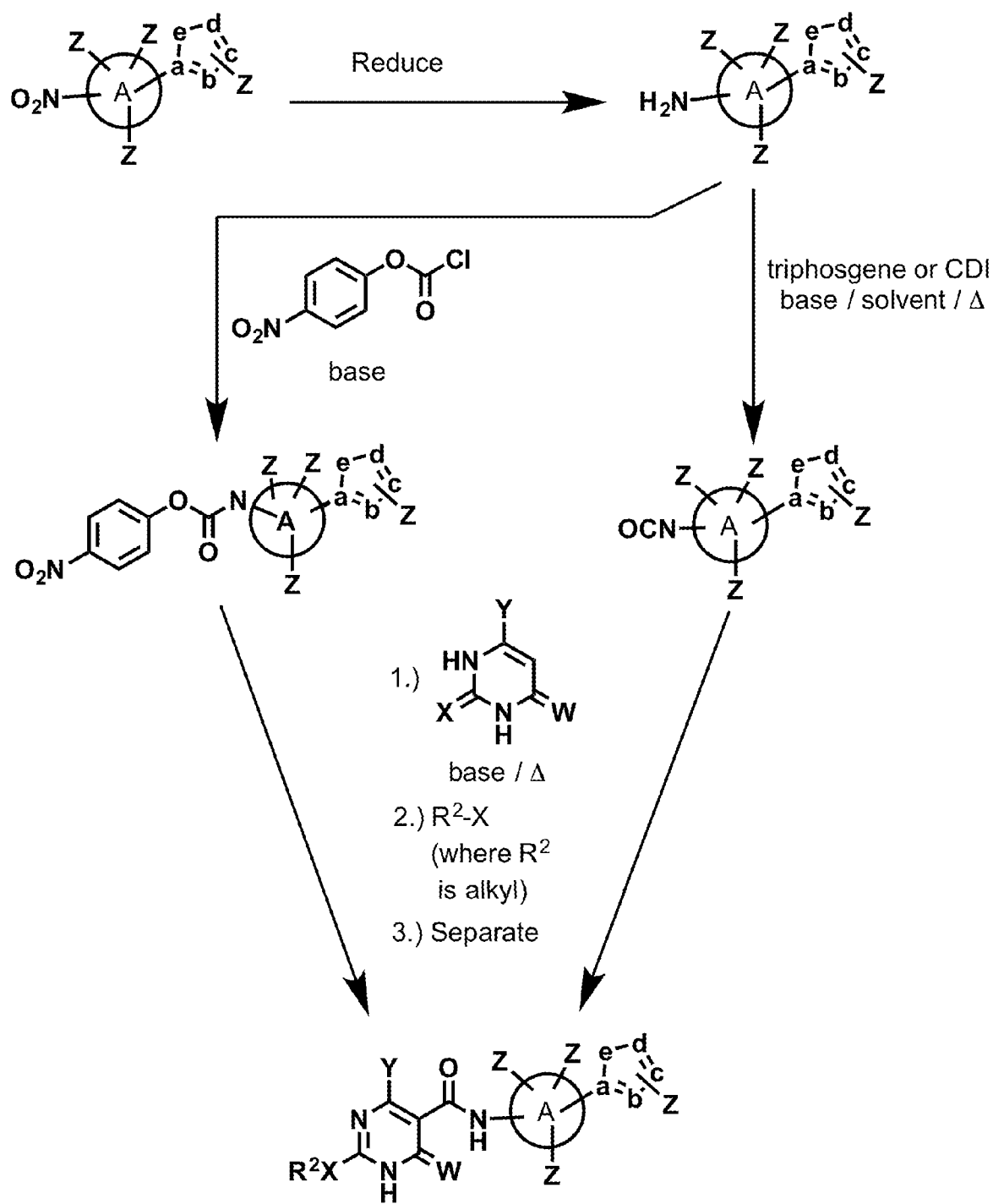
FIG. 6 illustrates a general scheme for synthesis of compounds containing a substituent on X of the barbiturate ring.
Figure 7:
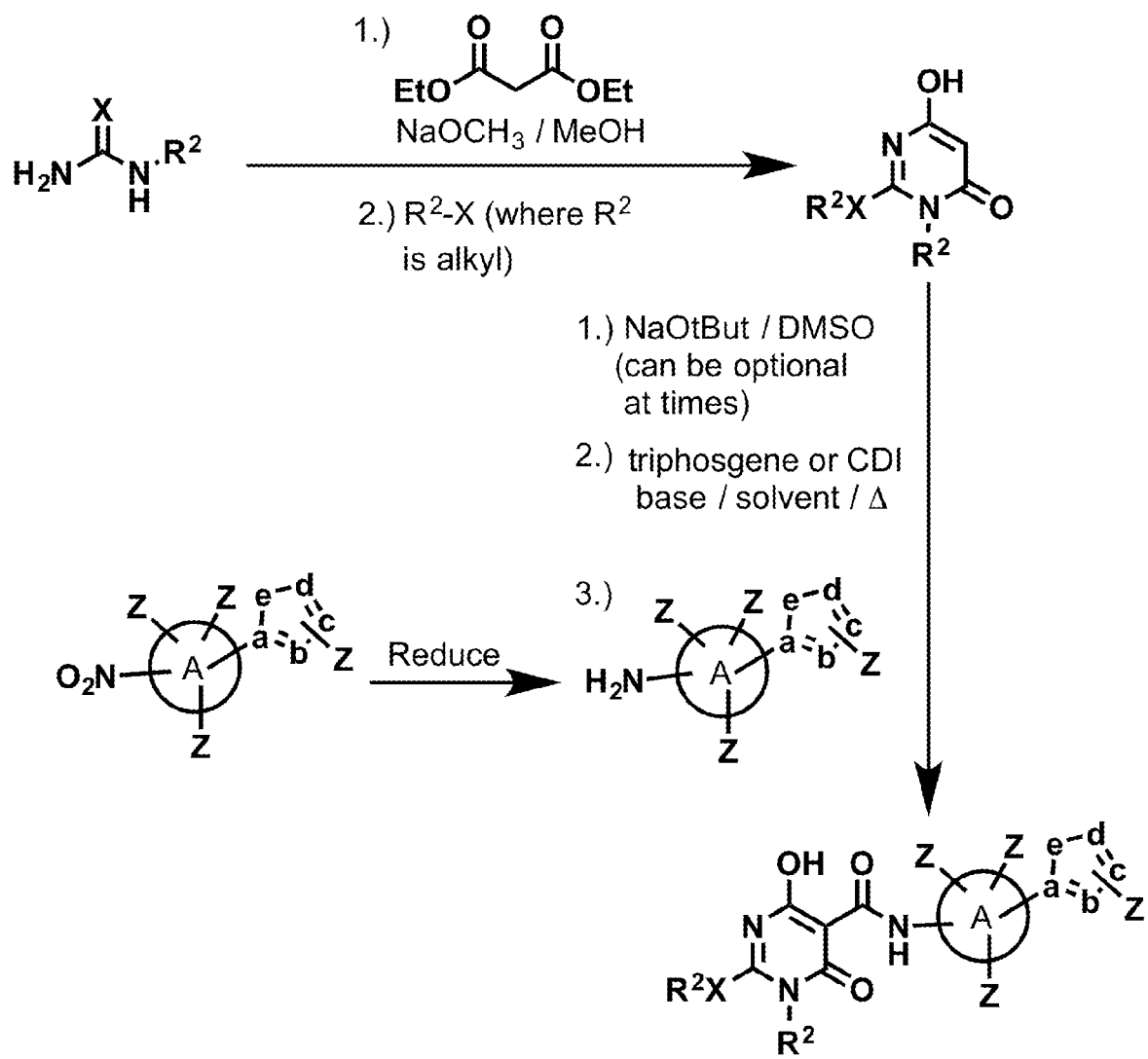
FIG. 7 illustrates an alternative general scheme for synthesis of compounds containing a substituent on X of the barbiturate ring.
Figure 8:
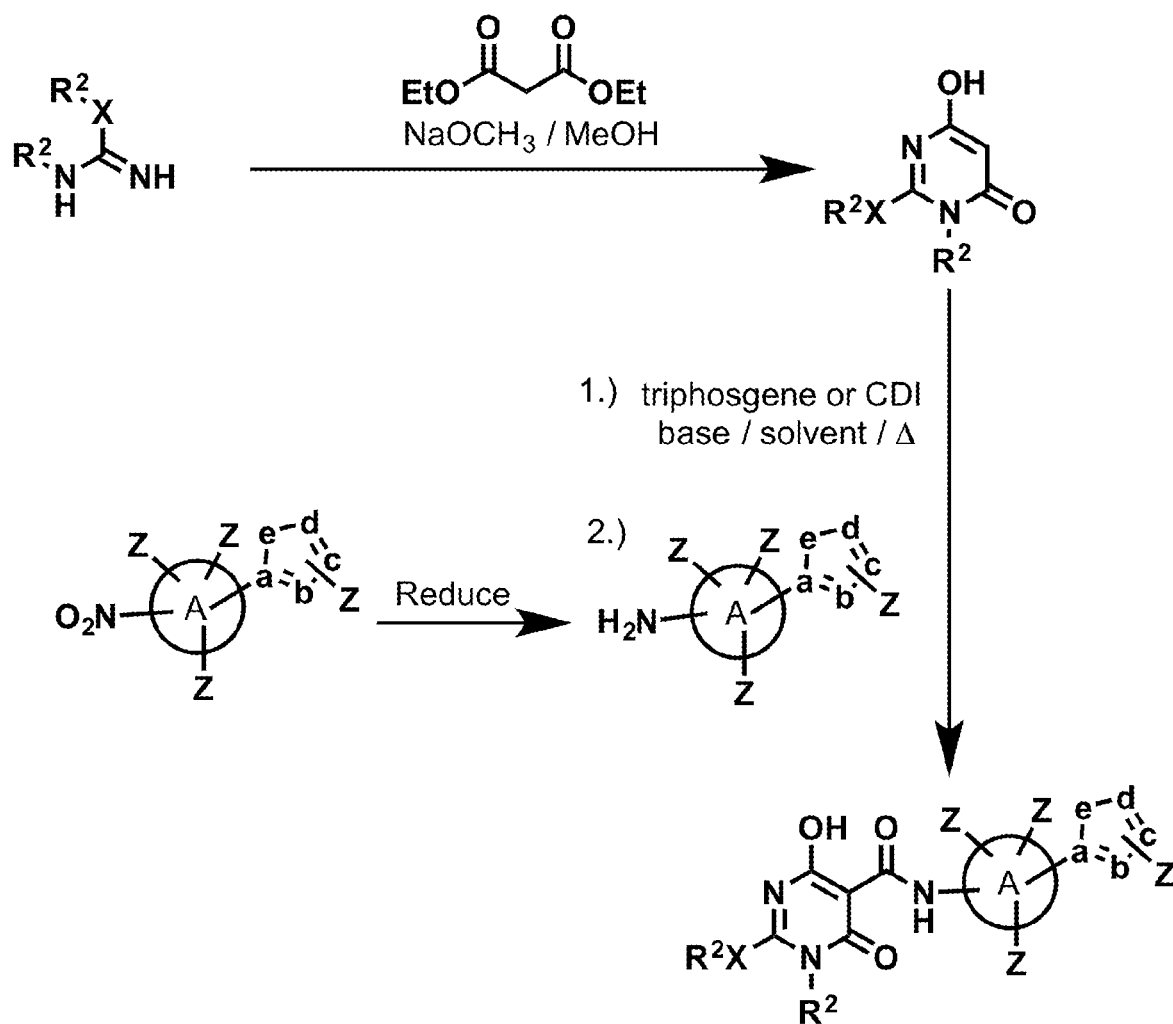
FIG. 8 illustrates a further alternative general scheme for synthesis of compounds containing a substituent on X of the barbiturate ring.
Figure 9:
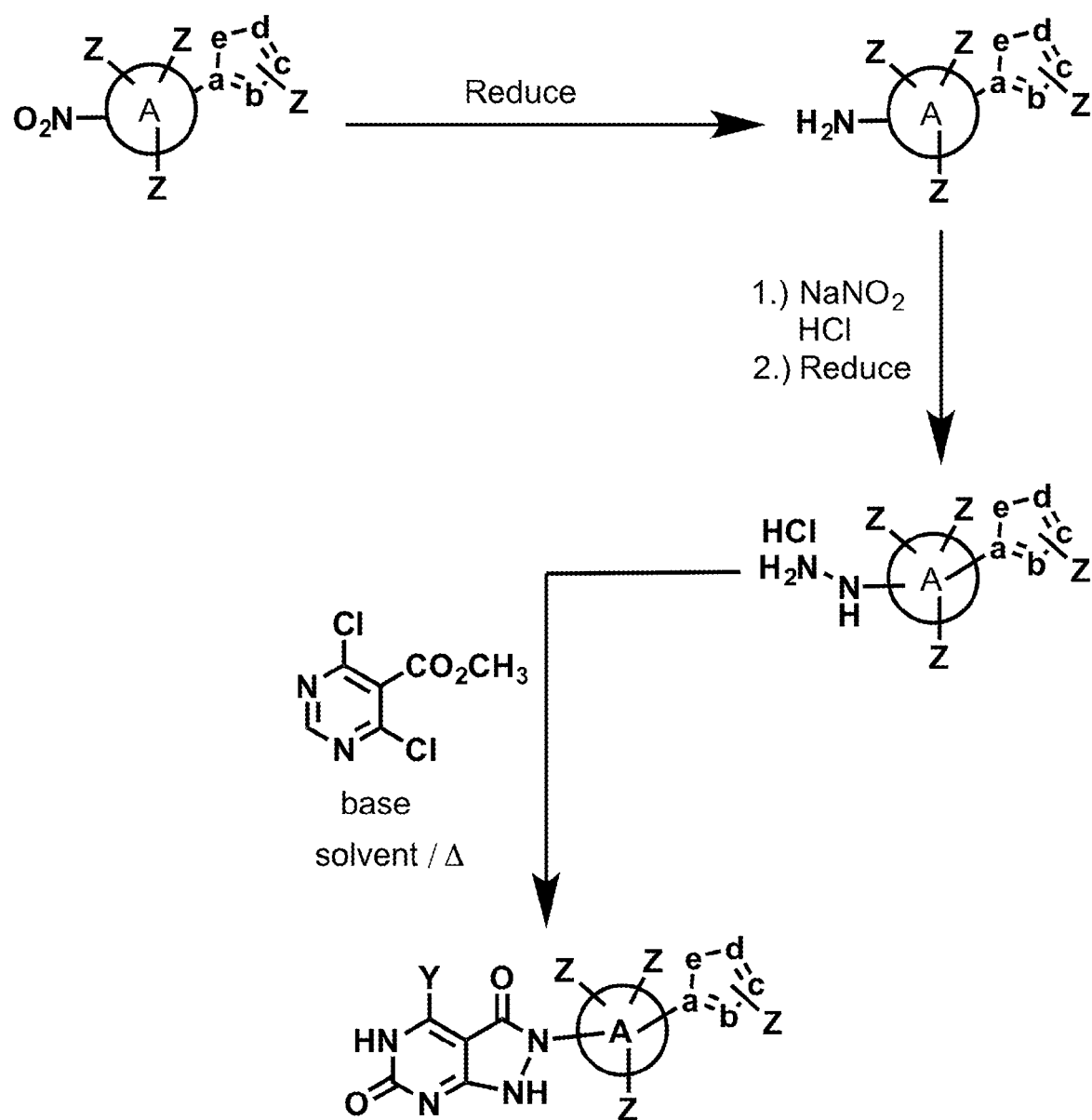
FIG. 9 illustrates an alternative general scheme for synthesis of bridged compounds.
Figure 10:
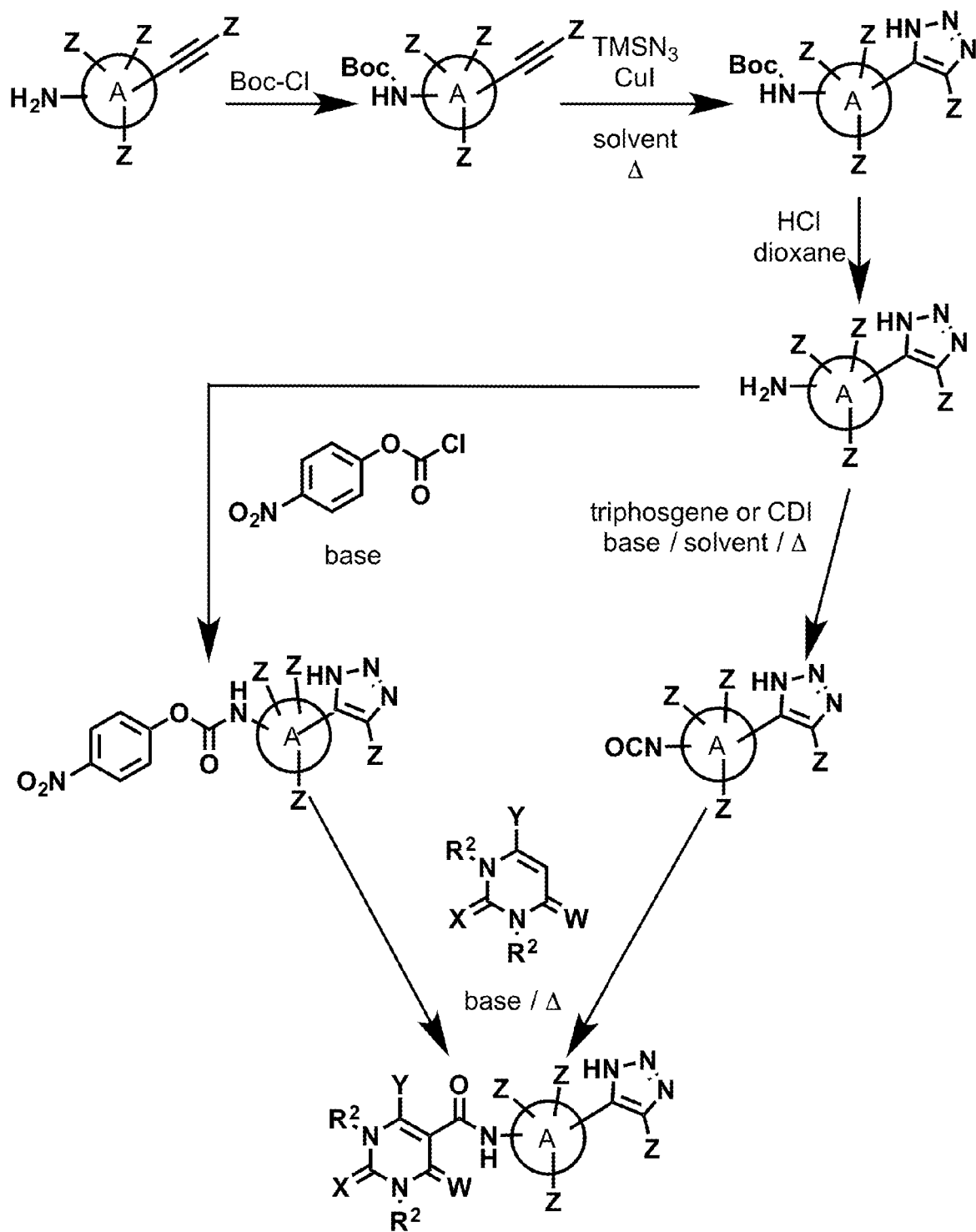
FIG. 10 illustrates a general scheme for synthesis of compounds containing a triazole heterocyclic ring.
Figure 11:
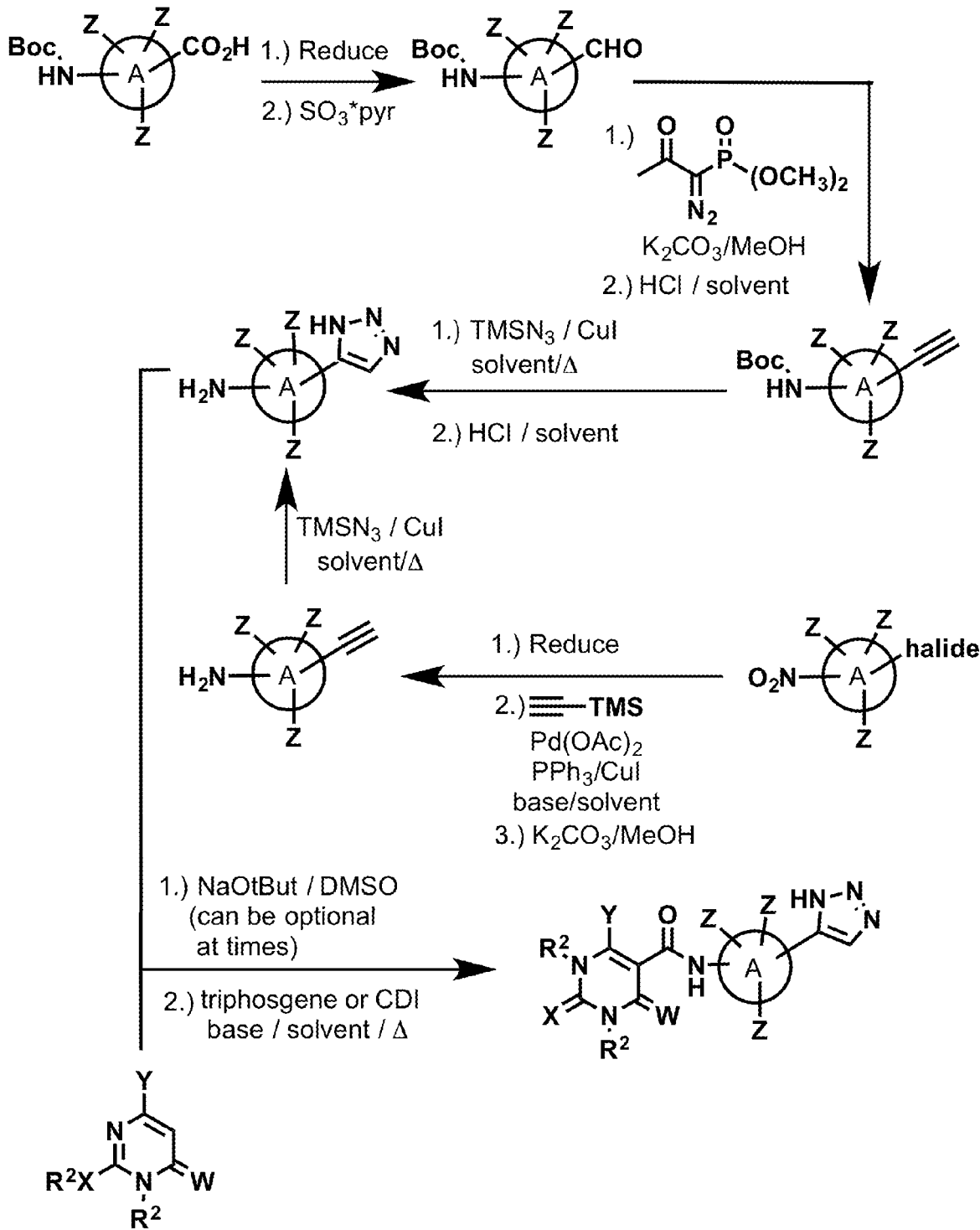
FIG. 11 illustrates alternative general schemes for synthesis of the A ring of the compounds.

The compounds disclosed herein can be synthesized various general procedures, as depicted in FIGS. 1-11. In general the various synthetic routes center on the coupling of a substituted phenyl, heterocyclic, cycloalkyl or spirocyclic A ring with an appropriately substituted barbiturate ring. Several different coupling agents can be employed in this process and the general procedures are described below in "General Procedure 1" or "General Procedure 2". Many of the compounds can be made as illustrated in FIG. 1, if the appropriately substituted nitro or amino ring A is known in the art. Variations to this sequence of steps are shown in FIGS. 2-11. The syntheses of certain bridged systems are illustrated in FIG. 2. This process requires the introduction of a ketene thio acetyl, wherein the sulfur substituents can then be displaced with various amines, like ring A containing an amino group, followed by a substituted hydrazine or hydroxylamine. Subsequent ring closure is accomplished by known procedures. FIG. 3 depicts another possible route to make certain of the compounds. This process centers on construction of the barbiturate ring at the end of the synthesis via treatment of a substituted malonate with a substituted urea or thiourea. FIG. 4 relates to synthesis of compounds that contain a hydroxamic acid in place of the heterocyclic ring. The process involves addition of a compound containing an ester on the A ring. This ester is then readily converted to a hydroxamic acid after coupling to the barbiturate ring via known procedures. FIG. 5 depicts the synthesis of compounds that contain a fused heterocycle on the A ring. In general the fused heterocycle is prepared with an amino group on the A ring and then it is coupled to the barbiturate ring as described above. FIGS. 6-8 depict methods of synthesis that result in compounds containing a substituent on X of the barbiturate ring. FIG. 6 is the most straightforward way of making such compounds, as it generally follows the sequence depicted in FIG. 1. However, this method involves a subsequent last step, which involves alkylation of the X group. This is only possible if R$^2$ is an alkyl group, and separation of the various possible isomers obtained may be necessary. The synthesis outlined in FIG. 7 is more direct in that it ensures that the R$^2$ group is attached to the barbiturate ring. This process involves the introduction of the R$^2$ group early in the synthesis, first by condensation of malonate to an appropriately substituted urea, followed by alkylation, which again is conducted with an alkyl halide (i.e., R$^2$ is alkyl). In certain cases, a protecting group may be necessary depending on the nature of the substituents. In another case the R$^2$ group on the X can be introduced in the earliest part of the synthesis. It can be intact on the substituted urea or thiourea. This would allow for compounds that contain an aryl or heterocyclic aryl group on X. This is depicted in FIG. 8 and involves the condensation of the R$^2$ substituted urea or thiourea with malonate. The subsequent barbiturate ring is then coupled to the appropriate amino A ring compound to produce the desired product. FIG. 9 depicts another variation of synthesis of the bridged compounds described in FIG. 2. It involves formation of a hydrazine A ring first, followed by condensation with methyl 4,6-dichloropyrimidine-5-carboxylate. Workup not only provides the cyclized bridged ring system, but also oxidizes the position adjacent to the two nitrogens on the pyrimidine ring. FIG. 10 depicts methods for forming the triazole heterocyclic ring when it is not known in the art. Addition of azide to an amino containing A ring can be accomplished via a variety of methods which all involve the addition of azide to the acetylene. Protecting groups as illustrated in the figure may be necessary. Sometimes the acetylene containing A ring may not be known in the art, so it needs to be synthesized. This can be accomplished via a variety of methods as illustrated in FIG. 11. Treatment of the corresponding aldehyde of the ring A compound with 1-diazo-1-((dimethylperoxy)(oxo)-λ$^4$-phosphanyl)propan-2-one, which is known in the art, or Sonogashira reaction on the halide of a ring A compound would produce the corresponding acetylenic A ring containing compound. Subsequent addition of azide to the acetylene would produce the triazole. This can then be coupled by the methods described above to produce the desired targeted compound.

In one aspect, the invention provides methods for reducing uric acid levels in the blood or serum of a subject comprising administering a compound having a structure represented by any of Formulae (I)—(VIII), or a combination thereof, to the subject in an amount effective to reduce blood or serum uric acid levels. It is to be understood that all such methods for reducing uric acid levels correspond to a compound having a structure represented by any of Formulae (I)—(VIII), or a combination thereof, for use in medicine as well as a compound having a structure represented by any of Formulae (I)—(VII), or a combination thereof, for use in the treatment of elevated uric acid levels. Typically, the compound having a structure represented by, or a combination thereof, will be administered when the level of uric acid in the blood of the subject is elevated, i.e., in the upper range of normal or above normal levels. One skilled in the art would further recognize that continued administration after normal uric acid levels are achieved is also contemplated in order to maintain uric acid levels within the normal range and to reduce the overall body burden of uric acid that may have occurred due to previously sustained hyperuricemia. Accordingly, methods for preventing elevation of uric acid levels in blood or serum are also an aspect of the invention. It is to be understood that all such methods for preventing elevation of uric acid levels correspond to a compound having a structure represented by any of Formulae (I)—(VIII), or a combination thereof, for therapeutic use as well as a compound having a structure represented by any of Formulae (I)—(VIII), or a combination thereof, for prevention of elevated uric acid levels.

Normal uric acid levels in blood are generally in the range of 4.3 mg/dL to 8.0 mg/dL. In certain embodiments, a compound having a structure represented by any of Formulae (I)—(VIII), or a combination thereof, is administered to a subject with a blood uric acid level of at least about 6 mg/dL. Administration may continue until a blood uric acid level of about 6.0 mg/dL or less is reached; however, it is generally considered to be beneficial to maintain uric acid levels below this target in patients with disorders of uric acid metabolism.

In certain embodiments, the invention provides methods of treating a disorder of uric acid metabolism caused by, or associated with, elevated uric acid levels in blood or serum (hyperuricemia). The method of treating such disorders comprises administering a compound having a structure represented by any of Formulae (I)—(VIII), or a combination thereof, to a subject in need thereof in an amount effective to reduce serum uric acid levels, thereby treating the disorder of uric acid metabolism in the subject. These disorders are associated with, or caused by, elevated uric acid levels in blood or serum which are in the upper range of normal or above normal, and include gout, hyperuricemia, kidney disease, arthritis, kidney stones, kidney failure, urolithiasis, plumbism, hyperparathyroidism, psoriasis, inborn genetic errors of metabolism (including but not limited to Lesch-Nyhan syndrome), sarcoidosis, cardiovascular disease (including but not limited to atherosclerosis), and transplantation of blood, bone marrow or solid organs. These drugs are particularly useful for treating gout and kidney disease (including acute uric acid nephropathy, chronic urate nephropathy, and uric acid nephrolithiasis). In addition, treatment of some cancers with chemotherapy leads to the release of large amounts of uric acid into the blood, which can damage the kidneys. Chemotherapy-induced hyperuricemia, particularly the disorder known as "tumor lysis syndrome," may also be treated, prevented or ameliorated according to the methods of the invention. Administration of a compound having a structure represented by any of Formulae (I)—(VIII), or a combination thereof, to a subject with hyperuricemia, such as a subject suffering from gout, kidney disease, or a risk of inducing elevated uric acid levels due to chemotherapy, treats, prevents or ameliorates these disorders by reducing uric acid levels in blood, or preventing or controlling their level of increase. In specific embodiments, the disorder of uric acid metabolism treated by administration of a compound having a structure represented by any of Formulae (I)—(VIII), a combination thereof, is gout. It is to be understood that all such methods for treating disorders of uric acid metabolism caused by, or associated with, elevated uric acid levels in blood or serum (hyperuricemia) correspond to a compound having a structure represented by any of Formulae (I)—(VIII), or a combination thereof, for therapeutic use as well as a compound having a structure represented by any of Formulae (I)—(VIII), or a combination thereof, for treatment of disorders of uric acid metabolism caused by, or associated with, elevated uric acid levels in blood or serum.

The dose of a compound having a structure represented by any of Formulae (I)—(VIII), or a combination thereof, administered to the subject may be any dose sufficient to achieve a desired reduction in uric acid levels in blood or serum over the time-course of administration. In certain embodiments, a daily dose of about 20 to about 1,500 mg/m$^2$/day is administered. In other embodiments, a daily dose of about 20 to about 500 mg/m$^2$/day, about 20 to about 250 mg/m$^2$/day, about 20 to about 150 mg/m$^2$/day or about 20 to about 100 mg/m$^2$/day is administered. In other embodiments, a daily dose of about 50 to about 1,500 mg/m$^2$/day is administered. In other embodiments, a daily dose of about 50 to about 500 mg/m$^2$/day, about 50 to about 150 mg/m$^2$/day, about 50 to about 100 mg/m$^2$/day, or about 20 to about 100 mg/m$^2$/day is administered.

In certain embodiments of any of the foregoing methods, a compound having a structure represented by any of Formulae (I)—(VIII), or a combination thereof, is administered to the subject parenterally, intraperitoneally, intravenously, intranasally, intrarectally, or orally. Particularly useful routes of administration include injection, infusion, or oral administration. The amount of the drug administered per dose is an amount sufficient to achieve a reduction in uric acid levels in blood or serum, to prevent elevation of uric acid levels in blood or serum, or to treat or prevent a disorder of uric acid metabolism over the course of therapy. One skilled in the art will recognize that individualization of dosage based on a patient's body composition or his/her hypouricemic response to treatment may be medically necessary or desirable.

The drug(s) may be administered to the subject either intermittently or continuously over a period of time in order to achieve the desired reduction in uric acid levels in blood or serum, or to treat a disorder of uric acid metabolism. For example, doses may be administered intermittently several times per day, daily, once, twice or three times per week, or at monthly intervals. In a specific example, a compound having a structure represented by any of Formulae (I)—(VIII), or a combination thereof, may be administered to the subject by continuous intravenous infusion over 24 hours for about five days. Alternatively, a compound having a structure represented by any of Formulae (I)—(VIII), or a combination thereof, may be administered to the subject by intravenous infusion over about 1 hour to about 5 hours for about five consecutive days. In a specific example, a compound having a structure represented by any of Formulae (I)—(VIII), or a combination thereof, may be administered to the subject by intramuscular injection or by intravenous infusion over about 10 minutes for about five consecutive days. In further specific embodiments, a compound having a structure represented by any of Formulae (I)—(VIII), or a combination thereof, may be administered to the subject by daily bolus injections for about five days. The period of time of administration in any of the foregoing protocols may be modified to achieve the desired reduction in uric acid levels, including about 2 days, about 3 days, about 4 days, about one week or about two weeks of administration, or for longer periods in repeated treatment cycles, and these treatments may be repeated at intervals of every two to every 10 weeks.

In addition to continuous intravenous infusion or bolus intravenous or subcutaneous injection, a compound having a structure represented by any of Formulae (I)—(VIII), or a combination thereof, may be administered to the subject orally. In this embodiment, an oral dose in amounts as described above may be administered in one, two, three or four administrations per day for 1, 2, 3, 4, or 5 days to achieve the desired reduction in uric acid levels. In further embodiments, the oral dose as described above may be administered once per day, or in one, two, three or four administrations per day for one week or two weeks, to achieve the desired reduction in uric acid levels.

It will be appreciated that a subject in need of reduced levels of uric acid in blood or serum, or in need of treatment of a disorder of uric acid metabolism, will be treated more aggressively initially to achieve the desired reduction in uric acid levels. Following initial therapy and reduction of uric acid levels to normal or sub-normal levels, the subject may be further treated over a period of time, or over a lifetime, to maintain normal or sub-normal levels of uric acid in blood or serum and prevent elevation of uric acid levels subsequent to the initial treatment. The maintenance or preventive protocol may comprise reduced dosages and/or less frequent administration of a compound having a structure represented by any of Formulae (I)—(VIII), or a combination thereof, as necessary or desired to maintain normal or sub-normal uric acid levels in blood or serum. For example, in a maintenance protocol the drug(s) may be administered daily, weekly, monthly, or intermittently as uric acid levels rise between treatment periods. Such maintenance protocols will serve to maintain normal or sub-normal uric acid levels for a prolonged period of time and reduce the subject's lifetime risk of developing a disorder of uric acid metabolism caused by, or associated with, prolonged hyperuricemia. The initial reduction of uric acid levels from above normal or high normal to normal or sub-normal, and maintenance of normal or sub-normal uric acid levels are both features included in treatment of a disorder of uric acid metabolism. It is anticipated that in certain embodiments, a typical patient will require daily treatment of varying duration, and that such daily treatment may be provided intermittently for life or for extended periods.

In certain embodiments of any of the foregoing methods, blood or serum uric acid levels of the subject are reduced by at least 25% compared to uric acid levels prior to administration of a compound having a structure represented by any of Formulae (I)—(VIII), or a combination thereof. In certain further embodiments, blood or serum uric acid levels of the subject are reduced by 50% or more compared to levels prior to administration. In a specific embodiment, uric acid levels are reduced by about 75% even at daily doses of 500 mg/m$^2$/day or less.

In a second aspect of the invention methods are provided for treating a disorder of uric acid metabolism associated with, or caused by, elevated uric acid in blood or serum comprising administering to a subject in need thereof a compound having a structure represented by any of Formulae (I)—(VIII), or a combination thereof, in an amount effective to reduce blood or serum uric acid levels, thereby treating the disorder of uric acid metabolism. Specific embodiments of the methods for treating a disorder of uric acid metabolism relating to dosing, routes of administration, initial therapy and maintenance therapy are as described above for reducing uric acid levels in blood or serum. The initial reduction in uric acid levels is typically rapid, and often occurs within 1-3 days. Upon reduction in uric acid levels to normal or sub-normal levels, continued maintenance or preventive therapy results in a detectable improvement in at least one symptom of elevated uric acid, for example reduced inflammation, reduced pain, slowing of development of deformities, reduced development of kidney stones, prevention of tumor lysis syndrome, stabilization in cognition or other manifestations of inborn metabolic disorders, or improvement in (or reduction of actual or risk for) cardiovascular disease. One skilled in the art will recognize that prevention of recurrent symptoms of disease due to recurrence of elevated serum uric acid levels, thereby necessitating extended treatment, would be highly desirable to maximize patient benefit.

In embodiments corresponding to the foregoing methods, the invention relates to use of a compound disclosed herein, or a combination thereof, for reducing uric acid levels in blood or serum of a subject in need thereof, preventing elevation of uric acid levels in blood or serum of a subject, or treating a disorder of uric acid metabolism caused by, or associated with, hyperuricemia. Each of the methods of treatment or prevention disclosed, including routes of administration, dosage and compounds administered, are also applicable to such uses of the compounds.

A further aspect of the invention provides a pharmaceutical composition comprising a compound having a structure represented by any of Formulae (I)—(VIII), or a combination thereof, and a pharmaceutically acceptable carrier. In certain embodiments of the pharmaceutical compositions, the composition is formulated as a solution or tablet. Solutions or dispersions of the drug(s) can be prepared in water or saline. In certain embodiments of the pharmaceutical compositions, the pharmaceutically acceptable carrier is one or more component selected from the group consisting of one or more of a solvent, a dispersing agent, a coating (e.g., lecithin), a surfactant (e.g., hydroxypropylcellulose), a preservative (e.g., paraben, phenol, thimerosal, sorbic acid, chlorobutanol), an emulsion, an alcohol (e.g., ethanol), a polyol (e.g., glycerol, propylene glycol), and an isotonic agent (e.g., sugars, sodium chloride).

In certain embodiments of the foregoing pharmaceutical compositions, the composition is formulated for controlled release of the compound having a structure represented by any of Formulae (I)—(VIII), or a combination thereof. In certain embodiments of the foregoing methods, a compound having a structure represented by any of Formulae (I)—(VIII), or a combination thereof, is administered in a form for controlled release. The controlled release compositions may include pharmaceutically acceptable carriers or excipients which cause release of the active ingredient more slowly or which extend the duration of its action within the body. Examples of controlled release compositions include pharmaceutically acceptable carriers or excipients which delay absorption of the active ingredient (e.g., aluminum monostearate, gelatin, natural or synthetic hydrophilic gums). Alternatively, controlled release of the pharmaceutical composition may employ a device such as a pump, implant or transdermal patch.

In certain embodiments of the foregoing pharmaceutical compositions, the composition is formulated for improved oral bioavailability or extended release in the body. For example, microemulsions, particle size reduction and complexation technologies may be used to improve dissolution rates or equilibrium solubilities of the compounds. Other suitable chemical and physical means for improving oral bioavailability or extended release will also be known to those skilled in the art.

EXAMPLES

General Procedure for carbonyldiimidazole (CDI) Coupling (General Procedure 1): To a stirring solution of amine (1 eq) in anhydrous DMSO (1.0 M) was added 1,1'carbonyldiimidazole (1.5 eq) at rt, under inert atmosphere. The resulting solution was stirred for 20 min at rt. In a separate flask containing barbituric acid (1 eq) was added anhydrous 1,4-dioxane (0.30 M), then heated to 55° C. Et$_3$N (1.6 eq) was added and stirred for 15 min at 55° C. The isocyanate generated from the amine in DMSO was added to the stirring suspension, then heated to 80° C. until complete consumption of the starting materials were observed via LCMS (1-20 h). The reaction mixture was cooled to rt, then acidified with 6M HCl (aq), the precipitate formed was isolated, then triturated with water, MeOH, followed by acetonitrile.

General Procedure for Triphosgene coupling (General Procedure 2): 2-(Methylthio)pyrimidine-4,6-diol (2 eq) was added to a stirring solution of sodium tert-butoxide (2.0 eq) dissolved in DMSO (0.2 M) at rt for 5 min. In a separate flask, amine was dissolved in 1,4-dioxane (0.8 M), to this solution was added triphosgene (0.33 eq) in one-portion. The suspension was stirred vigorously for 2 min at rt, then iPr$_2$NEt (2 eq) was added. The suspension was stirred vigorously at rt for 2 min. Freshly prepared solution of sodium 6-hydroxy-2-(methylthio)pyrimidin-4-olate in DMSO was added to the suspension in one-portion. The reaction was stirred at 90° C. for 30 min, until complete consumption of starting material observed via LCMS. The reaction mixture was loaded directly on C18 column and purified via reverse-phase chromatography.

Figure 12:
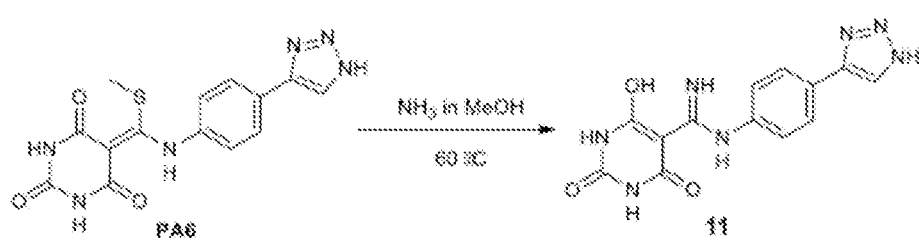
FIG. 12 illustrates a synthesis scheme for a compound having a structure represented by Formula ($I_a$), as described in Example 1.

Example I: Preparation of N-(4-(1H-1,2,3-triazol-4-yl)phenyl)-6-hydroxy-2,4-dioxo-1,2,3,4-tetrahydropyrimidine-5-carboximidamide (11, Formula (I$_a$), with Reference to FIG. 12)

5-((4-(1H-1,2,3-triazol-4-yl)phenylamino)(methylthio)methylene)pyrimidine-2,4,6(1H,3H,5H)-trione (PA6) (48 mg, 0.140 mmol) was added a solution of 7.0 M NH$_3$ in methanol (1.0 mL) at rt. The reaction was sealed and heated to 60° C., until complete consumption of the starting material was observed via LCMS (20 h). The reaction mixture was allowed to cool to rt, the precipitate formed was filtered and washed with acetonitrile, then the solid was lyophilized to yield the product (11) as an off-white solid (39 mg, 99.5% purity, 89% yield).

$^1$H NMR (500 MHz, DMSO-d6+DCl in D$_2$O) δ 8.49 (s, 1H), 7.92-7.87 (m, 2H), 7.32-7.28 (m, 2H).

LCMS: m/z [M+1]+=314.09; R$_T$=0.93 min; purity=99.5%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 13:
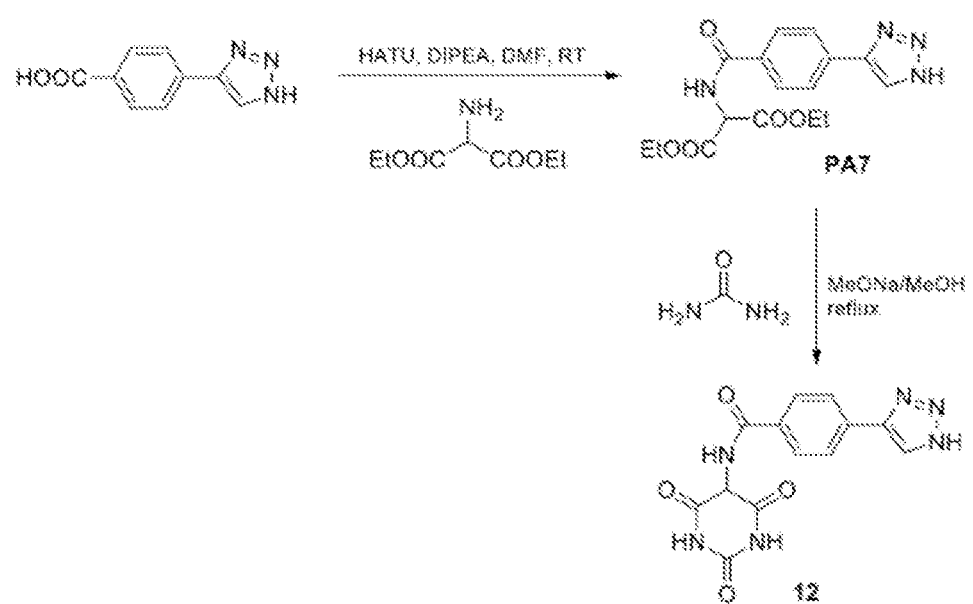
FIG. 13 illustrates a synthesis scheme for a compound having a structure represented by Formula ($I_1$), as described in Example 2.

Example 2: Preparation of 4-(1H-1,2,3-triazol-4-yl)-N-(2,4,6-trioxohexahydropyrimidin-5-yl)benzamide (12, Formula (I$_1$, with Reference to FIG. 13)

Step One. Diethyl 2-(4-(1H-1,2,3-triazol-4-yl)benzamido)malonate (PA7). 4-(1H-1,2,3-triazol-4-yl)benzoic acid (76 mg, 0.41 mmol, prepared as described, in: Jin, T.; Kamijo, S.; Yamamoto, Y. Eur. J. Org. Chem. 2004, 3789-3791), 2-amino-diethyl malonate HCl salt (106 mg, 0.48 mmol) and HATU (183 mg, 0.483 mmol) was sequentially added into DMF (2 mL), iPr$_2$NEt (156 mg, 1.2 mmol) was added to the mixture and the reaction was stirred at rt for 1 h. The reaction mixture poured into water (20 mL) and the product was extracted with EtOAc (20 mL). The organic layer was washed with water (20 mL) and brine (10 mL), dried over MgSO$_4$, then concentrated in vacuo. The product was purified via ISCO (0% to 10% MeOH in CH$_2$Cl$_2$) to yield the product (120 mg, 86% yield).

Step Two. 4-(1H-1,2,3-triazol-4-yl)-N-(2,4,6-trioxohexahydropyrimidin-5-yl)benzamide (12). Diethyl 2-(4-(1H-1,2,3-triazol-4-yl)benzamido)malonate (PA7) (356 mg, 1.03 mmol) and urea (50 mg, 0.82 mmol) dissolved in MeOH (10 mL). To the solution was added NaOMe (0.55 mL, 30% in MeOH). The mixture was refluxed overnight. To the reaction was added formic acid until neutral. The solvent was removed in vacuo and the crude was dissolved in DMSO (2 mL). The crude product was purified via ISCO (C18, 5 to 100% acetonitrile in water, with an ammonium formate buffer 10 mM, over 15 CV gradient) to yield the product (12) as an off-white solid (62.0 mg, 97.7% purity, 19.2% yield), after lyophillization.

$^1$H NMR (500 MHz, CDCl$_3$+DCl in D$_2$O) δ 8.52 (s, 1H), 8.06-7.99 (m, 4H).

LCMS: m/z [M−H]$^-$=315.10; R$_T$=0.74 min; purity=97.7%.

HPLC conditions: Column: XTerra RP18, 3.5 μm, 3.0×50 mm; Gradient: 5% B for 0.3 min, 5% to 100% B in 4.5 minutes; 100% B for 2.2 minute; 1 mL/min; 7 min run. Eluent A: Milli-Q H$_2$O+0.1% Formic Acid; Eluent B: Acetonitrile+0.1% Formic Acid.

Figure 14:
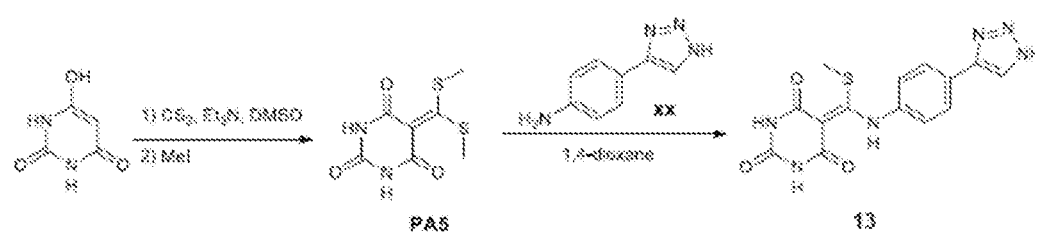
FIG. 14 illustrates a synthesis scheme for a compound having a structure represented by Formula ($I_b$), as described in Example 3.

Example 3: Preparation of 5-(((4-(1H-1,2,3-triazol-5-yl)phenyl)amino)(methylthio)methylene)pyrimidine-2,4,6(1H,3H,5H)-trione (Formula (I$_b$), with Reference to FIG. 14)

Step One. 5-(Bis(methylthio)methylene)pyrimidine-2,4,6 (1H,3H,5H)-trione (PA5). A mixture of barbituric acid (2.5 g, 21.4 mmol), triethylamine (4.3 g, 42.7 mmol), and carbon disulfide (1.6 g, 21.4 mmol) was allowed to stir at rt until complete consumption of the starting material was observed via LCMS (0.5 h). The resulting reaction mixture was cooled in an ice-bath, iodomethane (6.1 g, 42.7 mmol) was added in one-portion, the reaction was then allowed to warm up to rt over 3 h. The reaction mixture was poured into water (150 mL) with rapid stirring, then allowed to stand for 1 h. The precipitate formed was filtered, washed with water and acetone. The precipitate was collected and dried under high vacuum to yield the product as a yellow solid (750 mg, 15.1% yield).

Step Two. 5-(((4-(1H-1,2,3-Triazol-4-yl)phenyl)amino)(methylthio)methylene)pyrimidine-2,4,6(1H,3H,5H)-trione (13). A mixture of PA5 (76.9 mg, 0.331 mmol) and XX (53 mg, 0.331 mmol) in anhydrous 1,4-dioxane (5 mL) was sealed in a microwave vessel and heated to 100° C. for 30 min, complete consumption of the starting material was observed via LCMS. Evaporate the solvent in vacuo and dissolved the crude in DMSO. ISCO purification (C18, 10 mM AmF in water/MeCN) was performed to yield the product (13) as a solid (49 mg, 95.6% purity, 43% yield), after lyophilization.

$^1$H NMR (500 MHz, DMSO) δ 8.41 (s, 1H), 7.96 (d, J=8.6 Hz, 2H), 7.46 (dd, J=8.5, 2.6 Hz, 2H), 2.09 (s, 3H).

LCMS: m/z [M+1]⁺=343.08; R$_T$=3.29 min; purity=95.6%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 15:
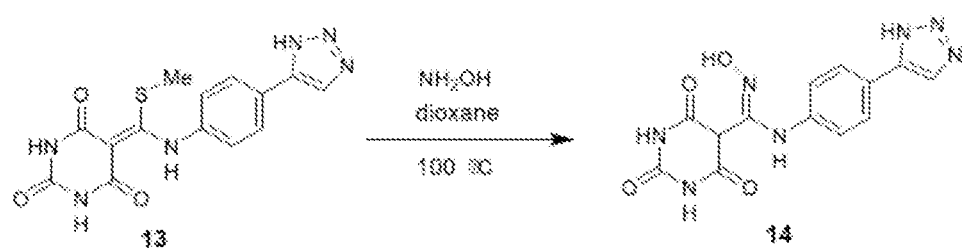
FIG. 15 illustrates a synthesis scheme for a compound having a structure represented by Formula ($I_c$), as described in Example 4.

Example 4: Preparation of (E)-N-(4-(1H-1,2,3-triazol-5-yl)phenyl)-N'-hydroxy-2,4,6-trioxohexahydro-pyrimidine-5-carboximidamide (14, Formula (I$_c$), with Reference to FIG. 15)

5-(((4-(1H-1,2,3-triazol-5-yl)phenyl)amino)(methylthio)methylene)pyrimidine-2,4,6(1H,3H,5H)-trione 13 (180 mg, 0.60 mmol) and hydroxylamine (400 uL, 6.0 mmol, 50% in water) were added into 1,4-dioxane (10 mL). The reaction was heated to 100° C. for 30 min. The solvent was removed in vacuo and the crude mixture was dissolved in DMSO (2 mL). The crude product was purified via ISCO (C18, 5 to 100% acetonitrile in water, with an ammonium formate buffer 10 mM, over 15 CV) to yield the product (14) as a yellow solid (41 mg, 94.0% purity, 24% yield), after lyophillization.

LCMS: m/z [M−1]⁻=328.07; R$_T$=2.90 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 16:
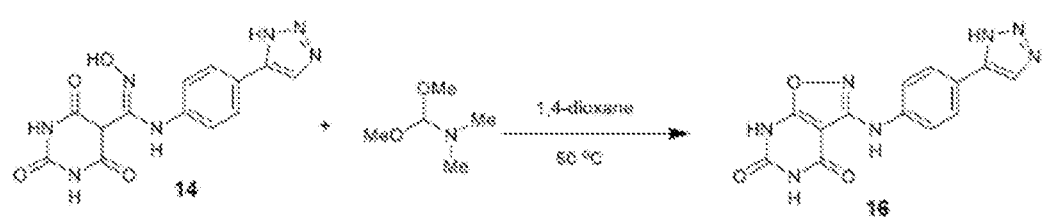
FIG. 16 illustrates a synthesis scheme for a compound having a structure represented by Formula ($VI_a$), as described in Example 5.

Example 5: Preparation of 3-((4-(1H-1,2,3-triazol-5-yl)phenyl)amino)isoxazolo[5,4-d]pyrimidine-4,6(5H,7H)-dione (16, Formula (VI$_a$), with Reference to FIG. 16)

Compound 14 (100 mg, 0.30 mmol) and DMFDMA (108 mg, 0.92 mmol) was added into anhydrous 1,4-dioxane (6 mL). The reaction mixture was heated up at 50° C. After 30 min, another portion of DMFDMA (108 mg, 0.92 mmol) was added to the reaction mixture. Reaction was stirred at the same temperature for an additional 30 min. The solvent was removed and the crude product was dissolved in DMSO (2 mL) and purified via Prep HPLC separation (0 to 100% acetonitrile in water with 10 mM ammonium formate buffer, over 10 min) to yield the product (16) as a white solid (24 mg, 99.5% purity, 28% yield), after lyophillization.

¹H NMR (500 MHz, d⁶-DMSO+DCl) δ 8.29 (s, 1H), 7.84 (d, J=8.9 Hz, 2H), 7.71 (d, J=8.9 Hz, 2H).

LCMS: m/z [M−1]⁻=310.11; R$_T$=3.23 min; purity=99.5%

HPLC conditions: Waters XTerra RP18 3.5 μm, 3.0×50 mm; hold 5% B for 1.0 minute, 5% to 95% B in 5.0 minutes, then hold 5% B for 1.0 minute, run time=7.0 min; Eluents: A=0.1% HCO$_2$H in water; B=0.1% HCO$_2$H in MeCN.

Figure 17:
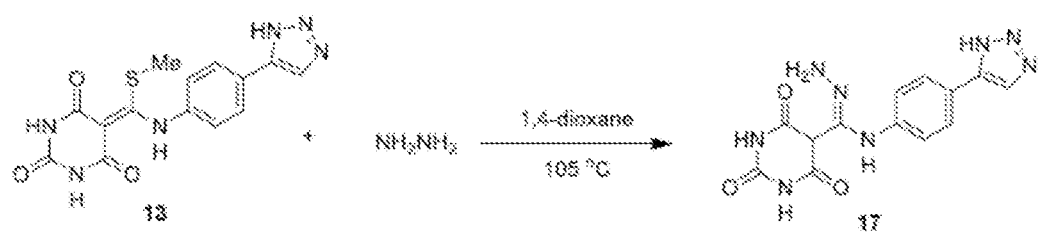
FIG. 17 illustrates a synthesis scheme for a compound having a structure represented by Formula ($I_d$), as described in Example 6.

Example 6: Preparation of (E)-N-(4-(1H-1,2,3-triazol-5-yl)phenyl)-2,4,6-trioxohexahydropyrimidine-5-carbohydrazonamide (17, Formula (I$_d$), with Reference to FIG. 17)

Compound 13 (100 mg, 0.33 mmol) and hydrazine hydrate solution (165 μL, 3.3 mmol, 55% in H$_2$O) was added into 1,4-dioxane (10 mL, dry) sequentially. The reaction was heated to 105° C. for 30 min. The precipitate was filtered to yield the product (17) as a beige solid (180 mg, 96.8% purity, 83% yield).

¹H NMR (500 MHz, d⁶-DMSO+DCl In D$_2$O) δ 10.68 (s, 1H), 8.37 (s, 1H), 7.84 (d, J=8.6 Hz, 2H), 7.27 (d, J=8.6 Hz, 2H),

LCMS: m/z [M−1]⁻=327.22; R$_T$=2.50 min; purity=96.8%.

HPLC conditions: Waters XTerra RP18 3.5 μm, 3.0×50 mm; hold 5% B for 1.0 minute, 5% to 95% B in 5.0 minutes, then hold 5% B for 1.0 minute, run time=7.0 min; Eluents: A=0.1% HCO$_2$H in water; B=0.1% HCO$_2$H in MeCN.

Figure 18:
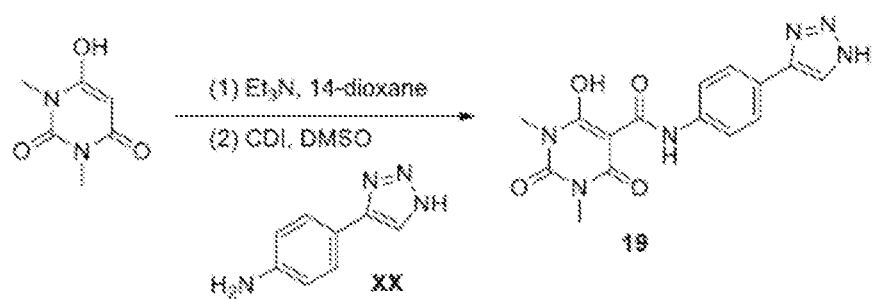
FIG. 18 illustrates a synthesis scheme for a compound having a structure represented by Formula ($I_e$), as described in Example 7.

Example 7: Preparation of N-(4-(1H-1,2,3-triazol-4-yl)phenyl)-6-hydroxy-1,3-dimethyl-2,4-dioxo-1,2,3,4-tetrahydropyrimidine-5-carboxamide (19, Formula (I$_e$), with Reference to FIG. 18)

Compound 19 was synthesized following general procedure 1. To a stirring solution of XX (27 mg, 0.169 mmol) in anhydrous DMSO (170 μL) was added 1,1'carbonyldiimidazole (41 mg, 0.254 mmol) was added at rt, under inert atmosphere. The resulting solution was stirred for 20 min at rt. In a separate flask containing 1,3-dimethylbarbituric acid (23 mg, 0.169 mmol) was added anhydrous 1,4-dioxane (506 μL), then heated to 50° C. Et$_3$N (37 μL, 0.27 mmol) was added and stirred for 15 min at 50° C. The isocyanate generated from XX in DMSO was added to the stirring suspension, then heated to 80° C. until complete consumption of the starting materials were observed via LCMS (1 h). The reaction mixture was cooled to rt, then acidified with 6M HCl (aq), the precipitate formed was isolated, then triturated with MeOH, followed by acetonitrile, to yield the product (19) as an off-white solid (5.6 mg, 97.8% purity, 4% yield).

¹H NMR (500 MHz, DMSO-d⁶) δ 8.29 (s, 1H), 7.88 (s, 2H), 7.66 (d, J=8.8 Hz, 2H), 3/24 (s. 6H).

LCMS: m/z [M+1]⁺=343.57; R$_T$=2.51 min; purity=97.8%.

HPLC conditions: Column: XTerra RP18, 3.5 μm, 3.0×50 mm; Gradient: 5% to 100% B in 2.5 minutes; 100% B for 1 minute; 1 mL/min; 4 min run. Eluent A: Milli-Q H$_2$O+ 0.1% Formic Acid; Eluent B: Acetonitrile+0.1% Formic Acid.

Figure 19:
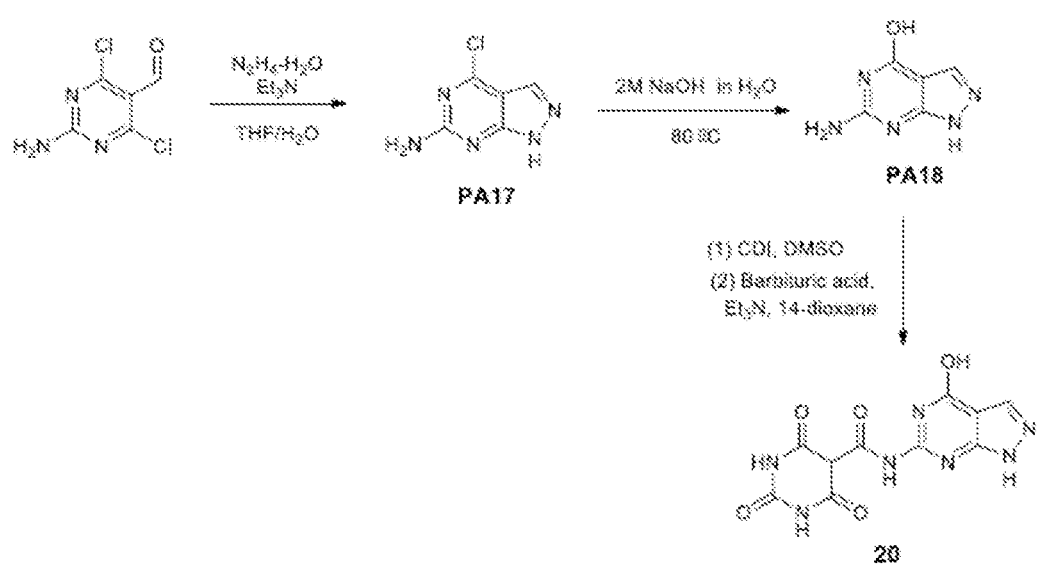
FIG. 19 illustrates a synthesis scheme for a compound having a structure represented by Formula ($V_a$), as described in Example 8.

Example 8: Preparation of 6-hydroxy-N-(4-hydroxy-1H-pyrazolo[3,4-d]pyrimidin-6-yl)-2,4-dioxo-1,2,3,4-tetrahydropyrimidine-5-carboxamide (20, Formula (V$_a$), with Reference to FIG. 19)

Step One. 4-Chloro-1H-pyrazolo[3,4-d]pyrimidin-6-amine (PA17). Hydrazine hydrate solution (295 μL, 5.21 mmol, 55% in H$_2$O) was added dropwise to a stirring suspension of 2-amino-4,6-dichloropyrimidine-5-carbaldehyde (1.00 g, 5.21 mmol) and triethylamine (835 mL, 5.99 mmol) in THF (21 mL) and H$_2$O (2.1 mL) at rt. The reaction was allowed to stir for 4 h, then concentrated. The residue was added H$_2$O, the precipitate was washed with water, then collected and dried under high vacuum to yield the product as a yellow solid (765 mg, 87% yield).

¹H NMR (500 MHz, DMSO-d⁶) δ 7.94 (s, 1H), 7.12 (s, 2H), 4.09 (s, 1H).

LCMS: m/z [M+1]⁺=169.98; R$_T$=0.79 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. 6-amino-1H-pyrazolo[3,4-d]pyrimidin-4-ol (PA18). 4-Chloro-1H-pyrazolo[3,4-d]pyrimidin-6-amine (PA17) (365 mg, 2.16 mmol) was added 2M NaOH (5.7 mL), the mixture was heated to 80° C. overnight. The reaction mixture was then cooled to rt, and concentrated HCl was added to adjust the pH to 5. Precipitate formed was filtered, washed with water, then dried under high vacuum to yield the product as a white solid (205 mg, >99% purity, 94% yield).

$^1$H NMR (500 MHz, DMSO-d$^6$) δ 10.46 (s, 1H), 7.75 (s, 1H), 6.47 (s, 2H).

LCMS: m/z [M+1]$^+$=152.19; R$_T$=0.46 min; purity=>99%.

HPLC conditions: Column: XTerra RP18, 3.5 μm, 3.0×50 mm; Gradient: 5% to 100% B in 2.5 minutes; 100% B for 1 minute; 1 mL/min. Eluent A: Milli-Q H$_2$O+0.1% Formic Acid; Eluent B: Acetonitrile+0.1% Formic Acid.

Step Three. 6-hydroxy-N-(4-hydroxy-1H-pyrazolo[3,4-d]pyrimidin-6-yl)-2,4-dioxo-1,2,3,4-tetrahydropyrimidine-5-carboxamide (20). To a stirring solution of PA18 (205 mg, 1.36 mmol) in anhydrous DMSO (1.4 mL) was added 1,1'carbonyldiimidazole (331 mg, 2.04 mmol) was added at rt, under inert atmosphere. The resulting solution was stirred for 20 min at rt. In a separate flask containing barbituric acid (174 mg. 1.36 mmol) was added anhydrous 1,4-dioxane (4.5 mL), then heated to 50° C. Et$_3$N (303 μL, 2.18 mmol) was added and stirred for 15 min at 50° C. The isocyanate generated from PA18 in DMSO was added to the stirring suspension, then heated to 80° C. until complete consumption of the starting materials were observed via LCMS (20 h). The reaction mixture was cooled to rt, then acidified with 6M HCl (aq), the precipitate formed was isolated, then triturated with H$_2$O, MeOH, followed by acetonitrile, to yield the product (20) as a brown solid (49 mg, 99.8% purity, 12% yield).

$^1$H NMR (500 MHz, DMSO-d6+DCl in D$_2$O) δ 7.29 (s, 1H).

LCMS: m/z [M+1]$^+$=306.52; RT=1.61 min: purity=99.8%.

HPLC conditions: Column: XTerra RP18, 3.5 μm, 3.0×50 mm; Gradient: 5% to 100% B in 2.5 minutes; 100% B for 1 minute; 1 mL/min. Eluent A: Milli-Q H$_2$O+0.1% Formic Acid; Eluent B: Acetonitrile+0.1% Formic Acid.

Figure 20:
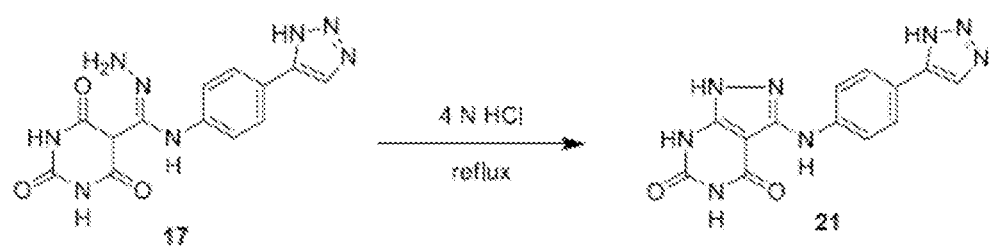
FIG. 20 illustrates a synthesis scheme for a compound having a structure represented by Formula ($VI_b$), as described in Example 9.

Example 9: Preparation of 3-((4-(1H-1,2,3-triazol-5-yl)phenyl)amino)-1H-pyrazolo[3,4-d]pyrimidine-4,6(5H,7H)-dione (21, Formula (VI$_b$), with Reference to FIG. 20)

Compound 17 (70 mg, 0.21 mmol) and HCl (2 mL, 4 N in water) was mixed and reflux for 1 hour, until LCMS showed complete consumption of starting material. The precipitate was filtered to yield the product (21) as a white solid (53 mg, 98.9% purity, 87% yield), after drying under high vacuum.

$^1$H NMR (500 MHz, d$^6$-DMSO+DCl) δ 8.16 (s, 1H), 7.74 (d, J=8.9 Hz, 2H), 7.52 (d, J=8.7 Hz, 2H),

LCMS: m/z [M-1]$^-$=309.23; R$_T$=3.23 min; purity=98.9%.

HPLC conditions: Waters XTerra RP18 3.5 μm, 3.0×50 mm; hold 5% B for 1.0 minute, 5% to 95% B in 5.0 minutes, then hold 5% B for 1.0 minute, run time=7.0 min;

Eluents: A=0.1% HCO$_2$H in water; B=0.1% HCO$_2$H in MeCN.

Figure 21:
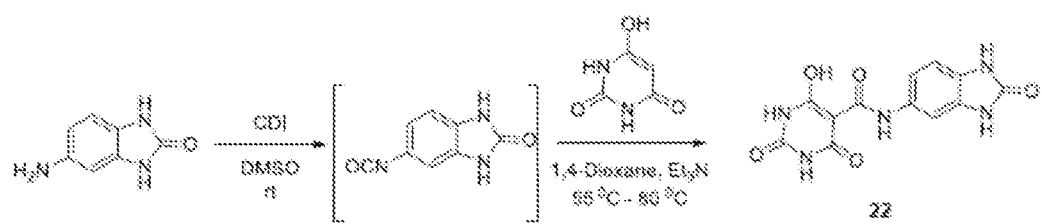
FIG. 21 illustrates a synthesis scheme for a compound having a structure represented by Formula ($IV_a$), as described in Example 10.

Example 10: Preparation of 6-hydroxy-2,4-dioxo-N-(2-oxo-2,3-dihydro-1H-benzo[d]imidazol-5-yl)-1,2,3,4-tetrahydropyrimidine-5-carboxamide (22, Formula (IV$_a$), with Reference to FIG. 21)

To a solution of 5-aminobenzoimidazolone (100 mg, 0.67 mmole) in dry DMSO (1.0 mL) at rt under nitrogen was added CDI (163 mg, 1.01 mmol) in one portion. The reaction mixture was stirred at rt for 2 h. This isocyanate intermediate was used as such in the next step.

In a separate flask, to a suspension of barbituric acid (94 mg, 0.74 mmol) in anhydrous 1,4-dioxane (1.0 mL) at 55° C. was added triethylamine (101 mg, 1.01 mmol) and reaction mixture stirred at 55° C. for 20 min, then the above isocyanate intermediate (solution in DMSO) was added. The resulting reaction mixture was heated at 80° C. for 2 h. Reaction mixture cooled to 0° C., precipitate formed was filtered, washed with water, dried under high vacuum, triturated with ether to provide the crude product as a light grey powder. Crude product was purified via ISCO (C18, 0 to 30% acetonitrile in water with ammonium bicarbonate buffer 10.0 mM over 20 CV gradient) to yield the product (22) as a white solid (96 mg, 99.2% purity, 47% yield).

$^1$H NMR (500 MHz, DMSO-d$^6$) δ 11.78 (s, 1H), 10.32 (d, J=68.9 Hz, 1H), 9.58-9.28 (m, 2H), 7.38 (s, 1H), 7.03 (s, 2H), 6.72 (d, J=16.7 Hz, 2H).

LCMS: m/z [M+1]$^+$=304.15; R$_T$=0.89 min; purity=99.2%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 22:
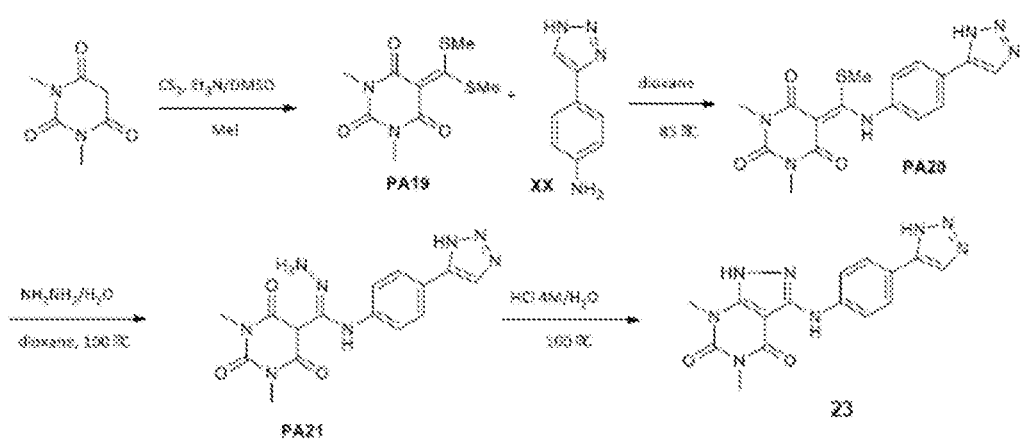
FIG. 22 illustrates a synthesis scheme for a compound having a structure represented by Formula ($VI_c$), as described in Example 11.

Example 11: Preparation of 3-((4-(1H-1,2,3-triazol-5-yl)phenyl)amino)-5,7-dimethyl-1H-pyrazolo[3,4-d]pyrimidine-4,6(5H,7H)-dione (23, Formula (VI$_c$), with Reference to FIG. 22)

Step One. 5-(bis(methylthio)methylene)-1,3-dimethylpyrimidine-2,4,6(1H,3H,5H)-trione (PA19). To a solution of 1,3-dimethylbarbituric acid (2.00 g, 12.81 mmol) and Et$_3$N (3.75 mL, 26.90 mmol), in DMSO (8.5 mL), was added CS$_2$ (1.55 mL, 25.86 mmol). The resulting solution was stirred 2.5 h at rt before addition of MeI (1.60 mL, 25.70 mmol). After 3 h at rt, the reaction was stopped The reaction was poured into H$_2$O and extracted twice with AcOEt. The combined organic phases were washed with H$_2$O (×3), dried over MgSO$_4$, then concentrated to dryness. The residue was triturated with diethyl ether and the solid was filtrated to provide the desired compound (1.4 g, >99% purity). This operation was repeated with the filtrate after concentration to yield an additional 1.0 g of product (>99% purity), with a combined mass of 2.4 g (71% yield).

$^1$H NMR (500 MHz, DMSO) δ 3.19 (s, 6H), 2.56 (s, 6H).

LCMS: m/z [M+1]$^+$=261.17; R$_T$=1.15 min; purity=>99%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. 5-(((4-(1H-1,2,3-triazol-5-yl)phenyl)amino)(methylthio)methylene)-1,3-dimethylpyrimidine-2,4,6(1H,3H,5H)-trione (PA20). A mixture of PA19 (488 mg, 1.87 mmol) and aniline XX (300 mg, 1.87 mmol), in dioxane (12 mL) was heated at 85° C. for 1 h. The solvent was evaporated in vacuo to provide the product (746 mg, 96% yield, 90% purity).

LCMS: m/z [M+1]$^+$=373.17; RT=1.22 min: purity=90%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. (E)-N-(4-(1H-1,2,3-triazol-5-yl)phenyl)-1,3-dimethyl-2,4,6-trioxohexahydropyrimidine-5-carbohydrazonamide (PA21).

To a solution of PA21 (125 mg, 0.34 mmol), in dioxane (6 mL), was added the hydrazine (0.215 mL, 3.37 mmol). The reaction was heated at 100° C. for 30 min. The solvent was evaporated in vacuo. The crude material was used in the next step assuming quantitative yield of 119 mg.

LCMS: m/z [M+1]$^+$=357.21; $R_T$=1.01 min; purity=85%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Four. 3-((4-(1H-1,2,3-triazol-5-yl)phenyl)amino)-5,7-dimethyl-1H-pyrazolo[3,4-d]pyrimidine-4,6(5H,7H)-dione (23). PA21 (119 mg, 0.33 mmol), in an aqueous solution of 4 M HCl (3 mL), was heated at 100° C. for 1 h. DMSO was added, the precipitate was and the filtrate was collected and then concentrated to be purified by reverse phase chromatography (C18 column=30 g, 0 to 40% CH$_3$CN in water over a 10 min gradient) to provide the product (23) as a beige solid (10 mg, 8% yield, >97% purity), after lyophilization.

$^1$H NMR (500 MHz, DMSO) δ 8.42 (s, 1H), 8.20 (s, 1H), 7.75 (d, J=8.7 Hz, 2H), 7.50 (d, J=7.9 Hz, 2H), 3.36 (s, 3H), 3.19 (s, 3H).

LCMS: m/z [M+1]$^+$=339.18; $R_T$=1.10 min; purity >97%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 23:
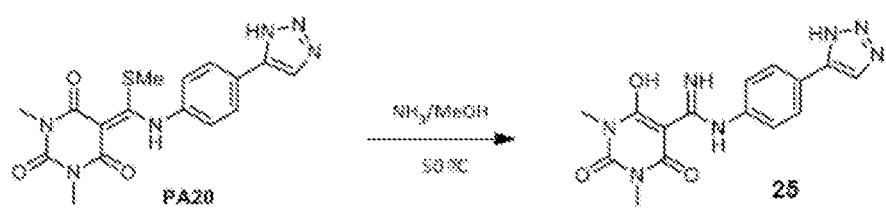
FIG. 23 illustrates a synthesis scheme for a compound having a structure represented by Formula ($I_f$), as described in Example 12.

Example 12: Preparation of N-(4-(1H-1,2,3-triazol-5-yl)phenyl)-6-hydroxy-1,3-dimethyl-2,4-dioxo-1,2,3,4-tetrahydropyrimidine-5-carboximidamide (25, Formula (I$_f$), with Reference to FIG. 23)

A solution of PA20 (50 mg, 0.13 mmol), in a solution of NH$_3$ (1 mL, 7 M in MeOH) was heated at 50° C. for 4 h. The reaction was cooled to rt, the precipitate formed was filtered and collected. The solid was added a mixture of CH$_3$CN—H$_2$O to provide the title compound (25) (19 mg, 42% yield, >99% purity), after lyophilization.

$^1$H NMR (500 MHz, DMSO) δ 15.13 (br s, 1H), 12.34 (s, 1H), 10.22 (s, 1H), 8.39 (s, 1H), 7.97 (d, J=8.4 Hz, 2H), 7.80 (s, 1H), 7.42 (d, J=8.4 Hz, 2H), 3.18 (d, J=8.7 Hz, 6H).

LCMS: m/z [M+1]$^+$=342.09; $R_T$=1.22 min; purity >99%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 24:
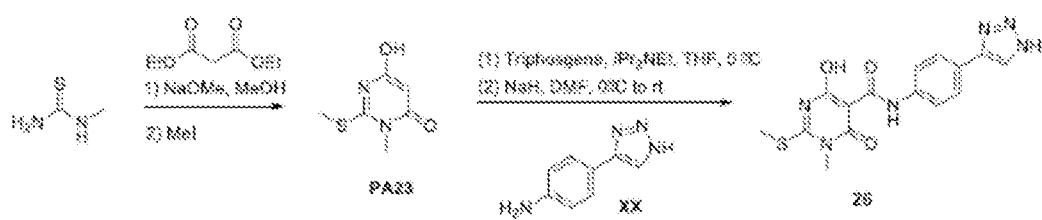
FIG. 24 illustrates a synthesis scheme for a compound having a structure represented by Formula ($II_a$), as described in Example 13.

Example 13: Preparation of N-(4-(3H-1,2,3-triazol-4-yl)phenyl)-4-hydroxy-1-methyl-2-(methylthio)-6-oxo-1,6-dihydropyrimidine-5-carboxamide (26, Formula (II$_a$), with Reference to FIG. 24)

Step One. 6-hydroxy-3-methyl-2-(methylthio)pyrimidin-4(3H)-one (PA23). A mixture of N-methyl thiourea (2.00 g, 22.2 mmol), diethyl malonate (3.4 mL, 22.2 mmol), and sodium methoxide (10.1 mL, 44.4 mmol, 4.4 M in methanol) was heated to reflux for 3 h. The reaction was then cooled to 50° C., iodomethane (1.4 mL, 22.2 mmol) was added in one-portion and allowed to stir for an additional 30 min at the same temperature. The solid formed was filtered, then collected, dissolved in water, neutralized with glacial acetic acid. The precipitate formed was filtered and washed with water to yield the product as a white solid (2.62 g, >99% purity, 69% yield).

$^1$H NMR (500 MHz, DMSO-d$^6$) δ 3.31 (s, 1H), 2.52 (s, 1H).

LCMS: m/z [M+1]$^+$=172.84; $R_T$=0.89 min; purity=>99%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. N-(4-(3H-1,2,3-triazol-4-yl)phenyl)-4-hydroxy-1-methyl-2-(methylthio)-6-oxo-1,6-dihydropyrimidine-5-carboxamide (26). Triphosgene (23 mg, 0.0766 mmol) was added to a solution of XX (35 mg, 0.219 mmol) and iPr$_2$NEt (114 µL, 0.657 mmol) in anhydrous THF (730 µL), at 0° C., under inert atmosphere. The reaction was allowed to stir at 0° C. for 1 h, anhydrous DMF (1.0 mL) was then added to form a homogenous solution. In a separate flask containing PA23 (45 mg, 0.263 mmol) was dissolved in anhydrous DMF (3.4 mL), the solution was cooled to 0° C. NaH (11 mg, 0.285 mmol, 60% dispersed in oil) was added at 0° C., stirred at the same temperature for 5 min, then allowed to warm up to rt over 30 min. The isocyanate generated from XX in THF/DMF was added dropwise to the stirring suspension, the reaction was heated to 60° C. for 2 h. The reaction mixture was cooled to rt, the solid formed was filtered and collected. The crude product was purified via preparative chromatography (C18, 10 to 100% acetonitrile in water with ammonium formate buffer 10 mM, over 10 min gradient) to yield the product (26) as a yellow solid (5.5 mg, 96.45 purity, 7% yield), after lyophillization.

$^1$H NMR (500 MHz, DMSO-d$^6$) δ 15.48 (s, 1H), 11.77 (s, 1H), 7.90 (d, J=8.6 Hz, 2H), 7.74 (d, J=8.7 Hz, 2H), 3.49 (s, 3H), 2.63 (s, 3H).

LCMS: m/z [M+1]$^+$=359.17; $R_T$=1.49 min; purity=96.4%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 25:
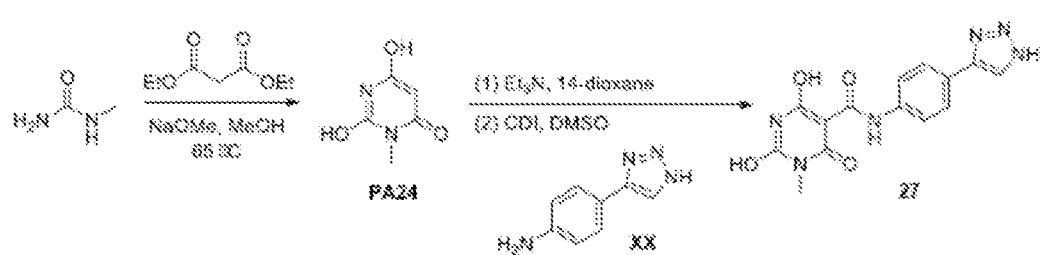
FIG. 25 illustrates a synthesis scheme for a compound having a structure represented by Formula ($I_g$), as described in Example 14.

Example 14: Preparation of N-(4-(1H-1,2,3-triazol-4-yl)phenyl)-2,4-dihydroxy-1-methyl-6-oxo-1,6-dihydropyrimidine-5-carboxamide (27, Formula (I$_g$), with Reference to FIG. 25)

Step One. 2,6-Dihydroxy-3-methylpyrimidin-4(3H)-one (PA24). To the stirring suspension of N-methyl urea (2.00 g, 27.0 mmol) and diethyl malonate (4.10 mL, 4.32 mmol) in methanol (11 mL) was slowly added NaOMe (12.2 mL, 54.0 mmol, 4.4 M in MeOH). The resulting solution was heated to reflux and stirred overnight (15 h). The reaction mixture was then cooled to room temperature, and then acidified using an aqueous solution of HCl (6M). The resulting mixture was concentrated, then added iPrOH, stirred at 40° C. for 30 min. The precipitate was filtered, washed with minimal water, then washed with iPrOH, then dried under high vacuum. The product was obtained as a white solid (4.58 g, 55% purity, 66% yield).

$^1$H NMR (500 MHz, DMSO-d$^6$) δ 3.59 (s, 2H), 3.06 (s, 3H).

LCMS: m/z [M+1]$^+$=143.72; $R_T$=0.22 min; purity=>99%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. N-(4-(1H-1,2,3-triazol-4-yl)phenyl)-2,4-dihydroxy-1-methyl-6-oxo-1,6-dihydropyrimidine-5-carboxamide (27). To a stirring solution of XX (39 mg, 0.251 mmol, 97% purity) in anhydrous DMSO (250 µL) was added 1,1'carbonyldiimidazole (61 mg, 0.377 mmol) was added at rt, under inert atmosphere. The resulting solution was stirred for 20 min at rt. In a separate flask containing PA24 (71 mg, 0.502 mmol) was added anhydrous 1,4-dioxane (840 µL), then heated to 50° C. Et$_3$N (105 mL, 0.753 mmol) was added and stirred for 15 min at 50° C. The isocyanate generated from XX in DMSO was added to the stirring suspension, then heated to 80° C. until complete consumption of the starting materials were observed via LCMS. After 30 min, the reaction mixture was cooled to rt, then acidified with 6M HCl (aq), the precipitate formed was isolated, then triturated with H$_2$O, MeOH, followed by acetonitrile. The solid was then lyophilized to remove traces of water to yield the product (27) as a white solid (45.5 mg, 99.5% purity, 55% yield).

$^1$H NMR (500 MHz, DMSO-d$^6$) δ 14.97 (s, 1H), 12.33 (s, 1H), 11.70 (s, 1H), 8.30 (s, 1H), 7.90 (d, J=8.6 Hz, 2H), 7.65 (d, J=8.7 Hz, 2H), 3.18 (s, 3H).

LCMS: m/z [M+1]$^+$=329.14; R$_T$=1.18 min; purity=99.5%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 26:
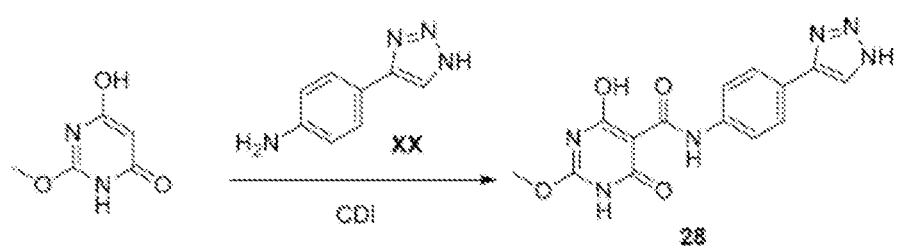
FIG. 26 illustrates a synthesis scheme for a compound having a structure represented by Formula ($II_b$), as described in Example 15.

Example 15: Preparation of N-(4-(3H-1,2,3-triazol-4-yl)phenyl)-4-hydroxy-2-methoxy-6-oxo-1,6-dihydropyrimidine-5-carboxamide (28, Formula (II$_b$), with Reference to FIG. 26)

To a stirring solution of XX (73 mg, 0.457 mmol, 97% purity) in anhydrous DMSO (460 µL) was added 1,1'carbonyldiimidazole (111 mg, 0.686 mmol) was added at rt, under inert atmosphere. The resulting solution was stirred for 20 min at rt. In a separate flask containing 6-hydroxy-2-methoxypyrimidin-4(3H)-one (65 mg, 0.457 mmol) was added anhydrous 1,4-dioxane (1.5 mL), then heated to 50° C. Et$_3$N (102 µL, 0.731 mmol) was added and stirred for 15 min at 50° C. The isocyanate generated from XX in DMSO was added to the stirring suspension, then heated to 80° C. until complete consumption of the starting materials were observed via LCMS. After 20 h, the reaction mixture was cooled to rt, then acidified with 6M HCl (aq), the precipitate formed was isolated, then triturated with H$_2$O, MeOH, followed by acetonitrile. The crude product was purified via ISCO (C18, 0 to 100% acetonitrile in water with ammonium formate buffer 10 mM over 20 CV gradient), after lyophillization, yield the product (28) as a white solid (4.8 mg, >99% purity, 3% yield).

$^1$H NMR (500 MHz, DMSO-d$^6$) δ 12.15 (s, 1H), 9.55 (s, 1H), 8.17 (s, 1H), 7.69 (d, J=8.6 Hz, 2H), 7.61 (d, J=8.7 Hz, 2H), 3.29 (s, 3H).

LCMS: m/z [M+1]=328.83; R$_T$=1.01 min; purity=>99%

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 27:
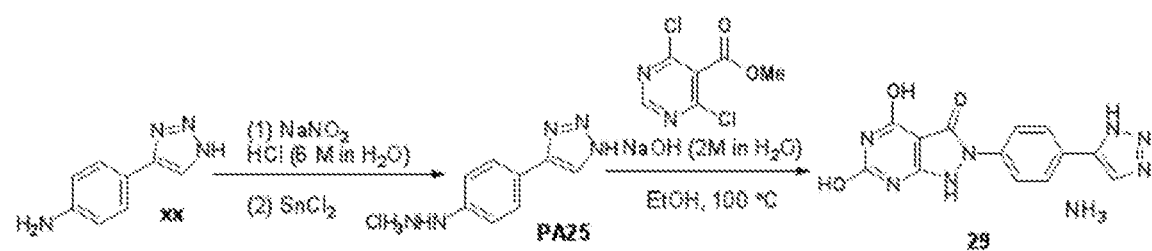
FIG. 27 illustrates a synthesis scheme for a compound having a structure represented by Formula ($VII_a$), as described in Example 16.

Example 16: Preparation of 2-(4-(1H-1,2,3-triazol-5-yl)phenyl)-4,6-dihydroxy-1H-pyrazolo[3,4-d]pyrimidin-3(2H)-one-ammonia salt (29, Formula (VII$_a$), with Reference to FIG. 27)

To a stirring solution of XX (105 mg, 0.656 mmol) in HCl (6 M in H$_2$O) was added a solution of NaNO$_2$ (48 mg, 0.689 mmol) in H$_2$O (0.1 mL) at 0° C. The reaction was kept at the same temperature for 1 h. Tin (II) chloride monohydrate (296 mg, 1.31 mmol) dissolved in HCl (6 M in H$_2$O) was added dropwise to the reaction mixture at 0° C. The reaction was then allowed to warm up to rt over 3 h. The reaction mixture was then basified with 2 M NaOH, then extracted with ethyl acetate and a mixture of 25% isopropanol in chloroform. The aqueous and organic fractions were combined, then acidified with HCl (6 M in H$_2$O), the precipitate was filtered off, and the filtrate was concentrated to yield the product PA25 in an aqueous solution.

Crude hydrazine salt PA25 aqueous solution was added methyl 4,6-dichloropyrimidine-5-carboxylate (90 mg, 0.437 mmol) dissolved in EtOH (2.2 mL). The reaction mixture was added 2 M NaOH (1.1 mL), then sealed in a pressure vessel and heated to 100° C. for 15 h. The reaction was allowed to cool to rt, then concentrated under reduced pressure. The crude product was purified via ISCO (C18, 0 to 100% acetonitrile in water with ammonium formate buffer 10 mM over 20 CV gradient), after lyophillization, yield the product (29) as an orange solid (14.7 mg, 98.6% purity, 11% yield).

$^1$H NMR (500 MHz, DMSO-d$^6$) δ 8.34 (s, 1H), 7.87 (dt, J=8.1, 1.6 Hz, 2H), 7.49-7.44 (m, 2H), 7.38-7.33 (m, 1H).

HRMS (ESI+) m/z calculated for C$_{13}$H$_{13}$N$_8$O$_3$ [M+NH$_4$]$^+$: 329.11 found: 329.11.

LCMS: m/z [M+1]$^+$=312.0; R$_T$=1.17 min; purity=98.6%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 28:
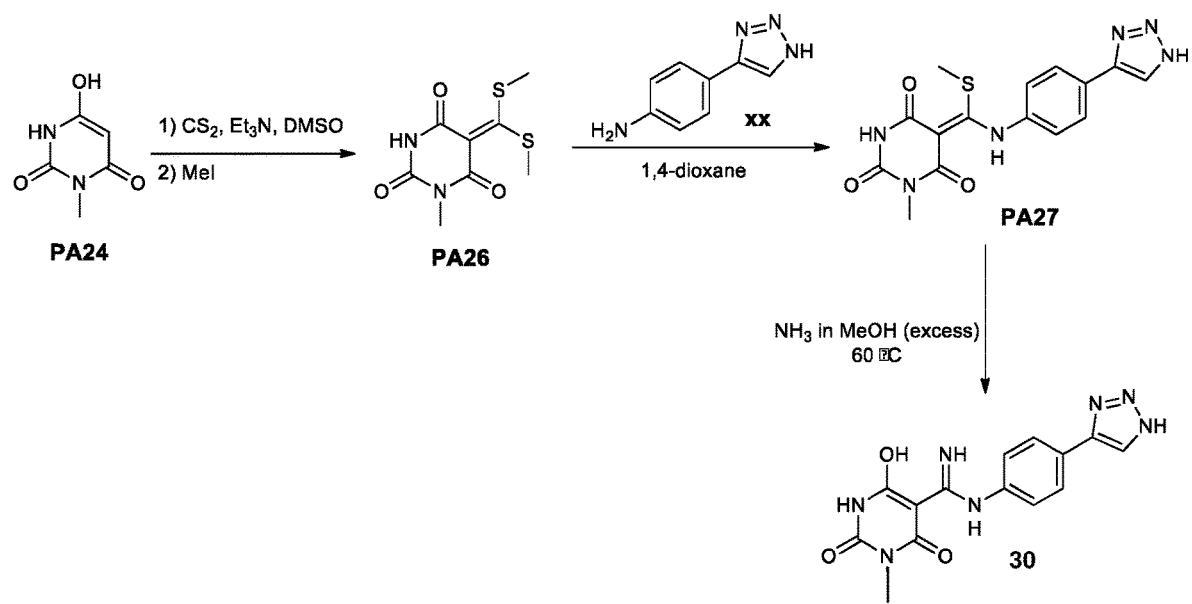
FIG. 28 illustrates a synthesis scheme for a compound having a structure represented by Formula ($I_h$), as described in Example 17.

Example 17: Preparation of N-(4-(3H-1,2,3-triazol-4-yl)phenyl)-4-hydroxy-2-methoxy-6-oxo-1,6-dihydropyrimidine-5-carboxamide (30, Formula (I$_h$), with Reference to FIG. 28)

Step One. 5-(bis(methylthio)methylene)-1-methylpyrimidine-2,4,6(1H,3H,5H)-trione (PA26). A mixture of 6-hydroxy-3-methylpyrimidine-2,4(1H,3H)-dione (PA24) (2.339 g, 7.04 mmol, 55% purity), triethylamine (2.0 mL, 14.1 mmol), and carbon disulfide (850 µL, 14.1 mmol) was allowed to stir at rt until complete consumption of PA24 was observed via LCMS (0.5 h). The resulting reaction mixture was cooled in an ice-bath, iodomethane (880 µL, 14.1 mmol) was added in one-portion, the reaction was then allowed to warm up to rt over 20 h. The reaction mixture was poured into a ice-water with rapid stirring, then allowed to stand for 6 h. The precipitate formed was filtered, washed with water and diethyl ether. The precipitate was collected and dried under high vacuum to yield the product as a yellow solid (97 mg, 6% yield).

$^1$H NMR (500 MHz, DMSO-d$^6$) δ 3.12 (s, 3H), 2.55 (s, 6H).

LCMS: m/z [M+1]$^+$=246.93; R$_T$=0.99 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. (E)-5-((4-(1H-1,2,3-triazol-4-yl)phenylamino)(methylthio)methylene)-1-methylpyrimidine-2,4,6(1H,3H,5H)-trione (PA27). A mixture of 5-(bis(methylthio)methylene)-1-methylpyrimidine-2,4,6(1H,3H,5H)-trione (PA26) (22 mg, 0.0894 mmol, 1 eq) and 4-(1H-1,2,3-triazol-4-yl)benzenamine (XX) (14 mg, 0.0894 mmol, 1 eq) in anhydrous 1,4-dioxane (2.2 mL, 0.04 M) was sealed in a microwave vessel and heated to 100° C., until complete consumption of the starting material was observed via LCMS (20 h). The reaction mixture was cooled to rt, then concentrated to yield the crude product (PA #) as an off-white solid. The crude product was used without further purification.

LCMS: m/z [M+1]$^+$=358.92; R$_T$=1.06 min; purity=>99%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. N-(4-(3H-1,2,3-triazol-4-yl)phenyl)-4-hydroxy-2-methoxy-6-oxo-1,6-dihydropyrimidine-5-carboxamide (30). The crude product, PA27 was added a solution of 7.0 M NH$_3$ in methanol (1.0 mL) at rt. The reaction was sealed and heated to 60° C., until complete consumption of the starting material was observed via LCMS (20 h). The reaction mixture was allowed to cool to rt, the precipitate formed was filtered and washed with acetonitrile, then the solid was lyophilized to yield the product (30) as an off-white solid (19 mg, 98.8% purity, 66% yield over 2 steps).

$^1$H NMR (500 MHz, DMSO-d$^6$) δ 12.28 (s, 1H), 10.14 (s, 1H), 8.41 (s, 1H), 7.97 (d, J=8.5 Hz, 2H), 7.76 (s, 1H), 7.42 (d, J=8.4 Hz, 2H), 3.12 (s, 3H).

LCMS: m/z [M+1]$^+$=328.12; R$_T$=1.04 min; purity=98.8%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 29:
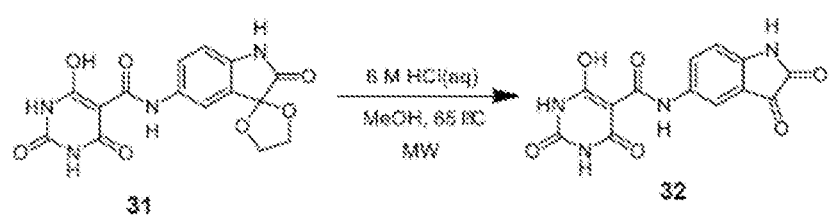
FIG. 29 illustrates a synthesis scheme for a compound having a structure represented by Formula ($IV_b$), as described in Example 18.

Example 18: Preparation of N-(2,3-dioxoindolin-5-yl)-6-hydroxy-2,4-dioxo-1,2,3,4-tetrahydropyrimidine-5-carboxamide (32, Formula (IV$_b$), with Reference to FIG. 29)

To a suspension of 31 (20.5 mg, 0.0570 mmol) in MeOH/1,4-dioxane (1.1 mL, 1:1 v/v, 0.05 M) was added 6 M HCl (110 μL). The resulting reaction mixture was sealed and heated in the microwave at 100° C. for 20 min. Acetonitrile (5 mL) was added, the precipitate formed was filtered, washed with water, and then acetonitrile to yield the product (32) as a dark red solid (7.9 mg, 44% yield).

$^1$H NMR (500 MHz, DMSO-δ6+AcOD) δ 7.68 (d, J=2.1 Hz, 1H), 7.50 (dd, J=8.4, 2.3 Hz, 1H), 6.86 (d, J=8.5 Hz, 1H).

LCMS: m/z [M+1]$^+$=317.36; R$_T$=0.88 min; purity=>99%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 30:
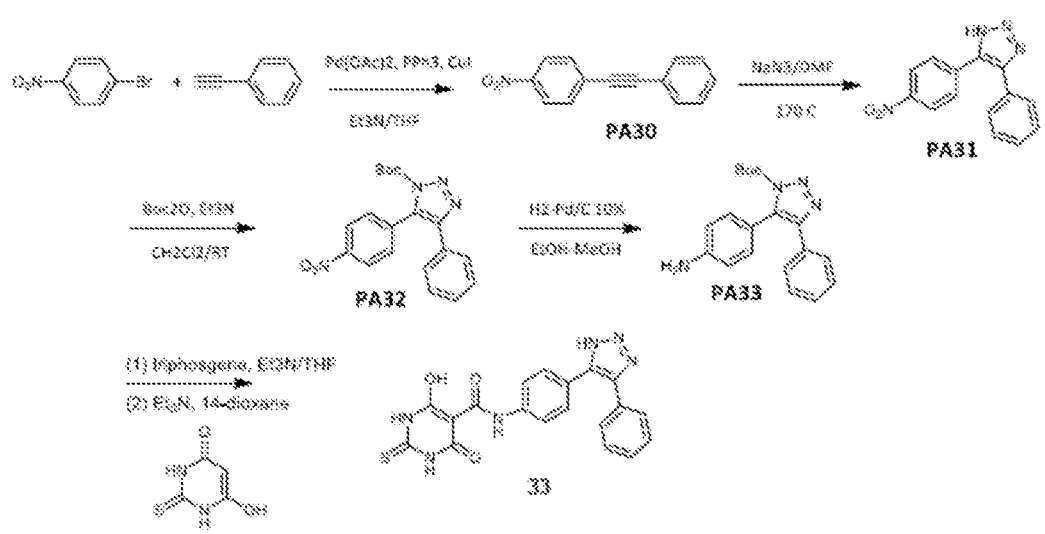
FIG. 30 illustrates a synthesis scheme for a compound having a structure represented by Formula ($I_m$), as described in Example 19.

Example 19: Preparation of 6-hydroxy-4-oxo-N-(4-(4-phenyl-1H-1,2,3-triazol-5-yl)phenyl)-2-thioxo-1,2,3,4-tetrahydropyrimidine-5-carboxamide (33, Formula (I$_m$), with Reference to FIG. 30)

Step One. 1-nitro-4-(phenylethynyl)benzene (PA30). To a round-bottomed flask was added Pd(OAc)$_2$ (21 mg, 0.094 mmol), PPh$_3$ (96 mg, 0.366 mmol), CuI (19 mg, 0.100 mmol), 4-iodoaniline (2.0 g, 9.13 mmol) and THF (24 mL). After bubbling N$_2$ through the reaction mixture for 5 min, phenylacetylene (1.20 mL, 10.91 mmol) and Et$_3$N (6.40 mL, 45.91 mmol) were added sequentially. The reaction was stirred overnight at rt. After diluting with sat. NH$_4$Cl, the mixture was extracted twice with AcOEt, the combined organic extracts were dried over MgSO$_4$, then concentrated to dryness. The residue was triturated with diethyl ether and the solid was filtrated and collected. This operation was repeated with the filtrate after concentration, the solid collected were combined to yield the product (0.69 g, 85% purity). The remaining residue was purified by combi-flash chromatography (dry pack, SiO column=80 g, 5% ethyl acetate in hexanes) to provide the titled compound (0.76 g, 95% purity) of the title compound was isolated with a combined mass of 1.45 g (93% yield).

LCMS: R$_T$=1.96 min; purity=95%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

$^1$H NMR (500 MHz, CDCl$_3$) δ 8.23 (d, J=9.0 Hz, 2H), 7.67 (d, J=9.0 Hz, 2H), 7.58-7.55 (m, 2H), 7.42-7.37 (m, 3H).

Step Two. 5-(4-nitrophenyl)-4-phenyl-1H-1,2,3-triazole (PA31). To a stirred solution of PA30 (690 mg, 3.09 mmol), in DMF (7.5 mL), was added NaN$_3$ (230 mg, 3.54 mmol). The resulting solution was heated at 170° C. for 3.5 h. The reaction mixture, diluted with H$_2$O, was extracted twice with AcOEt. The combined organic phases were washed with H$_2$O (×3) and then brine before it was dried over MgSO$_4$, then concentrated to dryness to yield the product (0.82 g, 99% yield, 96% yield).

LCMS: m/z [M+1]$^+$=267.01; R$_T$=1.58 min; purity=96%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. tert-butyl 5-(4-nitrophenyl)-4-phenyl-1H-1,2,3-triazole-1-carboxylate (PA32). To a stirred solution of PA31 (400 mg, 1.50 mmol), in CH$_2$Cl2 (5 mL), was added a solution of Boc$_2$O (394 mg, 1.80 mmol), in CH$_2$Cl2 (5 mL), followed by addition of Et$_3$N (0.25 mL, 1.78 mmol). The resulting solution was stirred at rt for 2 h. The solvent was evaporated in vacuo. The residue was purified by combi-flash chromatography (SiO column=40 g, 5% ethyl acetate in hexanes) to yield the product (530 mg, 96% yield, 97% purity).

LCMS: m/z [M-Boc]$^+$=266.94; R$_T$=1.96 min; purity=97%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Four. tert-butyl 5-(4-aminophenyl)-4-phenyl-1H-1,2,3-triazole-1-carboxylate (PA33). A suspension of PA32 (223 mg, 0.609 mmol), in EtOH (10 mL), was treated with Pd/C 10% (100 mg), 15 mL of MeOH was added. The reaction was fitted with a hydrogen filled balloon and stirred at rt for 2 h. The reaction was filtered through a Millex syringe filter. Solvents were evaporated in vacuo to provide the expected amine (190 mg, 92% yield, >95% purity).

LCMS: m/z [M-Boc]$^+$=236.99; R$_T$=1.74 min; purity >95%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Five. 6-hydroxy-4-oxo-N-(4-(4-phenyl-1H-1,2,3-triazol-5-yl)phenyl)-2-thioxo-1,2,3,4-tetrahydropyrimidine-5-carboxamide (33). To a solution of triphosgene (60 mg, 0.202 mmol), in THF (1.0 mL) at 0° C., was added PA33 (190 mg, 0.565 mmol), in THF (2.0 mL), followed by Et$_3$N (0.120 mL, 0.840 mmol). The ice bath was removed and the resulting suspension was stirred 45 min at rt. To the thiobarbituric acid (90 mg, 0.624 mmol), in dioxane (4.5 mL) was added Et$_3$N (0.120 mL, 0.840 mmol). The resulting mixture was stirred 15 min at 55° C. To this suspension, was added the previous suspension of isocyanate generated in THF, followed by DMSO (1.0 mL) and the resulting solution was stirred 1 h at 80° C. The reaction was cooled to rt, the solid formed was filtered. The filtrate was then diluted with H$_2$O, the product precipitated and was filtered to yield the desired product as the Et$_3$N salt (43 mg, 95% purity). The aqueous phase was then extracted twice with AcOEt. The product started to precipitate in the organic phase. The two phases were separated and AcOEt was evaporated in vacuo. The residue was triturated in AcOEt and the solid was filtered to yield the product (69 mg, 90% purity). 30 mg of this isolated solid was purified by reverse phase chromatography (C18 column=30 g, 0 to 50% of CH$_3$CN in water, over 10 min gradient) to yield 33 (8 mg, 97% purity), after lyophilization. Note: Deprotection was observed during the purification, only 33 was isolated.

LCMS: m/z [M+1]$^+$=407.14; R$_T$=1.24 min; purity=97%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

$^1$H NMR (500 MHz, DMSO) δ 12.06 (s, 1H), 11.11 (s, 2H), 7.62 (d, J=8.6 Hz, 2H), 7.53-7.48 (m 2H), 7.44-7.29 (m, 5H).

Figure 31:
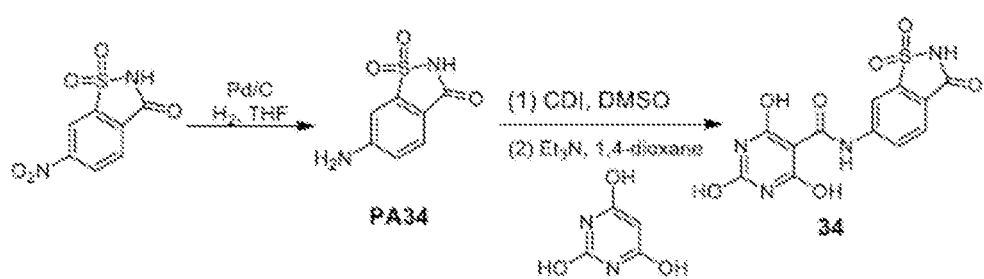
FIG. 31 illustrates a synthesis scheme for a compound having a structure represented by Formula ($III_a$), as described in Example 20.

Example 20: Preparation of N-(1,1-dioxido-3-oxo-2,3-dihydrobenzo[d]isothiazol-6-yl)-2,4,6-trihydroxypyrimidine-5-carboxamide (34, Formula (III$_a$), with Reference to FIG. 31)

Step One. 6-Aminobenzo [d]isothiazol-3(2H)-one 1,1-dioxide (PA34). 6-Nitrobenzo[d]isothiazol-3(2H)-one 1,1-dioxide (500 mg, 2.19 mmol) was dissolved in THF (11.0 mL). To the solution was added Pd/C (50 mg, 10% on charcoal) under N$_2$. The reaction was then evacuated and purged with H$_2$ (5×), then allowed to stir under H$_2$ for 4 h. After LCMS showed that the reaction was completed, the reaction was mixture was filtered through a pad a Celite. The filtrate was collected and the solvent was removed in vacuo to yield the product as a yellow solid (409 mg, 94% yield), without further purification.

$^1$H NMR (500 MHz, MeOD) δ 7.61 (d, J=8.5 Hz, 1H), 6.95 (d, J=1.9 Hz, 1H), 6.91 (dd, J=8.5, 2.0 Hz, 1H).

LCMS: m/z [M−1]$^−$=199.07; R$_T$=0.25 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. N-(1,1-dioxido-3-oxo-2,3-dihydrobenzo[d]isothiazol-6-yl)-2,4,6-trihydroxypyrimidine-5-carboxamide (34). Compound 34 was synthesized following the General Procedure 1. To a stirring solution of PA34 (267 mg, 0.135 mmol) in anhydrous DMSO (1.4 mL, 1.0 M) was added 1,1'carbonyldiimidazole (328 mg, 2.02 mmol) was added at rt, under inert atmosphere. The resulting solution was stirred for 20 min at rt. In a separate flask containing barbituric acid (173 mg, 1.35 mmol) was added anhydrous 1,4-dioxane (4.5 mL, 0.30 M), then heated to 55° C. Et$_3$N (300 μL, 2.16 mmol) was added and stirred for 15 min at 55° C. The isocyanate generated from the amine in DMSO was added to the stirring suspension, then heated to 80° C. until complete consumption of the starting materials were observed via LCMS (2 h). The reaction mixture was cooled to rt, then acidified with 6M HCl (aq), the precipitate formed was isolated, then triturated with water, MeOH, followed by acetonitrile. The crude product was further purified by reverse-phase chromatography (C18, gradient eluent from 0 to 30% acetonitrile in water with 10 mM ammonium formate buffer over 20 CV), fractions containing the product were collected and concentrated to dryness. The impure solid was then added acetonitrile and sonicated for 15 min, the resulting suspension was filtered, and the solid was washed with additional acetonitrile. The solid was collected and then added 10% H$_2$O/CH$_3$CN and sonicated for 30 min. The resulting suspension was filtered and the solid was washed with additional acetonitrile, to yield the pure product (34) as an off-white solid (113 mg, >99% purity, 24% yield).

$^1$H NMR (500 MHz, DMSO-66+AcOD) δ 8.18 (s, 1H), 7.67 (d, J=8.3 Hz, 1H), 7.57-7.52 (dd, J=8.3, 1.8 Hz, 1H).

LCMS: m/z [M−1]−=351.1; R$_T$=2.88 min; purity=>99%.

HPLC conditions: Atlantis T3, 3 μm, 4.6×30 mm; Isocratic 2% B for 0.5 minute, 2% to 100% B in 6.0 minutes; hold 100% B for 1.0 minute, 100% to 2% B in 0.05 minute, hold 2% B for 0.5 min, run time=8.0 min; Flow rate:1 mL/min; Eluents: A=Milli-Q H2O+0.1% Formic acid; B=MeCN.

Figure 32:
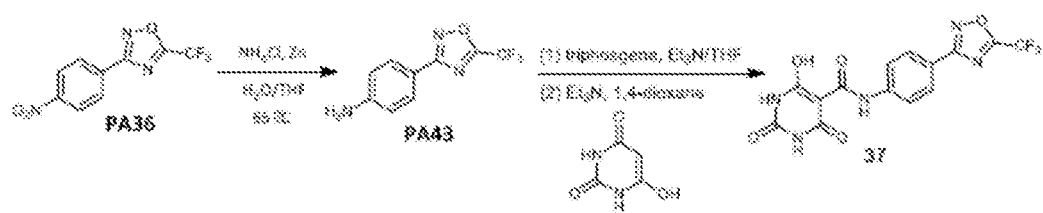
FIG. 32 illustrates a synthesis scheme for a compound having a structure represented by Formula ($I_n$), as described in Example 21.

Example 21: Preparation of 6-hydroxy-2,4-dioxo-N-(4-(5-(trifluoromethyl)-1,2,4-oxadiazol-3-yl)phenyl)-1,2,3,4-tetrahydropyrimidine-5-carboxamide (37, Formula (I), with Reference to FIG. 32)

Step One. 4-(5-(trifluoromethyl)-1,2,4-oxadiazol-3-yl) aniline (PA43). Ammonium chloride (253 mg, 4.73 mmol), in H$_2$O (5.0 mL) was added to a solution of PA36 (300 mg, 1.16 mmol), in THF (15.0 mL). Zinc powder (305 mg, 4.66 mmol) was then added. The reaction was stirred for 4 days at 65° C. The reaction was diluted with H$_2$O, and then extracted twice with AcOEt. The combined organic extract was dried over MgSO$_4$, and then concentrated. The residue was purified by combi-flash chromatography (SiO$_2$ column=40 g, 20% ethyl acetate in hexanes) to yield the desired compound (119 mg, 44% yield, 98% purity).

LCMS: m/z [M+1]$^+$=229.93; R$_T$=1.64 min; purity=98%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

$^1$H NMR (500 MHz, CDCl$_3$) δ 7.90 (d, J=8.7 Hz, 2H), 6.74 (d, J=8.7 Hz, 2H), 4.07 (br s, 2H).

Step Two. 6-hydroxy-2,4-dioxo-N-(4-(5-(trifluoromethyl)-1,2,4-oxadiazol-3-yl)phenyl)-1,2,3,4-tetrahydropyrimidine-5-carboxamide (37). To a solution of triphosgene (20 mg, 0.067 mmol), in THF (0.25 mL) at 0° C., was added PA43 (41 mg, 0.179 mmol), in THF (0.75 mL), followed by Et$_3$N (0.038 mL, 0.272 mmol). The ice bath was removed and the resulting suspension was stirred 45 min at rt. To the barbituric acid (26 mg, 0.203 mmol) in dioxane (1.5 mL) was added Et$_3$N (0.038 mL, 0.272 mmol). The resulting mixture was stirred 20 min at 55° C. To this suspension was added the previous suspension of the isocyanate generated in THF, followed by the addition of 0.5 mL of DMSO and the resulting solution was stirred 1.5 h at 80° C.

The reaction was filtered to remove the precipitate. Solvents of the filtrate were evaporated in vacuo and H$_2$O was added to the residue. The product crashed out and was filtered to provide the desired product as an Et$_3$N salt (50 mg). This solid was partially dissolved in a mixture of AcOEt and 1M HCl. The mixture was vigorously stirred for 1 h. The aqueous and organic layers were separated, and the solid formed in the organic phase was filtered. The solid was collected, then added CH$_3$CN and H$_2$O and lyophilized to provide a solid. The solid was triturated in DMSO to provide the desired product (37) (8 mg, 11% yield, 97% purity), after lyophilization.

$^1$H NMR (500 MHz, DMSO) δ 11.77 (s, 2H), 8.09 (d, J=7.7 Hz, 2H), 7.80 (d, J=7.8 Hz, 2H).

LCMS: m/z [M−1]$^−$=382.13; R$_T$=1.43 min; purity=97%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 33:
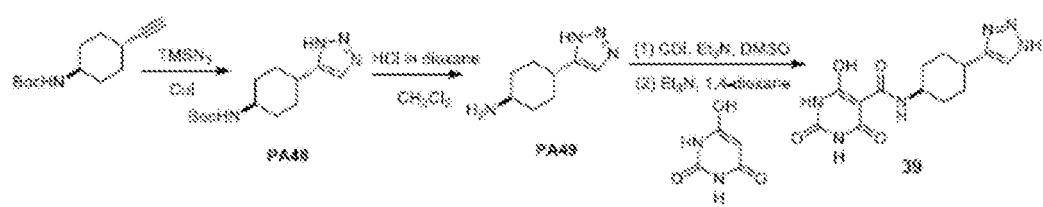
FIG. 33 illustrates a synthesis scheme for a compound having a structure represented by Formula ($I_i$), as described in Example 22.

Example 22: Preparation of N-(1,1-dioxido-3-oxo-2,3-dihydrobenzo[d]isothiazol-6-yl)-2,4,6-trihydroxypyrimidine-5-carboxamide (39, Formula (I), with Reference to FIG. 33)

Step One. tert-Butyl trans 4-(1H-1,2,3-triazol-5-yl)cyclohexyl)carbamate (PA48). To a stirring solution of tert-butyl trans 4-ethynylcyclohexylcarbamate (170 mg, 0.761 mmol) dissolved in MeOH/DMF (1.5 mL, 1:9 v/v) at room temperature, under inert atmosphere was added CuI (14 mg, 0.0761 mmol) in one-portion, followed by the addition of trimethylsilyl azide (150 μL, 1.12 mmol). The reaction was sealed in a pressure vessel and heated to 100° C. for 20 h, progress of the reaction was monitored by LCMS. The reaction was then allowed to cool to rt, then concentrated. The crude product was purified via ISCO (0 to 50% ethyl acetate in hexanes over 15 CV) to yield the product as a white solid (100 mg, 50% yield).

Rf=0.31 (50% ethyl acetate in hexanes).

$^1$H NMR (500 MHz) δ 7.81 (d, J=0.9 Hz, 1H), 7.69 (s, 1H), 3.61 (s, 1H), 2.93 (tt, J=12.1, 3.3 Hz, 1H), 2.33-2.25 (m, 4H), 1.76 (dddd, J=12.9, 12.9, 3.2, 3.2, 2H), 1.54 (dddd, J=13.4, 13.4, 3.6, 3.6 2H).

LCMS: m/z [M+1]$^+$=267.13; R$_T$=1.29 min.

HPLC conditions: Column: XBridge C18, 3.5 μm, 4.6×30 mm; Gradient: 5% B for 0.2 min, 5% to 100% B in 1.8 min; 100% B for 1 min; 1 mL/min; 3 min run. Eluent A: Milli-Q H$_2$O+10 mM ammonium formate pH: 3.8; Eluent B: Acetonitrile.

Step Two. Trans-4-(1H-1,2,3-Triazol-5-yl)cyclohexanamonium chloride (PA49). tert-Butyl trans-4-(1H-1,2,3-triazol-5-yl)cyclohexyl)carbamate PA48 (100 mg, 0.377 mmol) was dissolved in dichloromethane (0.75 mL) and methanol (0.75 mL) at rt. A solution of HCl (4.0 M in dioxane) was added in one-portion and allowed to stir at rt for 20 h. The reaction mixture was then concentrated to yield the product as a white solid (76 mg, >99% purity, 100% yield), without further purification.

$^1$H NMR (500 MHz, MeOD) δ 8.35 (s, 1H), 3.20-3.11 (m, 1H), 3.02-2.92 (m, 1H), 2.22-2.08 (m, 4H), 1.69-1.50 (m, 4H).

LCMS: R$_T$=0.25 min; purity=>99%.

HPLC conditions: Atlantis T3, 3 μm, 4.6×30 mm; Isocratic 2% B for 0.5 minute, 2% to 100% B in 6.0 minutes; hold 100% B for 1.0 minute, 100% to 2% B in 0.05 minute, hold 2% B for 0.5 min, run time=8.0 min; Flow rate:1 mL/min; Eluents: A=Milli-Q H2O+0.1% Formic acid; B=MeCN.

Step Three. 6-Aminobenzo[d]isothiazol-3(2H)-one 1,1-dioxide (39). To a stirring solution of PA49 (40 mg, 0.198 mmol) in anhydrous DMSO (200 μL, 1.0 M) was added Et$_3$N (55 μL, 0.396 mmol), followed by the addition of 1,1'carbonyldiimidazole (48 mg, 0.297 mmol) was added at rt, under inert atmosphere. The resulting solution was stirred for 20 min at rt. In a separate flask containing barbituric acid (25 mg, 0.198 mmol) was added anhydrous 1,4-dioxane (660 μL, 0.30 M), then heated to 55° C. Et$_3$N (44 μL, 0.317 mmol) was added and stirred for 15 min at 55° C. The isocyanate generated from the amine in DMSO was added to the stirring suspension, then heated to 80° C. until complete consumption of the starting materials were observed via LCMS (2 h). The reaction mixture was cooled to rt, then acidified with 6M HCl (aq), the precipitate formed was isolated, then triturated with water, MeOH, followed by acetonitrile. The crude product was further purified by reverse-phase chromatography (C18, gradient eluent from 0 to 100% acetonitrile in water with 0.1% formic acid buffer over 20 CV) to yield the product (39), after lyophillization, as an off-white solid (12.9 mg, 96.1% purity, 20% yield).

$^1$H NMR (500 MHz, DMSO-d6) δ 9.56 (d, J=7.8 Hz, 1H), 8.37-8.32 (m, 1H), 8.26 (s, 1H), 7.70 (s, 1H), 7.03 (s, 1H), 5.65 (d, J=7.8 Hz, 1H), 2.06-1.94 (m, 4H), 1.54-1.43 (m, 4H).

LCMS: m/z [M+1]$^+$=321.2; R$_T$=3.15 min; purity=96.1%.

HPLC conditions: Atlantis T3, 3 μm, 4.6×30 mm; Isocratic 2% B for 0.5 minute, 2% to 100% B in 6.0 minutes; hold 100% B for 1.0 minute, 100% to 2% B in 0.05 minute, hold 2% B for 0.5 min, run time=8.0 min; Flow rate:1 mL/min; Eluents: A=Milli-Q H2O+0.1% Formic acid; B=MeCN.

Figure 34:
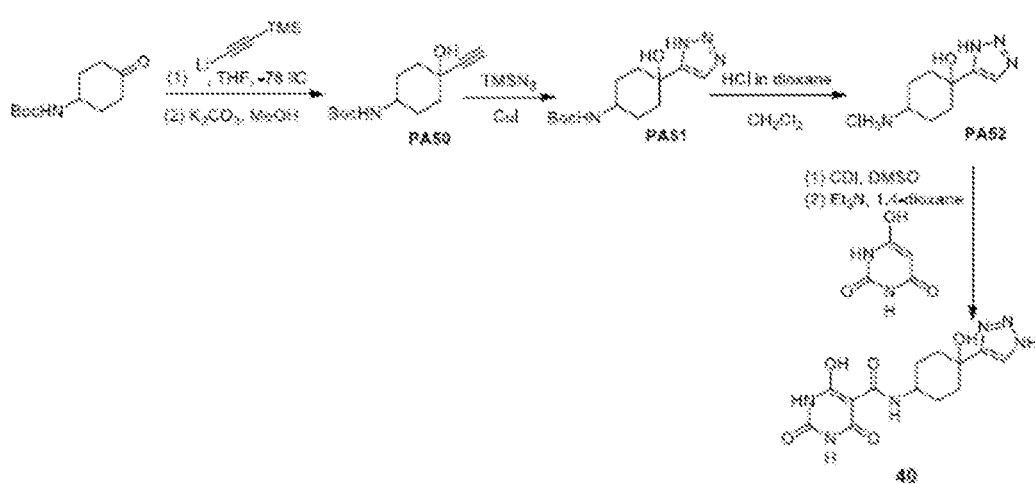
FIG. 34 illustrates a synthesis scheme for a compound having a structure represented by Formula ($I_j$), as described in Example 23.

Example 23: Preparation of 6-hydroxy-N-(4-hydroxy-4-(1H-1,2,3-triazol-4-yl)cyclohexyl)-2,4-dioxo-1,2,3,4-tetrahydropyrimidine-5-carboxamide (40, Formula (I$_j$), with Reference to FIG. 34)

Step One. tert-Butyl (4-ethynyl-4-hydroxycyclohexyl) carbamate (PA50). A solution of lithium (trimethylsilyl) acetylide (18.6 mL, 0.5 M in THF) was added slowly to tert-butyl (4-oxocyclohexyl)carbamate (991 mg, 4.65 mmol) in anhydrous THF (23 mL) at −78° C., under nitrogen. The reaction was allow to stir at the same temperature for 1 h, then warmed up to rt over 1 h. The resulting reaction mixture was quenched with a saturated aqueous solution of ammonium chloride, then diluted with ethyl acetate. The layers were separated, and the organic extract was washed with sat. NaHCO$_3$ (aq), water, and then brine, before drying over MgSO$_4$, and then concentrated to dryness to yield intermediate tert-butyl (4-hydroxy-4-((trimethylsilyl)ethynyl)cyclohexyl)carbamate.

The crude product was dissolved in methanol (15.5 mL), K$_2$CO$_3$ (1.94 g, 14.1 mmol) was added and allowed to stir at rt for 3 h. The reaction was then concentrated, then ethyl acetate was added, the solution was washed with brine, and the organic extract was dried over MgSO$_4$, then concentrated. The crude product (748 mg) was used without further purification.

Step Two. tert-Butyl (4-hydroxy-4-(1H-1,2,3-triazol-5-yl) cyclohexyl)carbamate (PA51). To a stirring solution of PA50 (748 mg, 3.13 mmol) dissolved in MeOH/DMF (6.3 mL, 1:9 v/v) at room temperature, under inert atmosphere was added CuI (60 mg, 0.313 mmol) in one-portion, followed by the addition of trimethylsilyl azide (605 μL, 4.60 mmol). The reaction was sealed in a pressure vessel and heated to 100° C. for 20 h, progress of the reaction was monitored by LCMS. The reaction was then allowed to cool to rt, then concentrated. The crude product was purified via ISCO (0 to 100% ethyl acetate in hexanes over 15 CV) to yield the product as a brown oil (330 mg, 1:1 dr, 37% yield).

LCMS: m/z [M+1]$^+$=283.10; R$_T$=1.41 min.

HPLC conditions: Column: XBridge C18, 3.5 μm, 4.6×30 mm; Gradient: 5% B for 0.2 min, 5% to 100% B in 1.8 min;

100% B for 1 min; 1 mL/min; 3 min run. Eluent A: Milli-Q H$_2$O+10 mM ammonium formate pH: 3.8; Eluent B: Acetonitrile.

Step Three. 4-Amino-1-(1H-1,2,3-triazol-5-yl)cyclohexanol hydrogen chloride salt (PA52). PA51 (330 mg, 1.18 mmol) was dissolved in dichloromethane (2.4 mL) at rt. A solution of HCl (4.2 mL, 4.0 M in dioxane) was added in one-portion and allowed to stir at rt for 16 h. The reaction mixture was then concentrated to yield the product as a brown oil (257 mg, 100% yield, 1:1 dr), without further purification.

LCMS: m/z [M+1]$^+$=182.88; R$_T$=0.23 min.

HPLC conditions: Column: XBridge C18, 3.5 μm, 4.6×30 mm; Gradient: 5% B for 0.2 min, 5% to 100% B in 1.8 min; 100% B for 1 min; 1 mL/min; 3 min run. Eluent A: Milli-Q H$_2$O+10 mM ammonium formate pH: 3.8; Eluent B: Acetonitrile.

Step Four. 6-hydroxy-N-(4-hydroxy-4-(1H-1,2,3-triazol-4-yl)cyclohexyl)-2,4-dioxo-1,2,3,4-tetrahydropyrimidine-5-carboxamide (40). To a stirring solution of PA52 (129 mg, 0.590 mmol) in anhydrous DMSO (590 μL, 1.0 M) was added Et$_3$N (164 μL, 0.1.18 mmol), followed by the addition of 1,1'carbonyldiimidazole (144 mg, 0.885 mmol) was added at rt, under inert atmosphere. The resulting solution was stirred for 20 min at rt. In a separate flask containing barbituric acid (76 mg, 0.198 mmol) was added anhydrous 1,4-dioxane (2.0 mL, 0.30 M), then heated to 55° C. Et$_3$N (130 μL, 0.944 mmol) was added and stirred for 15 min at 55° C. The isocyanate generated from the amine in DMSO was added to the stirring suspension, then heated to 80° C. until complete consumption of the starting materials were observed via LCMS (1.5 h). The reaction mixture was cooled to rt, then acidified with 6M HCl (aq), the precipitate formed was isolated, then triturated with water, MeOH, followed by acetonitrile. The crude product was further purified by reverse-phase chromatography (C18, gradient eluent from 0 to 100% acetonitrile in water with an ammonium formate buffer 10 mM over 20 CV) to yield the product (40), after lyophillization, as a brown solid (4.8 mg, 1:1 dr, 2% yield).

$^1$H NMR (500 MHz, DMSO-δ6) δ (1:1 dr) δ 8.19 (s, 1H), 7.53 (s, 1H), 7.02 (s, 1H), 4.47-4.41 (m, 2H), 3.97 (s, 3H), 3.77-3.72 (m, 2H), 3.68-3.65 (m, 2H).

Figure 35:
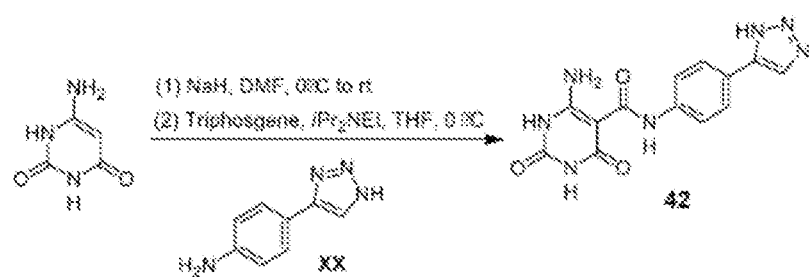
FIG. 35 illustrates a synthesis scheme for a compound having a structure represented by Formula ($I_k$), as described in Example 24.

Example 24: Preparation of N-(4-(1H-1,2,3-triazol-5-yl)phenyl)-6-amino-2,4-dioxo-1,2,3,4-tetrahydropyrimidine-5-carboxamide (42, Formula (I$_k$), with Reference to FIG. 35)

Triphosgene (342 mg, 1.15 mmol) was added to a solution of XX (527 mg, 3.29 mmol) and iPr$_2$NEt (1.7 mL, 9.87 mmol) in anhydrous THF (11.0 mL), at 0° C., under inert atmosphere. The reaction was allowed to stir at 0° C. for 1 h, anhydrous DMF (1.0 mL) was then added to form a homogenous solution. In a separate flask containing 6-aminouracil (502 mg, 3.95 mmol) was dissolved in anhydrous DMF (32 mL), the solution was cooled to 0° C. NaH (171 mg, 4.28 mmol, 60% dispersed in oil) was added at 0° C., stirred at the same temperature for 5 min, then allowed to warm up to rt over 30 min. The isocyanate generated from XX in THF/DMF was added dropwise to the stirring suspension, the reaction was heated to 60° C. for 1 h. The reaction mixture was cooled to rt, then concentrated to dryness. The crude product was purified via preparative chromatography (C18, 10 to 100% acetonitrile in water with ammonium formate buffer 10 mM, over 10 min gradient) to yield the product (42) as an off-white solid (32 mg, 98.7 purity, 3% yield), after lyophillization.

$^1$H NMR (500 MHz, DMSO-d$^6$) δ 8.37 (s, 1H), 7.71 (d, J=8.4 Hz, 2H), 7.55 (d, J=8.4 Hz, 2H).

LCMS: m/z [M−1]$^-$=312.1; R$_T$=0.98 min; purity=98.7%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 36:
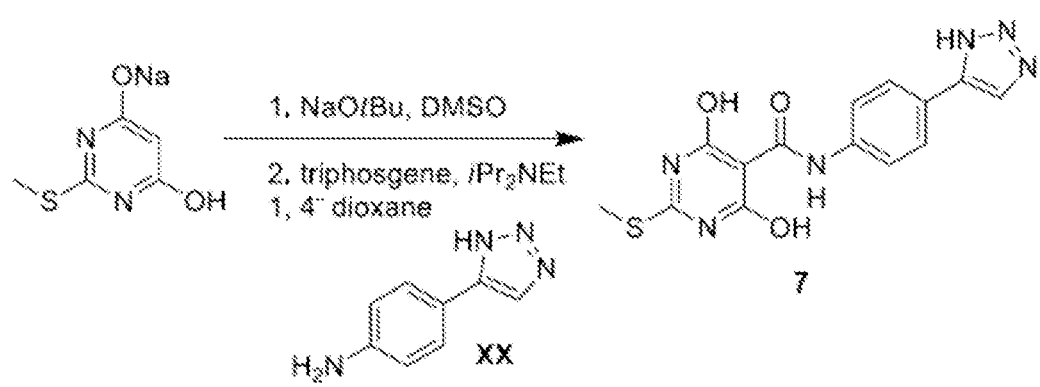
FIG. 36 illustrates a synthesis scheme for a compound having a structure represented by Formula ($II_c$), as described in Example 25.

Example 25: Preparation of N-(4-(1H-1,2,3-triazol-5-yl)phenyl)-4,6-dihydroxy-2-(methylthio)pyrimidine-5-carboxamide (7, Formula (II$_c$), with Reference to FIG. 36)

2-(Methylthio)pyrimidine-4,6-diol (127 mg, 0.800 mmol) was added to a stirring solution of sodium tert-butoxide (78 mg, 0.800 mmol) dissolved in DMSO (2 mL) at rt for 5 min. In a separate flask, aniline XX was dissolved in 1,4-dioxane (0.5 mL), to this solution was added triphosgene (39 mg, 0.132 mmol) in one-portion. The suspension was stirred vigorously for 2 min at rt, then iPr$_2$NEt (139 □L, 0.800 mmol) was added. The suspension was stirred vigorously at rt for 2 min. Freshly prepared solution of sodium 6-hydroxy-2-(methylthio)pyrimidin-4-olate in DMSO was added to the suspension in one-portion. The reaction was stirred at 90° C. for 30 min. until complete consumption of starting material observed via LCMS. The reaction mixture was loaded directly on C18 column (60 g) and purified via ISCO (C18, 0 to 100% acetonitrile in water, with an ammonium bicarbonate buffer 10 mM) to yield the product (7) as a white solid (60 mg, 44% yield, 97.8% purity), after lyophilisation.

$^1$H NMR (400 MHz, DMSO-d6+DCl in D$_2$O) δ 11.71 (s, 1H), 8.32 (s, 1H), 7.86 (d, J=8.7 Hz, 2H), 7.68 (d, J=8.6 Hz, 2H), 2.48 (s, 3H).

LCMS: m/z [M−1]$^-$=343.0; R$_T$=1.29 min.

HPLC conditions: Column: XBridge C18, 3.5 μm, 4.6×30 mm; Gradient: 5% B for 0.2 min, 5% to 100% B in 1.8 min; 100% B for 1 min; 1 mL/min; 3 min run. Eluent A: Milli-Q H$_2$O+10 mM ammonium formate pH: 3.8; Eluent B: Acetonitrile.

Figure 37:
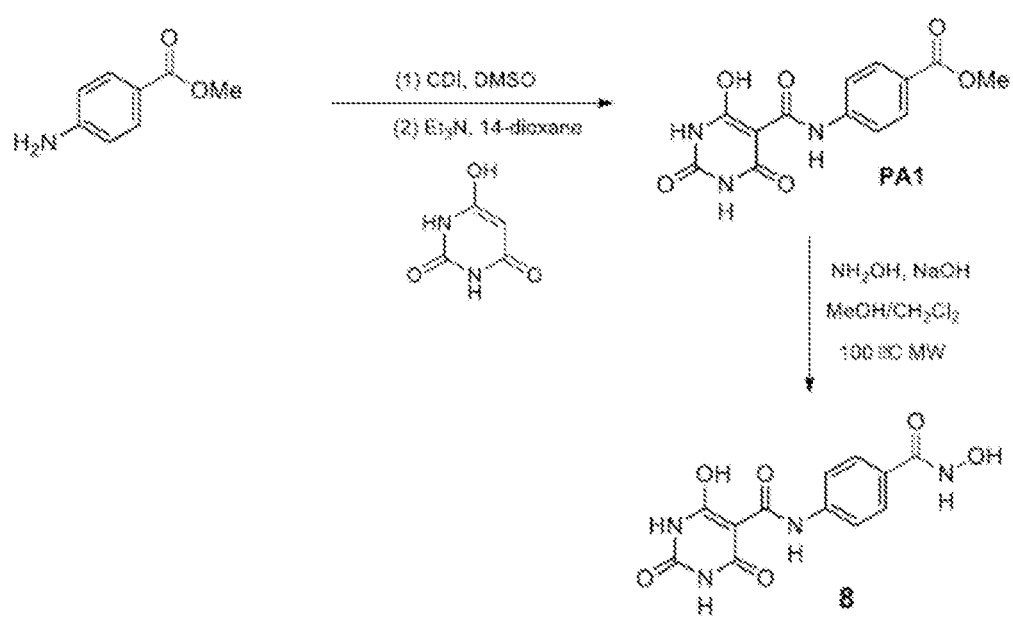
FIG. 37 illustrates a synthesis scheme for a compound having a structure represented by Formula (VIII$_a$), as described in Example 26.

Example 26: Preparation of 6-hydroxy-N-(4-(hydroxycarbamoyl)phenyl)-2,4-dioxo-1,2,3,4-tetrahydropyrimidine-5-carboxamide (8, Formula (VIII$_a$), with reference to FIG. 37)

Step One. Methyl 4-(6-hydroxy-2,4-dioxo-1,2,3,4-tetrahydropyrimidine-5-carboxamido)benzoate (PA1). To a stirring solution of methyl 4-aminobenzoate (354 mg, 2.34 mmol) in anhydrous DMSO (2.3 mL) was added 1,1'carbonyldiimidazole (569 mg, 3.51 mmol) was added at rt, under inert atmosphere. The resulting solution was stirred for 20 min at rt. In a separate flask containing barbituric acid (300 mg. 2.34 mmol) was added anhydrous 1,4-dioxane (7.8 mL), then heated to 50° C. Et$_3$N (522 μL, 3.74 mmol) was added and stirred for 15 min at 50° C. The isocyanate generated from methyl 4-aminobenzoate in DMSO was added to the stirring suspension, then heated to 80° C. until complete consumption of the starting materials were observed via LCMS (2 h). The reaction mixture was cooled to rt, then acidified with 6M HCl (aq), the precipitate formed was isolated, then triturated with MeOH, followed by acetonitrile, to yield the product as a off-white solid (342 mg, >99% purity, 48% yield).

¹H NMR (500 MHz, DMSO-d6+AcOD) δ 8.00-7.87 (m, 2H), 7.73-7.64 (m, 2H), 3.84 (s, 3H).

LCMS: m/z [M−1]⁻=304.07; R$_T$=2.33 min; purity=>99%.

HPLC conditions: Column: XTerra RP18, 3.5 μm, 3.0×50 mm; Gradient: 5% to 100% B in 2.5 minutes; 100% B for 1 minute; 1 mL/min; 4 min run. Eluent A: Milli-Q H₂O+ 0.1% Formic Acid; Eluent B: Acetonitrile+0.1% Formic Acid.

Step Two. 6-hydroxy-N-(4-(hydroxycarbamoyl)phenyl)-2,4-dioxo-1,2,3,4-tetrahydropyrimidine-5-carboxamide (PA2). PA1 (160 mg, 0.525 mmol) was added MeOH/CH₂Cl₂ (4.4 mL, 2:1 v/v) then cooled to 0° C. An aqueous solution of ammonium hydroxide (1.0 mL, 15.75 mmol. 50% in water), followed the addition of solid sodium hydroxide (210 mg, 5.25 mmol). The reaction mixture was then warmed up to rt, sealed and heated to 110° C. in the microwave for 10 min. After cooling to rt, the reaction mixture was acidified with 1M HCl (aq) then concentrated. The crude product was purified via ISCO (C18, 5 to 100% acetonitrile in water, with an ammonium formate buffer 10 mM, over 15 CV gradient) to yield the product (8) as an off-white solid (48.3 mg, 95.2% purity, 27% yield), after lyophilization.

¹H NMR (500 MHz, DMSO-d6+AcOD) δ 8.08 (br s, 4H).

LCMS: m/z [M−1]-=305.12; R$_T$=1.68 min; purity=95.2%.

HPLC conditions: Column: XTerra RP18, 3.5 μm, 3.0×50 mm; Gradient: 5% to 100% B in 2.5 minutes; 100% B for 1 minute; 1 mL/min; 4 min run. Eluent A: Milli-Q H₂O+ 0.1% Formic Acid; Eluent B: Acetonitrile+0.1% Formic Acid.

Figure 38:
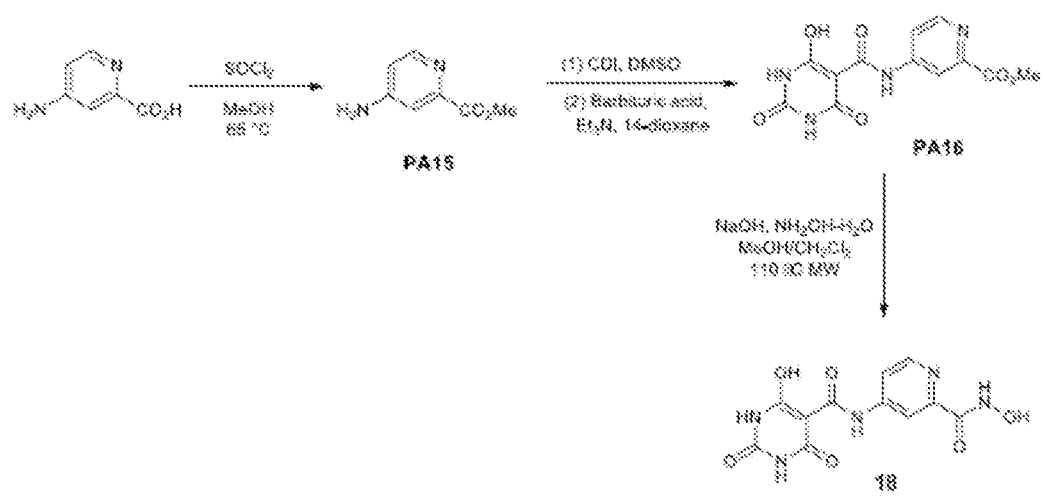
FIG. 38 illustrates a synthesis scheme for a compound having a structure represented by Formula (VIII$_b$), as described in Example 27.

Example 27: Preparation of 6-hydroxy-N-(2-(hydroxycarbamoyl)pyridin-4-yl)-2,4-dioxo-1,2,3,4-tetrahydropyrimidine-5-carboxamide (18, Formula (VIII$_b$), with Reference to FIG. 38)

Step One. Methyl 4-aminopicolinate (PA15). To the stirring solution of 4-aminopicolinic acid (600 mg, 4.34 mmol) in methanol (31 mL) at 0° C. was slowly added SOCl₂ (3.7 mL). The resulting reaction mixture was heated to reflux for 1 h, then concentrated to yield the titled compound as a white solid (467 mg, >98% purity, 71% yield) without further purification.

LCMS: m/z [M+1]⁺=152.92; R$_T$=0.48 min; purity=>99%.

HPLC conditions: Column: XTerra RP18, 3.5 μm, 3.0×50 mm; Gradient: 5% to 100% B in 2.5 minutes; 100% B for 1 minute; 1 mL/min; 4 min run. Eluent A: Milli-Q H₂O+ 0.1% Formic Acid; Eluent B: Acetonitrile+0.1% Formic Acid.

Step Two. Methyl 4-(6-hydroxy-2,4-dioxo-1,2,3,4-tetrahydropyrimidine-5-carboxamido)picolinate (PA16). PA16 was synthesized following general procedure 1. To a stirring solution of methyl 4-aminopicolinate PA15 (200 mg, 1.32 mmol) in anhydrous DMSO (1.3 mL) was added 1,1'carbonyldiimidazole (320 mg, 1.97 mmol) was added at rt, under inert atmosphere. The resulting solution was stirred for 20 min at rt. In a separate flask containing barbituric acid (169 mg. 1.32 mmol) was added anhydrous 1,4-dioxane (4.4 mL), then heated to 50° C. Et₃N (294 μL, 2.11 mmol) was added and stirred for 15 min at 50° C. The isocyanate generated from methyl 4-aminobenzoate in DMSO was added to the stirring suspension, then heated to 80° C. until complete consumption of the starting materials were observed via LCMS (1 h). The reaction mixture was cooled to rt, then acidified with 6M HCl (aq), the precipitate formed was isolated, then triturated with MeOH, followed by acetonitrile, to yield the product as an off-white solid (218 mg, >99% purity, 54% yield).

¹H NMR (500 MHz, DMSO-d⁶) δ 12.48 (s, 1H), 8.88 (s, 1H), 8.41 (d, J=5.4 Hz, 1H), 8.26 ((d, J=1.8 Hz, 1H), 7.63 (ddc, J=5.6, 1.7 Hz, 1H), 7.59 (s, 2H), 3.86 (s, 3H).

LCMS: m/z [M+1]⁺=307.17; R$_T$=1.48 min; purity=>99%.

HPLC conditions: Column: XTerra RP18, 3.5 μm, 3.0×50 mm; Gradient: 5% to 100% B in 2.5 minutes; 100% B for 1 minute; 1 mL/min; 4 min run. Eluent A: Milli-Q H₂O+ 0.1% Formic Acid; Eluent B: Acetonitrile+0.1% Formic Acid.

Step Three. 6-hydroxy-N-(2-(hydroxycarbamoyl)pyridin-4-yl)-2,4-dioxo-1,2,3,4-tetrahydropyrimidine-5-carboxamide (18). PA16 (134 mg, 0.438 mmol) was added MeOH/CH₂Cl₂ (3.7 mL, 2:1 v/v) then cooled to 0° C. An aqueous solution of ammonium hydroxide (2.6 mL, 15.75 mmol. 50% in water), followed the addition of solid sodium hydroxide (175 mg, 4.38 mmol). The reaction mixture was then warmed up to rt, sealed and heated to 110° C. in the microwave for 20 min. After cooling to rt, the reaction mixture was acidified with 1M HCl (aq) then concentrated. The crude product was purified via ISCO (C18, 5 to 100% acetonitrile in water, with an ammonium formate buffer 10 mM, over 15 CV gradient) to yield the product (18) as an off-white solid (7.8 mg, 97.8% purity, 6% yield), after lyophilization.

¹H NMR (500 MHz, DMSO-d6+DCl in D₂O) δ 8.59 (d, J=6.7 Hz, 1H), 8.33 (d, J=1.7 Hz, 1H), 8.20 (d, J=6.7 Hz, 1H).

LCMS: m/z [M+1]⁺=308.52; R$_T$=0.19 min; purity=>99%.

HPLC conditions: Column: XBridge C18, 3.5 μm, 4.6×30 mm; Iso 5% B for 0.2 min, 5% to 100% B in 1.8 minutes; hold 100% B for 1 minute, run time=3.0 min; Flow=3 mL/min; Eluents: A=-Q H2O+10 mM Ammonium Bicarbonate pH: 10; B=MeCN.

Figure 39:
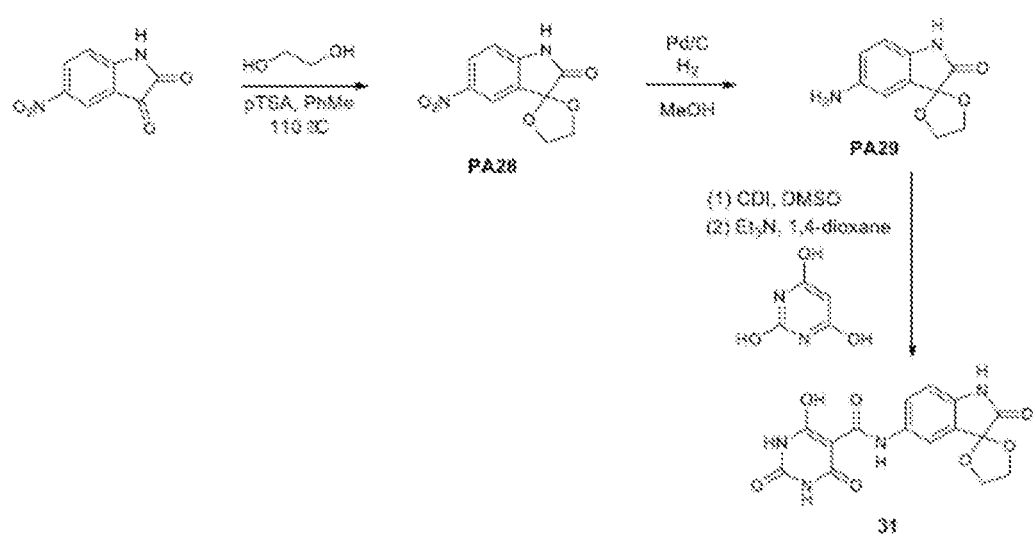
FIG. 39 illustrates a synthesis scheme for a compound having a structure represented by Formula (IV$_c$), as described in Example 28.

Example 28: Preparation of 2,4,6-trihydroxy-N-(2'-oxospiro[[1,3]dioxolane-2,3'-indolin]-6'-yl)pyrimidine-5-carboxamide (31, Formula (IV$_c$), with Reference to FIG. 39)

Step One. 5'-Nitrospiro[[1,3]dioxolane-2,3'-indolin]-2'-one (PA28). A solution of 5-aminoisatin (500 mg, 2.60 mmol) and ethylene glycol (290 μL, 5.20 mmol) in toluene (5.2 mL, 0.5 M) was added p-toluenesulfonic acid monohydrate (25 mg, 0.13 mmol). The reaction mixture was heated to 100° C. equipped with a Dean-Stark apparatus for 20 h, until consumption of starting material was observed by LCMS. The reaction was then allowed to cool to room temperature; the precipitate formed was collected by vacuum filtration, washed with toluene (10 mL), then dried under high vacuum to yield the product as a brown solid (573 mg, 93% yield).

LCMS: m/z [M+1]⁺=237.05; R$_T$=1.24 min; purity=>99%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H₂O+10 mM ammonium formate pH: 3.8; Eluent B: Acetonitrile.

Step Two. 5'-Aminospiro[[1,3]dioxolane-2,3'-indolin]-2'-one (PA29). PA28 (466 mg, 1.97 mmol) dissolved in MeOH (39 mL, 0.05 M) was added palladium on charcoal (500 mg, 10 wt. %), the reaction was evacuated and purged with hydrogen gas (5×), then allowed to stir under hydrogen (1 atm, balloon) at room temperature, until complete consumption of starting material was observed by LCMS. The reaction mixture was then filtered through a small pad of celite, washed with methanol (20 mL), then the filtrate was collected and concentrated to yield the product as a brown solid (406 mg, 100% yield) without further purification.

$^1$H NMR (500 MHz, MeOD) δ 6.79 (d, J=2.2 Hz, 1H), 6.72 (dd, J=8.2, 2.3 Hz, 1H), 6.64 (d, J=8.2 Hz, 1H), 4.49-4.41 (m, 2H), 4.31-4.23 (m, 2H).

LCMS: m/z [M+1]$^+$=207.12; R$_T$=0.33 min; purity=>99%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. 6-Hydroxy-2,4-dioxo-N-(2'-oxospiro[[1,3]dioxolane-2,3'-indolin]-5'-yl)-1,2,3,4-tetrahydropyrimidine-5-carboxamide (31). Compound 31 was synthesized following the General Procedure 1. To a stirring solution of aminospiro [[1,3]dioxolane-2,3'-indolin]-2'-one (PA29) (87 mg, 0.422 mmol) in anhydrous DMSO (420 µL, 1.0 M) was added 1,1'carbonyldiimidazole (103 mg, 0.633 mmol) was added at rt, under inert atmosphere. The resulting solution was stirred for 20 min at rt. In a separate flask containing barbituric acid (54 mg, 0.422 mmol) was added anhydrous 1,4-dioxane (1.4 mL, 0.30 M), then heated to 55° C. Et$_3$N (94 µL, 0.675 mmol) was added and stirred for 15 min at 55° C. The isocyanate generated from the amine in DMSO was added to the stirring suspension, then heated to 80° C. until complete consumption of the starting materials were observed via LCMS (2 h). The reaction mixture was cooled to rt, then acidified with 6M HCl (aq), the precipitate formed was isolated, then triturated with water, MeOH, followed by acetonitrile. The crude product was further purified by reverse-phase chromatography (C18, gradient eluent from 0 to 100% acetonitrile in water with 10 mM ammonium formate buffer over 20 CV) to yield the product (31) as a pinkish-brown solid (52 mg, 34% yield), after lyophilization.

$^1$H NMR (500 MHz, DMSO-δ6) δ 11.99 (s, 1H), 9.58 (s, 1H), 7.73 (s, 1H), 7.27 (d, J=7.6 Hz, 1H), 6.70 (d, J=8.3 Hz, 1H), 4.34 (dd, J=8.2, 4.9 Hz, 2H), 4.25 (dd, J=8.5, 5.1 Hz, 2H).

LCMS: m/z [M-1]-=359.06; R$_T$=0.97 min; purity=96.1%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 40:
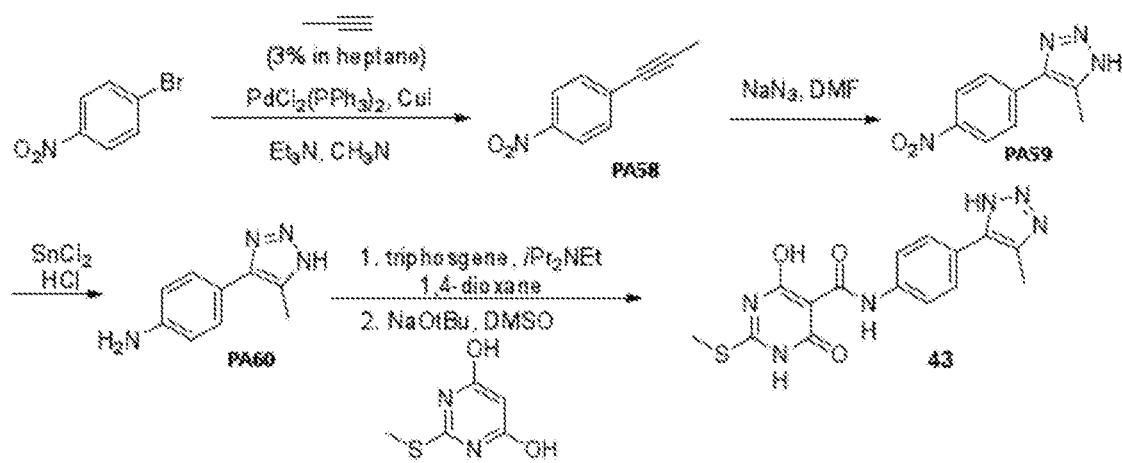
FIG. 40 illustrates a synthesis scheme for a compound having a structure represented by Formula (II$_g$), as described in Example 29.

Example 29: Preparation of 4-hydroxy-N-(4-(4-methyl-1H-1,2,3-triazol-5-yl)phenyl)-2-(methylthio)-6-oxo-1,6-dihydropyrimidine-5-carboxamide (43, Formula (II$_g$), with Reference to FIG. 40)

Step One. 1-Nitro-4-(prop-1-yn-1-yl)benzene (PA58). A round bottom flask containing 1-bromo-4-nitrobenzene (1.00 g, 4.95 mmol), PdCl$_2$(PPh$_3$)$_2$ (174 mg, 0.248 mmol), and CuI (47 mg, 0.248 mmol) was purged with nitrogen for 15 min. Anhydrous acetonitrile (2.5 mL) was added, followed by propyne in heptane (13.2 mL, 99.0 mmol, 3% in heptane) and Et$_3$N (1.4 mL, 9.90 mmol). The reaction mixture was sealed and allow to stir at rt for 20 h. The reaction mixture was then concentrated, diethyl ether was added, then filtered through a small pad of Celite. The filtrate was concentrated then purified via ISCO (SiO$_2$, gradient eluent from 0 to 25% ethyl acetate in hexanes over 20 CV) to yield the product as a yellow solid (645 mg, >99% purity, 81% yield).

R$_f$: 0.79 (25% ethyl acetate in hexanes).

LCMS: R$_T$=1.73 min: purity=>99%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Two. 5-Methyl-4-(4-nitrophenyl)-1H-1,2,3-triazole (PA59). Sodium azide (111 mg, 1.71 mmol) was added to PA58 (229 mg, 1.42 mmol) dissolved in anhydrous DMF (7.1 mL) at rt. The reaction was sealed in a pressure vessel and heated to 120° C. for 18 h. The reaction mixture was then allowed to warm up to rt, dichloromethane was added, followed by water. The aqueous layer was extracted with dichloromethane (3×20 mL), the combined organic extract was washed with brine, dried over MgSO$_4$, then concentrated under reduced pressure to yield the product as a brown solid (180 mg, >99% purity, 62% yield), without further purification.

LCMS: m/z [M+1]$^+$=205.29; R$_T$=1.29 min; purity=>99%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. 4-(5-Methyl-1H-1,2,3-triazol-4-yl)aniline (PA60). Tin (II) chloride (938 mg, 4.51 mmol) was added to PA59 (230 mg, 1.13 mmol) in EtOH (3.8 mL) and conc. HCl (710 µL) at rt, the resulting reaction mixture was heated to reflux for 1 h. After complete consumption of the starting material was observed via LCMS, the reaction was allowed to cool to rt, before pouring into a solution of K$_3$PO$_4$ (~1.0 g) in MeOH (10 mL) at rt. The resulting reaction was stirred at rt for 30 min until the pH is not longer acidic. The precipitate was filtered, washed with additional methanol. The filtrate was collected and concentrated under reduced pressure. The crude product was purified via ISCO (SiO$_2$, gradient eluent from 0 to 15% methanol in dichloromethane over 12 CV) to yield the product as a brown oil (69 mg, 35% yield).

LCMS: m/z [M+1]$^+$=175.42; R$_T$=0.83 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Four. 4-hydroxy-N-(4-(4-methyl-1H-1,2,3-triazol-5-yl)phenyl)-2-(methylthio)-6-oxo-1,6-dihydropyrimidine-5-carboxamide (43). 43 was synthesized following general procedure 2. 2-(Methylthio)pyrimidine-4,6-diol (171 mg, 1.08 mmol) was added to a stirring solution of sodium tert-butoxide (104 mg, 1.08 mmol) dissolved in DMSO (2.7 mL) at rt for 5 min. In a separate flask, aniline PA60 was dissolved in 1,4-dioxane (680 mL), to this solution was added triphosgene (53 mg, 0.178 mmol) in one-portion. The suspension was stirred vigorously for 2 min at rt, then iPr$_2$NEt (190 µL) was added. The suspension was stirred vigorously at rt for 2 min. Freshly prepared solution of sodium 6-hydroxy-2-(methylthio)pyrimidin-4-olate in DMSO was added to the suspension in one-portion. The reaction was stirred at 90° C. for 30 min, until complete consumption of starting material observed via LCMS. The reaction mixture was loaded directly on C18 column and purified via reverse-phase chromatography (gradient eluent from 0 to 100% acetonitrile in water with an ammonium formate buffer 10 mM over 20 CV) to yield the product (43) as brown solid (29.2 mg, 97.7% purity, 15% yield), after lyophilization.

¹H NMR (400 MHz, DMSO-d⁶) δ 7.69 (br s, 4H), 2.44 (s, 3H), 2.37 (s, 3H).

LCMS: m/z [M+1]⁺=359.0; $R_T$=1.37 min; purity=97.7%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H₂O+10 mM ammonium formate pH: 3.8; Eluent B: Acetonitrile.

Figure 41:
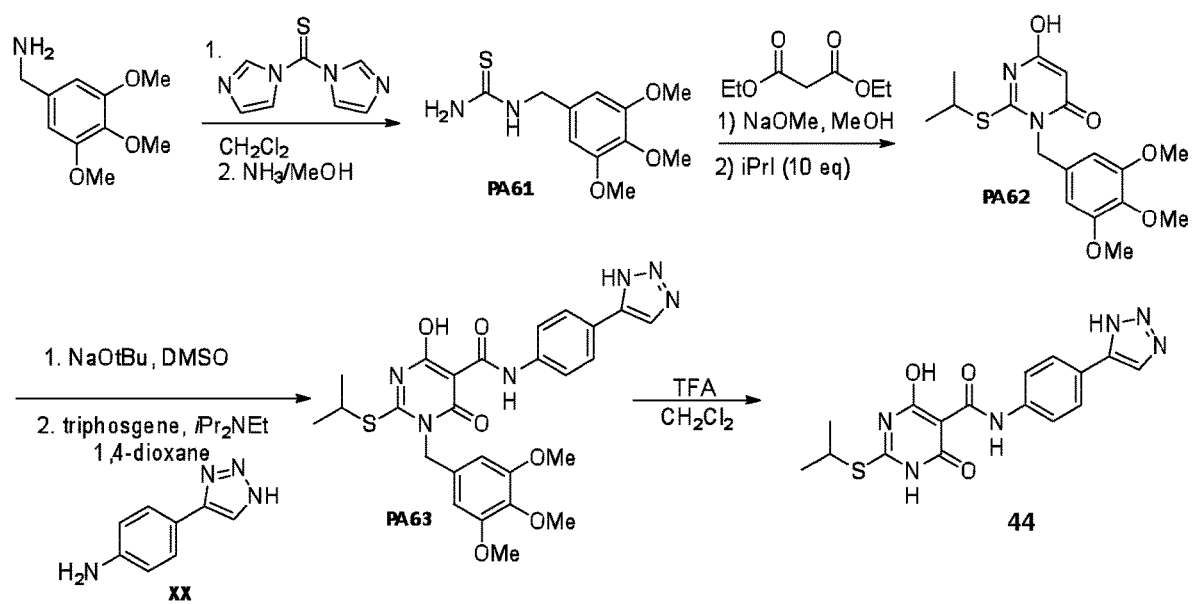
FIG. 41 illustrates a synthesis scheme for a compound having a structure represented by Formula (II$_d$), as described in Example 30.

Example 30: Preparation of N-(4-(1H-1,2,3-triazol-5-yl)phenyl)-4-hydroxy-2-(isopropylthio)-6-oxo-1,6-dihydropyrimidine-5-carboxamide (44, Formula (II$_d$), with Reference to FIG. 41)

Step One. 1-(3,4,5-trimethoxybenzyl)thiourea (PA61). (3,4,5-Trimethoxyphenyl)methanamine (2.5 mL, 14.6 mmol) was added dropwise to a solution of 1,1'-thiocarbonyl diimidazole (3.91 g, 22.0 mmol) dissolved in dichloromethane (36.5 mL) at 0° C. The reaction mixture was then allowed to warm up to rt over 2 h. After complete consumption of the starting material was observed via LCMS, a solution of ammonia in methanol (7.5 mL, 52.6 mmol, 7.0 M in MeOH) was added, then stirred for an additional 20 h. The reaction mixture was concentrated under reduced pressure, dichloromethane was added, the precipitate was isolated and washed with additional CH₂Cl₂, then dried under high vacuum to yield the product as a light pink solid (2.83 g, 76% yield).

LCMS: m/z [M+1]⁺=257.07; $R_T$=1.06 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H₂O+10 mM ammonium formate pH: 3.8; Eluent B: Acetonitrile.

Step Two. 6-hydroxy-2-(isopropylthio)-3-(3,4,5-trimethoxybenzyl)pyrimidin-4(3H)-one (PA62). A mixture of PA61 (781 mg, 3.05 mmol), diethyl malonate (465 µL, 3.05 mmol), and NaOMe (1.4 mL, 6.10 mmol, 4.4 M in MeOH) in methanol (2.4 mL) was heated to reflux for 3 h. The reaction was then cooled to −50° C., isopropyl iodide (3.5 mL, 30.5 mmol) was then added in one-portion. The reaction was stirred for an additional 30 min at 50° C. The reaction mixture was then cooled to rt, then concentrated under reduced pressure. The crude product was purified via reverse-phase chromatography (gradient eluent from 0 to 100% acetonitrile in water with an ammonium formate buffer 10 mM over 15 CV) to yield the product as a white solid (433 mg, 97.7% purity, 38% yield), after lyophilization.

LCMS: m/z [M+1]⁺=367.02; $R_T$=1.41 min; purity=97.7%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H₂O+10 mM ammonium formate pH: 3.8; Eluent B: Acetonitrile.

Step Three. N-(4-(1H-1,2,3-triazol-5-yl)phenyl)-4-hydroxy-2-(isopropylthio)-6-oxo-1-(3,4,5-trimethoxybenzyl)-1,6-dihydropyrimidine-5-carboxamide (PA63). PA63 was synthesized following general procedure 2. PA62 (97 mg, 0.265 mmol) was added to a stirring solution of sodium tert-butoxide (25 mg, 0.265 mmol) dissolved in DMSO (870 µL) at rt for 5 min. In a separate flask, aniline XX was dissolved in 1,4-dioxane (220 µL), to this solution was added triphosgene (17 mg, 0.0578 mmol) in one-portion. The suspension was stirred vigorously for 2 min at rt, then iPr₂NEt (60 µL) was added. The suspension was stirred vigorously for 2 min. Freshly prepared solution of sodium 6-hydroxy-2-(isopropylthio)-3-(3,4,5-trimethoxybenzyl)pyrimidin-4(3H)-olate in DMSO was added to the suspension in one-portion. The reaction was stirred at 90° C. for 30 min, until complete consumption of starting material observed via LCMS. The reaction mixture was loaded directly on C18 column and purified via reverse-phase chromatography (gradient eluent from 30 to 100% acetonitrile in water with an ammonium formate buffer 10 mM over 15 CV) to yield the product as brown solid (31.2 mg, 80.2% purity, 26% yield), after lyophilization.

LCMS: m/z [M+1]⁺=552.9; $R_T$=1.80 min; purity=80.2%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H₂O+10 mM ammonium formate pH: 3.8; Eluent B: Acetonitrile.

Step Four. N-(4-(1H-1,2,3-triazol-5-yl)phenyl)-4-hydroxy-2-(isopropylthio)-6-oxo-1,6-dihydropyrimidine-5-carboxamide (44). A solution of PA63 (31.2 mg, 0.0452 mmol, 80% purity) in dichloromethane (1.5 mL) was added trifluoroacetic acid (270 µL). The resulting reaction mixture was sealed in a pressure vessel then heated to 60° C. for 20 h. The reaction mixture was allowed to cool to rt, then concentrated under reduced pressure. The crude product was co-evaporated several times with methanol (3×), then purified via reverse-phase chromatography (C18, gradient eluent from 30 to 100% acetonitrile in water with an ammonium formate buffer 10 mM over 20 CV) to yield the product (44) as an off-white solid (6.0 mg, 98.6% purity, 35% yield), after lyophilization.

¹H NMR (400 MHz, DMSO-d6+AcOD) δ 8.23 (s, 1H), 7.87 (d, J=8.2 Hz, 2H), 7.68 (d, J=8.2 Hz, 2H), 3.92 (dt, J=13.7, 6.9 Hz, 1H), 1.36 (d, J=6.9 Hz, 6H).

LCMS: m/z [M+1]⁺=373.1; $R_T$=1.49 min; purity=98.6%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H₂O+10 mM ammonium formate pH: 3.8; Eluent B: Acetonitrile.

Figure 42:
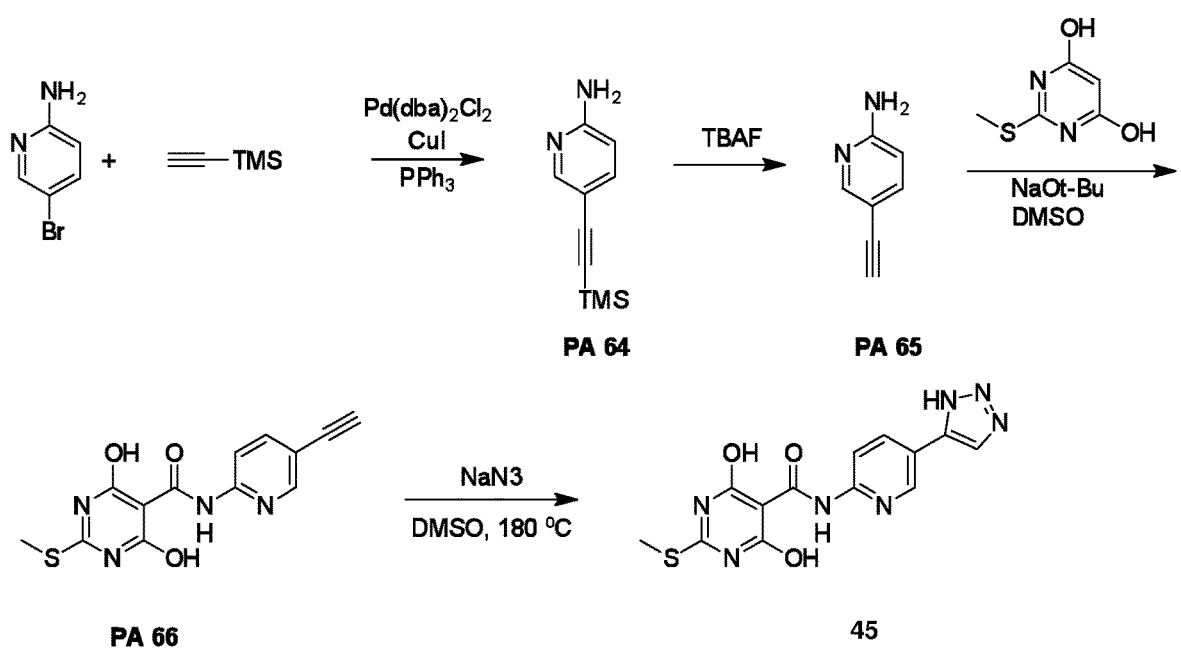
FIG. 42 illustrates a synthesis scheme for a compound having a structure represented by Formula (II$_e$), as described in Example 31.

Example 31: Preparation of N-(5-(1H-1,2,3-triazol-5-yl)pyridin-2-yl)-4,6-dihydroxy-2-(methylthio)pyrimidine-5-carboxamide (45, Formula (I$_e$), with Reference to FIG. 42)

Step One. 5-((Trimethylsilyl)ethynyl)pyridin-2-amine (PA64). To a sealed tube was added 2-amino-5-bromopyridine (1.00 g, 5.8 mmol), Pd(dba)₂C12 (202 mg, 0.29 mmol), PPh₃ (151 mg, 0.58 mmol), CuI (110 mg, 0.578 mmol), Et₃N (10 mL) and TMS-acetylene (963 mg, 9.8 mmol) sequentially. The mixture was degassed and heated at 85° C. for 2 h. After complete consumption of starting material was observed via LCMS, the solvent was removed in vacuo and the crude was purified over silica (gradient eluent from 0 to 100% ethyl acetate in hexanes). PA64 was obtained as beige solid (812 mg, 74% yield).

LCMS: m/z [M+1]⁺=191.3; $R_T$=1.55 min

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H₂O+10 mM ammonium formate pH: 3.8; Eluent B: Acetonitrile.

Step Two. 5-Ethynylpyridin-2-amine (PA65). PA64 (500 mg, 2.6 mmol) was dissolved in THF (5 mL) and to this solution was added TBAF (5 mL, 1 M in THF). The reaction was stirred at rt for 10 min and THF was removed in vacuo. The crude was dissolved in EtOAc and this solution was passed through a pad of silica and washed with EtOAc. The filtrate was concentrated to yield PA65 as beige solid (256 mg, 82% yield).

LCMS: m/z [M+1]$^+$=118.8; R$_T$=0.41 min.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Three. N-(5-Ethynylpyridin-2-yl)-4,6-dihydroxy-2-(methylthio)pyrimidine-5-carboxamide (PA66). t-BuONa (136 mg, 1.4 mmol) was dissolved in DMSO (2 mL) and to this solution was added 2-(methylthio)pyrimidine-4,6-diol (224 mg, 1.4 mmol). The solution was stirred at rt for 5 min and left aside for the second step. At the same time, PA65 (84 mg, 0.71 mmol) was dissolved in DCE (1 mL) and to the solution was added CDI (115 mg, 0.71 mmol) in one-portion. The suspension was stirred vigorously for 2 min at rt and iPr$_2$NEt (250 uL, 1.4 mmol) was added. The solution was stirred at rt vigorously for 2 min. Freshly prepared solution of sodium 6-hydroxy-2-(methylthio)pyrimidin-4-olate in DMSO was added to the suspension. The reaction was stirred at 90° C. for 30 min. DCE solvent was removed in vacuo and the product was isolated by ISCO (120 g C18 column, gradient eluent from 0 to 50% acetonitrile in water with an ammonium bicarbonate buffer 10 mM over 20 CV). Product elutes at 35% MeCN in water. The product was isolated as a beige solid (62 mg, 29% yield), after lyophilization.

LCMS: m/z [M+1]$^+$=303.0; R$_T$=1.59 min HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Four. N-(5-(1H-1,2,3-triazol-5-yl)pyridin-2-yl)-4,6-dihydroxy-2-(methylthio)pyrimidine-5-carboxamide (45). PA66 (62 mg, 0.21 mmol) was dissolved in DMSO (2 mL) and to this solution was added NaN$_3$ (67 mg, 1.0 mmol). The mixture was stirred at 180° C. for 30 min. The product was purified by ISCO (60 g C18 column, gradient eluent from 0 to 50% acetonitrile in water with an ammonium bicarbonate buffer 10 mM over 20 CV, product elutes at 22% MeCN in water). The product (45) was isolated as an off-white solid (25 mg, 35% yield), after lyophilization.

1HNMR (500 MHz, DMSO-d$^6$, DCl) δ 12.11 (s, 1H), 8.88 (dd, J=2.4, 0.8 Hz, 1H), 8.45 (s, 1H), 8.33 (dd, J=8.6, 2.4 Hz, 1H), 8.22 (dd, J=8.7, 0.8 Hz, 1H), 2.56 (s, 3H).

LCMS: m/z [M−1]$^−$=346.0; R$_T$=1.29 min; purity=94.4%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 43:
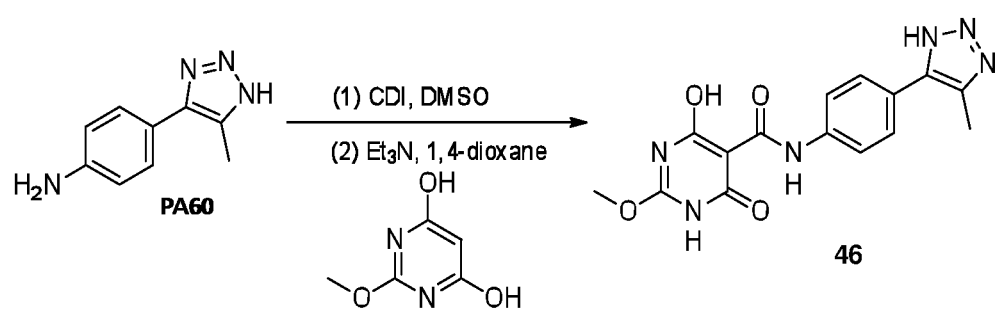
FIG. 43 illustrates a synthesis scheme for a compound having a structure represented by Formula (II$_h$), as described in Example 32.

Example 32: Preparation of 4-hydroxy-2-methoxy-N-(4-(4-methyl-1H-1,2,3-triazol-5-yl)phenyl)-6-oxo-1,6-dihydropyrimidine-5-carboxamide (46, Formula (II$_h$), with Reference to FIG. 43)

46 was synthesized following general procedure 1. To a stirring solution of PA60 (23 mg, 0.132 mmol) in anhydrous DMSO (130 µL) was added 1,1'carbonyldiimidazole (33 mg, 0.198 mmol) was added at rt, under inert atmosphere. The resulting solution was stirred for 20 min at rt. In a separate flask containing 2-methoxypyrimidine-4,6-diol (21 mg, 0.145 mmol) was added anhydrous 1,4-dioxane (440 µL), then heated to 50° C. Et$_3$N (29 µL, 0.211 mmol) was added and stirred for 15 min at 50° C. The isocyanate generated from the amine in DMSO was added to the stirring suspension, then heated to 80° C. until complete consumption of the starting materials were observed via LCMS (30 min). The reaction mixture was cooled to rt, then acidified with 6M HCl (aq), the reaction mixture was directly loaded onto a C18 column and purified via ISCO (gradient eluent from 0 to 50% acetonitrile in water with an ammonium bicarbonate buffer 10 mM over 20 CV) to yield the product (46) as an off-white solid (1.6 mg, 97.0% purity, 4% yield), after lyophilization.

$^1$H NMR (400 MHz, DMSO-d$^6$) δ 8.14 (s, 1H), 7.69 (s, 4H), 3.79 (s, 3H), 2.44 (s, 3H).

LCMS: m/z [M+1]$^+$=342.7; R$_T$=1.24 min; purity=97.0%.

HPLC conditions: Column: XBridge C18, 3.5 µm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Figure 44:
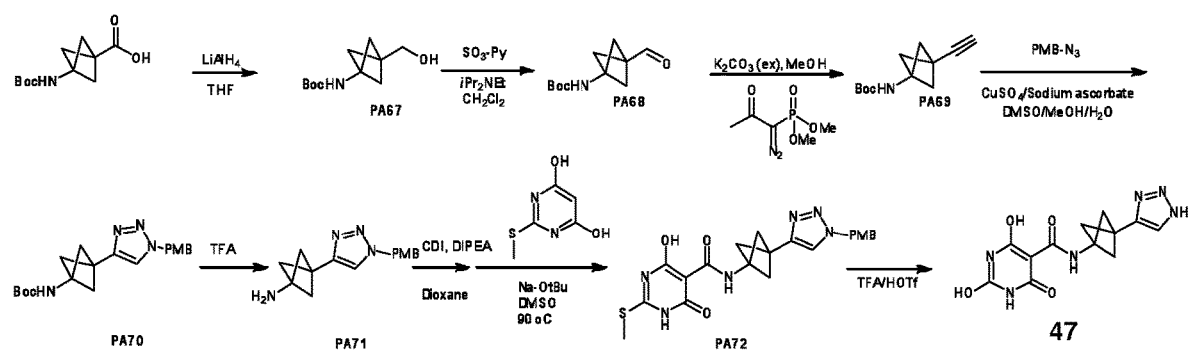
FIG. 44 illustrates a synthesis scheme for a compound having a structure represented by Formula (II$_f$), as described in Example 33.

Example 33: Preparation of N-(3-(1H-1,2,3-triazol-4-yl)bicyclo[1.1.1]pentan-1-yl)-2,4-dihydroxy-6-oxo-1,6-dihydropyrimidine-5-carboxamide (47, Formula (II$_f$), with Reference to FIG. 44)

Step One. tert-Butyl (3-(hydroxymethyl)bicyclo[1.1.1]pentan-1-yl)carbamate (PA67). 3-((Tert-butoxycarbonyl)amino)bicyclo[1.1.1]pentane-1-carboxylic acid (600 mg, 2.6 mmol) was added to THF (25 mL). The solution was cooled to 0° C. under N$_2$. To the solution was added LiAH$_4$ (401 mg, 10.6 mmol) under N$_2$. The reaction was warmed up to rt and stirred for 1 h. Na$_2$SO$_4$ decahydrate (500 mg) was added slowly to the reaction and the reaction was diluted with EtOAc (30 mL). The precipitate was filtered and the filtrate was concentrated in vacuo to yield crude PA67 (420 mg, 75% yield), which was used without purification.

1HNMR (500 MHz, CDCl$_3$) δ 3.7 (s, 2H), 1.94 (s, 6H), 1.44 (s, 9H).

Step Two. tert-Butyl (3-formylbicyclo[1.1.1]pentan-1-yl)carbamate (PA68). SO$_3$—Pyridine (500 mg, 3.1 mmol) was added portion wise (small exotherm) to a solution of DMSO (1.2 g, 15 mmol), PA67 (335 mg, 1.6 mmol) and iPr$_2$Net (811 mg, 6.3 mmol) in CH$_2$Cl2 (6 mL) at rt. The reaction was stirred for 20 min at rt. The reaction mixture was diluted with CH$_2$Cl2 (30 mL). The reaction was then washed with sat. NaHCO$_3$ (10 mL), brine (10 mL) and dried over MgSO$_4$ and concentrated in vacuo. The crude PA68 was used in the next step, without further purification.

1HNMR (500 MHz, CDCl$_3$) δ 9.66 (s, 1H), 2.29 (s, 6H), 1.44 (s, 9H).

Step Three. tert-butyl (3-ethynylbicyclo[1.1.1]pentan-1-yl)carbamate (PA69). PA68 (80 mg, 0.38 mmol) was dissolved in dry MeOH/THF (2 mL, 1:1 v/v, dried over MgSO$_4$ overnight). To the solution was added K$_2$CO$_3$ (105 mg, 0.76 mmol) and dimethyl diazo-2-oxopropylphosphonate (95 mg, 0.49 mmol). The mixture was stirred overnight. ISCO purification was performed (dry loading with silica, gradient eluent from 0 to 50% ethyl acetate in hexanes) to yield the desired product, PA69 (42 mg, 53% yield).

1HNMR (500 MHz, CDCl$_3$) δ 2.29 (s, 6H), 2.10 (s, 1H), 1.25 (s, 9H).

Step Four. tert-butyl (3-(1-(4-methoxybenzyl)-1H-1,2,3-triazol-4-yl)bicyclo[1.1.1]pentan-1-yl)carbamate (PA70). CuSO$_4$ (263 mg in 3 mL water, 1.6 mmol) was added to sodium ascorbate (390 mg in 3 mL water, 2.0 mmol). The solution was stirred at rt for 1 min and DMSO (8 mL) was added to the mixture. The suspension was added to PA69 (70 mg, 0.33 mmol) and PMB-N$_3$ (161 mg, 0.99 mmol) mixture in 4 mL MeOH. The resulting mixture was stirred at rt for 30 min. The precipitate was filtered by Celite and washed with methanol. The filtrate was concentrated to remove MeOH and the product was extracted with EtOAc/H$_2$O (40 mL/20 mL). The organic layer was washed with brine and dried over MgSO$_4$, then concentrated in vacuo to give the crude product. The crude product was purified by silica pad, (30% ethyl acetate in hexanes to remove the excess azide. The product was flushed out by 1/1 MeOH/DCM) to yield the desired product (115 mg, 95% yield).

LCMS: m/z [M+1]$^+$=371.1; RT=1.61 min

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Five. 3-(1-(4-methoxybenzyl)-1H-1,2,3-triazol-4-yl) bicyclo[1.1.1]pentan-1-amine (PA71). PA70 (80 mg, 0.22 mol) was dissolved in TFA (4 mL) and the reaction was stirred at rt for 30 min. Removal of the solvent in vacuo and the crude was dissolved in EtOAc (30 mL). The organic layer was washed with sat. aqueous Na$_2$CO$_3$ (10 mL) and brine (10 mL). The organic layer was then dried over MgSO$_4$ and the solvent was removed in vacuo to yield the crude product (58 mg, 99% yield).

LCMS: m/z [M+1]$^+$=271.0; R$_T$=1.08 min

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Step Six. 4-Hydroxy-N-(3-(1-(4-methoxybenzyl)-1H-1,2,3-triazol-4-yl)bicyclo[1.1.1]pentan-1-yl)-2-(methylthio)-6-oxo-1,6-dihydropyrimidine-5-carboxamide (PA72). PA71 (57 mg, 0.21 mmol) was dissolved in dioxane (0.3 mL). To this solution was added CDI (45 mg, 0.27 mmol), the reaction was stirred at rt for 3 min and iPr$_2$NEt (82 mg, 0.63 mmol) was added. The solution was stirred at rt for 10 min. To this solution was added freshly prepared 2-(methylthio) pyrimidine-4,6-diol (100 mg, 0.63 mmol) with NaOt-Bu (61 mg, 0.63 mmol) in DMSO (1 mL). The mixture was heated up to 90° C. for 1 h until complete consumption of the starting material was observed by LCMS. The crude product was then purified by ISCO (gradient eluent from 0 to 100% acetonitrile in water with an ammonium bicarbonate buffer 10 mM, product eluted at 35% MeCN in water) to yield the product (42 mg, 44% yield), after lyophilization.

LCMS: m/z [M+1]$^+$=455.1; R$_T$=1.54 min

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile Step Seven. N-(3-(1H-1,2,3-Triazol-4-yl)bicyclo[1.1.1] pentan-1-yl)-2,4-dihydroxy-6-oxo-1,6-dihydropyrimidine-5-carboxamide (47). PA72 (20 mg, 0.044 mmol) was dissolved in TFA (4 mL) and TfOH (0.2 mL) was added. The reaction mixture was heated at 85° C. for 4 h. To the reaction was added 0.3 mL iPr$_2$NEt (To prevent decomposition caused by TfOH) and the reaction was concentrated in vacuo. The crude product was purified by ISCO (gradient eluent from 0 to 100% acetonitrile in water with an ammonium bicarbonate buffer 10 mM over 15 CV) to yield the product (47) as a white solid (27 mg, 87% yield).

1HNMR (500 MHz, DMSO-d$^6$, TFA) δ 9.91 (s, 1H), 7.74 (s, 1H), 2.55 (s, 3H), 2.45 (s, 6H).

LCMS: m/z [M+1]$^+$=334.9; R$_T$=1.23 min; purity=97.0%.

HPLC conditions: Column: XBridge C18, 3.5 μm, 4.6×30 mm; Gradient: 5% B for 0.2 min, 5% to 100% B in 1.8 min; 100% B for 1 min; 3 mL/min. Eluent A: Milli-Q H$_2$O+10 mM ammonium formate pH: 3.8; Eluent B: Acetonitrile.

Example 34: Bioactivity Assays

The biological activities of compounds having structures represented by any of Formulae (I)—(VII), were evaluated in two assays: xanthine oxidase activity and URAT1 activity.

Xanthine oxidase inhibition was determined using a standard fluorescence-based assay for xanthine oxidase activity (McHale A, Grimes H, Coughlan M P: Int J Biochem. 10:317-9, 1979) with minor variations. The procedure was internally standardized using allopurinol and DPI as controls for all experiments after determination of their optimal inhibitory concentrations. Experiments on test compounds were performed in triplicate in multi-well plates using 10 concentrations of each compound that ranged over a 3-fold dilution.

URAT1 (SLC22A12) activity was evaluated in a cellular uptake assay using a 96-well plate with stably transfected URAT-1/CHO cells. $^3$H-orotate was used as the test transport agent, which was measured in a liquid scintillation counter, using benzbromarone as a positive control, and DMSO and non-transfected CHO cells as negative controls (Solvo Biotechnology, Boston, Mass.). Generally determined over 7 concentrations (range, 0.01 to 150 M), a semi-log plot (percent relative transport of oratate vs. time) was generated to determine the concentration at which 50% inhibition was observed (i.e., the IC50).

The results of these assays for compounds according to Formula (I) are shown in Table 1:

TABLE 1

| Compound | URAT1 IC50 (μM) | Xanthine Oxidase IC50 (μM) |
|---|---|---|
| Formula (I$_a$) | >4.8 | 0.25 |
| Formula (I$_b$) |  | 54.1 |
| Formula (I$_c$) | >150 | 1.2 |
| Formula (I$_d$) |  | >300 |
| Formula (I$_e$) | >37.5 | 1.6 |
| Formula (I$_f$) | >9 | 0.20 |
| Formula (I$_g$) | >150 | 0.55 |
| Formula (I$_h$) | >18.8 | 0.74 |
| Formula (I$_i$) |  | >295.8 |
| Formula (I$_j$) |  | 13.1 |
| Formula (I$_k$) |  | 1.3 |
| Formula (I$_l$) |  | 6.3 |
| Formula (I$_m$) |  | 18.2 |
| Formula (I$_n$) |  | 292 |
| Allopurinol | >300$^†$ | 2.0 to 5.0 |
| Lesinurad | 18.61* 52.5 ± 5.9$^{†*}$ | >300$^†$ |

$^†$Presentation estimate; Proc. EULAR Abstract #THU0357, 2008
*URAT1 assay as described herein The results of these assays for compounds according to Formula (II) are shown in Table 2:

TABLE 2

| Compound | URAT1 IC50 (μM) | Xanthine Oxidase IC50 (μM) |
|---|---|---|
| Formula (II$_a$) |  | 9.2 |
| Formula (II$_b$) | 12.1 | 0.56 |
| Formula (II$_c$) | 2.4 | 0.05 |
| Formula (II$_d$) | 1.07 | ≤0.02 |
| Formula (II$_e$) | >9.45 | 0.025 |
| Formula (II$_f$) |  | 217 |
| Formula (II$_g$) |  | 2.8 |

TABLE 2-continued

| Compound | URAT1 IC50 (μM) | Xanthine Oxidase IC50 (μM) |
|---|---|---|
| Formula (II$_h$) | | 1.8 |
| Allopurinol | >300† | 2.0 to 5.0 |
| Lesinurad | 18.61* | >300† |
| | 52.5 ± 5.9†* | |

The results of these assays for compounds according to Formula (III) are shown in Table 3:

TABLE 3

| Compound | URAT1 IC50 (μM) | Xanthine Oxidase IC50 (μM) |
|---|---|---|
| Formula (III$_a$) | | 4.5 |
| Allopurinol | >300† | 2.0 to 5.0 |
| Lesinurad | 18.61* | >300† |
| | 52.5 ± 5.9†* | |

The results of these assays for compounds according to Formula (IV) are shown in Table 4:

TABLE 4

| Compound | URAT1 IC50 (μM) | Xanthine Oxidase IC50 (μM) |
|---|---|---|
| Formula (IV$_a$) | | 8.6 |
| Formula (IV$_b$) | | >300 |
| Formula (IV$_c$) | | >300 |
| Allopurinol | >300† | 2.0 to 5.0 |
| Lesinurad | 18.61* | >300† |
| | 52.5 ± 5.9†* | |

The results of these assays for compounds according to Formula (V) are shown in Table 5:

TABLE 5

| Compound | URAT1 IC50 (μM) | Xanthine Oxidase IC50 (μM) |
|---|---|---|
| Formula (V$_a$) | | 36.1 |
| Allopurinol | >300† | 2.0 to 5.0 |
| Lesinurad | 18.61* | >300† |
| | 52.5 ± 5.9†* | |

The results of these assays for compounds according to Formula (VI) are shown in Table 6:

TABLE 6

| Compound | URAT1 IC50 (μM) | Xanthine Oxidase IC50 (μM) |
|---|---|---|
| Formula (VI$_a$) | >37.5 | 0.61 |
| Formula (VI$_b$) | >27 | 0.14 |
| Formula (VI$_c$) | | 2.5 |
| Allopurinol | >300† | 2.0 to 5.0 |
| Lesinurad | 18.61* | >300† |
| | 52.5 ± 5.9†* | |

The results of these assays for compounds according to Formula (VII) are shown in Table 7:

TABLE 7

| Compound | URAT1 IC50 (μM) | Xanthine Oxidase IC50 (μM) |
|---|---|---|
| Formula (VII$_a$) | | 7 |
| Allopurinol | >300† | 2.0 to 5.0 |
| Lesinurad | 18.61* | >300† |
| | 52.5 ± 5.9†* | |

The results of these assays for compounds according to Formula (VIII) are shown in Table 8:

TABLE 8

| Compound | URAT1 IC50 (μM) | Xanthine Oxidase IC50 (μM) |
|---|---|---|
| Formula (VIII$_a$) | | 17.4 |
| Formula (VIII$_b$) | | 73.8 |
| Allopurinol | >300† | 2.0 to 5.0 |
| Lesinurad | 18.61* | >300† |
| | 52.5 ± 5.9†* | |

All of the compounds tested inhibited at least one of URAT1 and xanthine oxidase. Formulae (I$_a$), (I$_c$), (I$_e$), (I$_f$), (I$_g$), (I$_h$), (I$_k$), (II$_b$), (II$_d$), (II$_e$), (VI$_a$) and (VI$_b$) are particularly potent inhibitors of xanthine oxidase compared to allopurinol. Several of the compounds also effectively inhibit URAT1, although not all of them were tested. These are bifunctional inhibitors. One representative example of a particularly effective bifunctional inhibitor is Formula (II$_d$).

While many compounds were potent inhibitors, the extent of inhibition of each enzyme/channel was different. Such variability allows the intelligent selection of a pharmaceutically acceptable product that exhibits greater or lesser inhibition of one or the other enzyme target. For example, greater inhibition of XO might be deemed preferable for a patient whose primary metabolic defect was over-production of uric acid. Conversely, greater inhibition of URAT1 might be deemed preferable for a patient whose primary metabolic defect was under-excretion of uric acid. However, it should be noted that almost all patients with hyperuricemia will benefit from reduction in serum uric acid, and bifunctional compounds can be expected to exert a beneficial effect in such patients. The practitioner, guided by the present disclosure, will be able to select particular compounds as appropriate for a specific use based on the level of skill in the art.

By way of comparison, allopurinol has an IC50 for XO ranging from about 2.0 to about 5.0 μM and an IC50 for URAT1 of >300 μM. Lesinurad has an IC50 for XO of >300 NM and an IC50 for URAT1 ranging from 18 to 53 μM. Thus, neither of these compounds is considered bifunctional, since both are selective inhibitors of only one enzyme that affects either production or excretion of uric acid. In contrast, certain of the compounds described herein are not only bifunctional, several are substantially more potent inhibitors of either or both XO and URAT1.

While in many clinical situations it is desirable to treat hyperuricemia with a drug that is highly potent against both XO and URAT1, it is also contemplated that selection of a particular compound of the invention for treatment of hyperuricemia may be based on the phenotype of the hyperuricemic patient being treated (i.e., the relative contributions of over-production of uric acid and under-excretion of uric acid to the patient's specific disease). Where over-production of uric acid predominates, use of compounds according to the invention that are substantially more potent against XO than URAT1 may be appropriate. Where under-excretion of uric acid predominates, use of compounds according to the invention that are substantially more potent against URAT1 than XO may be appropriate. Although the genetics of these two pathways are not completely understood, chemical testing to determine the extent to which each contributes to the hyperuricemia of a particular patient has been published, and is expected to be useful to determine the patient's disease phenotype for selection of an appropriate drug.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A compound selected from the group consisting of
   a) compounds having a structure represented by Formula (I):

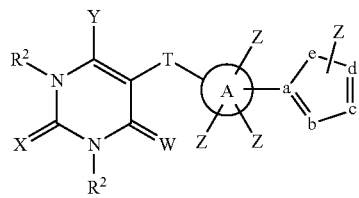

Formula (I)

wherein
  W is selected from O, S, and NR², Y is selected from OH and N(R²)₂, X is selected from O, S, and NR²;
  T is —CONR²—, —C(NR²)NH—, —C(NOR²)NH—, —C(N-NR²)NH—, —C(SR²)N—, or —NHC(O)—;
  A is phenyl, heteroaryl, C5-C10 branched or unbranched cycloalkyl, C6-C10 bicycloalkyl or C5-C10 spirocycloalkyl;
  each Z is independently present or absent and, if present, is independently selected from one or more halogen atoms, —CN, —CF₃, —OR², —C(O)R², SR², —S(O)$_g$R³ where g is 1 or 2, —N(R²)₂, —NO₂, —CO₂R², —OCO₂R³, OC(O)R², —CON(R²)₂, —NR²C(O)R², —SO₂N(R²)₂, —NR²SO₂R³, —NR²SO₂N(R²)₂ or —NR²C(O)N(R²)₂, —C(O)NHOR², alkyl, aryl, alkenyl and alkynyl;
wherein each R² is independently H, alkyl or aryl;
wherein each R³ is independently alkyl or aryl, optionally substituted with one or more halogen atoms or OR²; and
wherein a, b, c, d, and e are each independently carbon or nitrogen, or four of a, b, c, d, and e are each independently carbon or nitrogen and one of a, b, c, d, and e is O, with the proviso that at least one of a, b, c, d and e is nitrogen, and Z is not connected directly to nitrogen or oxygen; and
  tautomers thereof,
  b) compounds having a structure represented by Formula (III):

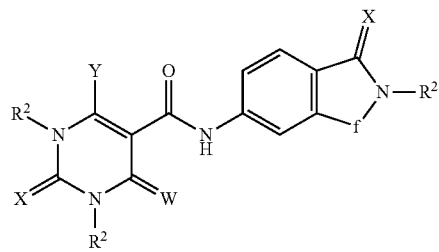

Formula (III)

wherein
  W is selected from O, S, and NR², Y is selected from OH and N(R²)₂, X is selected from O, S, and NR²;
  each R² is independently H, alkyl or aryl; and
  f is divalent —CR²—, —C(O)—, —SR², —S(O)$_g$— where g is 1 or 2, —N(R)₂—; or —C(—O(CR²)$_n$O—)— where n=2–3; and
  tautomers thereof,
  c) compounds having a structure represented by Formula (IV):

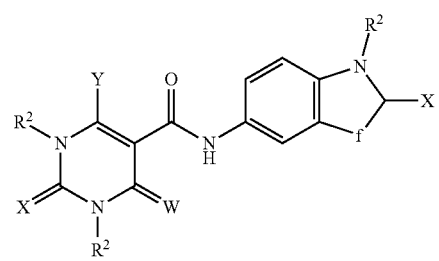

Formula (IV)

wherein
  W is selected from O, S, and NR², Y is selected from OH and N(R²)₂, X is selected from O, S, and NR²;
  each R² is independently H, alkyl or aryl; and
  f is divalent —CR²—, —C(O)—, —S(O)$_g$— where g is 1–2, —N(R²)₂—; or —C(—O(CR²)$_n$O—)— where n is 2–3; and
  tautomers thereof,
  d) compounds having a structure represented by Formula (V):

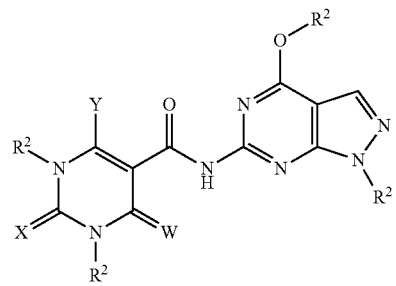

Formula (V)

wherein
W is selected from O, S, and $NR^2$, Y is selected from OH and $N(R^2)_2$, X is selected from O, S, and $NR^2$; and
each $R^2$ is independently H, alkyl or aryl; and
tautomers thereof, and
e) compounds having a structure represented by Formula (VIII):

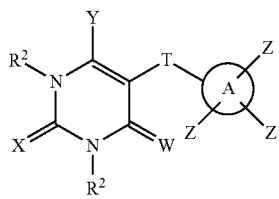

Formula (VIII)

wherein
the structure is selected from the group consisting of

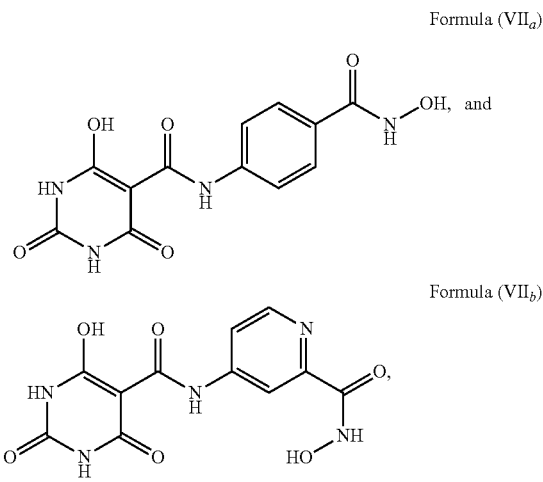

Formula (VII$_a$)

Formula (VII$_b$)

and
tautomers thereof.

2. The compound according to claim 1, wherein the 5-member heterocyclic ring is a substituted or unsubstituted triazole.

3. The compound according to claim 1, wherein —$XR^1$ is —$SCH_3$ or —$OCH_3$.

4. The compound according to claim 1 wherein, in Formula (I):
a) X and W are each independently O or S;
b) Y is OH or $NH_2$;
c) T is —C(NH)NH—, —NHC(O)—, —C($SCH_3$)N—, —C(NOH)NH—, —C(N—$NH_2$)NH—, or —CONH;
d) each $R^2$ on the barbiturate ring is independently H or $CH_3$;
e) A is phenyl, branched cycloalkyl, or unbranched cycloalkyl; and
f) Z, if present, is phenyl or $CF_3$.

5. The compound according to claim 1, wherein, in Formula (III), f is —$S(O)_2$—.

6. The compound according to claim 1 wherein, in Formula (IV), f is —NH—, —C(O)— or —C(—$O(CH_2)_2O$—)—.

7. The compound according to claim 6, wherein X on the fused ring structure is O.

8. The compound according to claim 1 wherein, in Formula (V), each $R^2$ is H.

9. A pharmaceutical composition comprising the compound of claim 1 having the structure represented by any of Formulae (I)-(V), and (VIII); a tautomer of any of Formulae (I)-(V), and (VIII), or a combination thereof, and a pharmaceutically acceptable carrier.

10. The pharmaceutical composition according to claim 9, which is formulated for controlled or extended release of the compound or combination thereof.

11. The pharmaceutical composition according to claim 9, wherein the pharmaceutically acceptable carrier is selected from the group consisting of water or saline, a solvent, a dispersing agent, a coating, a surfactant, a preservative, an emulsion, an alcohol, a polyol, and an isotonic agent.

12. A method for reducing uric acid levels in blood or serum of a subject, or preventing elevation of uric acid levels in blood or serum of a subject, comprising administering to a subject in need thereof the compound of claim 1 having the structure represented by any of Formulae (I)-(V), and (VIII); a tautomer of any of Formulae (I)-(V), and (VIII), or a combination thereof, in an amount effective to reduce blood or serum uric acid levels.

13. The method according to claim 12, wherein administering the compound treats or prevents a disorder of uric acid metabolism caused by, or associated with, hyperuricemia.

14. The method of claim 12, wherein the disorder of uric acid metabolism is selected from the group consisting of gout, hyperuricemia, tumor lysis syndrome, kidney disease, arthritis, kidney stones, kidney failure, urolithiasis, plumbism, hyperparathyroidism, psoriasis, inborn genetic errors of metabolism, Lesch-Nyhan syndrome, sarcoidosis, cardiovascular disease, atherosclerosis, and disorders of uric acid metabolism associated with transplantation of blood, bone marrow or solid organs.

15. The method according to claim 12, wherein a daily dose of about 20 to about 1,500 mg/$m^2$/day is administered.

16. The method according to claim 12, wherein the compound or combination thereof is administered by injection, infusion, or oral administration.

17. The method according to claim 16, wherein the compound or combination thereof is administered by intravenous infusion or bolus injection.

* * * * *

UNITED STATES PATENT AND TRADEMARK OFFICE
CERTIFICATE OF CORRECTION

PATENT NO. : 11,168,075 B2
APPLICATION NO. : 16/928623
DATED : November 9, 2021
INVENTOR(S) : John J. Piwinski et al.

Page 1 of 1

It is certified that error appears in the above-identified patent and that said Letters Patent is hereby corrected as shown below:

In the Specification

Column 3, Line 13, replace "$CO_2R^3$" after "$CO_2R^2$" and before "$OC(O)R^2$" with "$OCO_2R^3$".
Column 4, Line 21, replace "-(-C(-O(CR$^2$)" after "N(R')$_2$-; or" with "-(-C(-O(CR$^2$)$_n$".
Column 6, Line 28, replace "$CO_2R^3$" after "$CO_2R^2$" and before "$OC(O)R^2$" with "$OCO_2R^3$".
Column 16, Line 20, replace "Formula (I)" after "represented by" with "Formula (I$_n$)".
Column 16, Line 59, replace "$CO_2R^3$" after "$CO_2R^2$" and before "$OC(O)R^2$" with "$OCO_2R^3$".
Column 17, Line 67, replace "Formula (II)" after "by" with "Formula (II$_c$)".
Column 18, Line 17, insert --Formula (II$_d$)-- after "represented by".
Column 20, Line 37, replace "NR" after "2" and before "or -C(-O(CR$^2$)$_n$O-)-" with "NR$^2$".
Column 22, Line 38 replace "$CO_2R^3$" after "$CO_2R^2$" and before "$OC(O)R^2$" with "$OCO_2R^3$".
Column 51, Line 40, replace "[M-1]-" after "m/z" and before "=359.06" with "[M-1]$^-$".

In the Claims

Column 62, Line 25 replace "N(R)$_2$" after "1 or 2" and before "or -C(-O(CR$^2$)" with "N(R')$_2$".

Column 62, Line 35, replace formula (IV) " 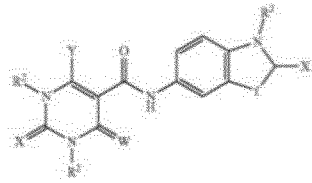 " with " 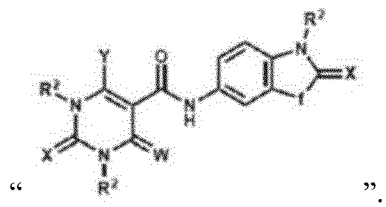 ".

Signed and Sealed this
Twenty-eighth Day of December, 2021

Drew Hirshfeld
*Performing the Functions and Duties of the
Under Secretary of Commerce for Intellectual Property and
Director of the United States Patent and Trademark Office*